(12) United States Patent
van Dijk et al.

(10) Patent No.: US 10,639,368 B2
(45) Date of Patent: May 5, 2020

(54) ANTI-TIM-3 ANTIBODIES AND METHODS OF USE THEREOF

(71) Applicant: Agenus Inc., Lexington, MA (US)

(72) Inventors: Marc van Dijk, Bilthoven (NL); Ekaterina Vladimirovna Breous-Nystrom, Basel (CH); Nicholas Stuart Wilson, Somerville, MA (US); Jeremy Dale Waight, Everett, MA (US); Dennis John Underwood, Boston, MA (US)

(73) Assignee: AGENUS INC., Lexington, MA (US)

( * ) Notice: Subject to any disclaimer, the term of this patent is extended or adjusted under 35 U.S.C. 154(b) by 55 days.

(21) Appl. No.: 15/606,148

(22) Filed: May 26, 2017

(65) Prior Publication Data

US 2017/0368168 A1 Dec. 28, 2017

Related U.S. Application Data

(60) Provisional application No. 62/342,610, filed on May 27, 2016, provisional application No. 62/420,276, filed on Nov. 10, 2016.

(51) Int. Cl.
| | | |
|---|---|---|
| *A61K 39/395* | (2006.01) | |
| *C07K 16/30* | (2006.01) | |
| *C07K 16/40* | (2006.01) | |
| *C07K 16/28* | (2006.01) | |

(52) U.S. Cl.
CPC ........ *A61K 39/395* (2013.01); *C07K 16/2803* (2013.01); *C07K 2317/34* (2013.01); *C07K 2317/52* (2013.01); *C07K 2317/565* (2013.01); *C07K 2317/71* (2013.01); *C07K 2317/732* (2013.01); *C07K 2317/76* (2013.01); *C07K 2317/77* (2013.01); *C07K 2317/92* (2013.01); *C07K 2317/94* (2013.01); *C07K 2319/55* (2013.01)

(58) Field of Classification Search
CPC .................. A61K 39/395; C07K 2317/565
USPC ..................................................... 424/138.1
See application file for complete search history.

(56) References Cited

U.S. PATENT DOCUMENTS

| | | | |
|---|---|---|---|
| 5,585,097 A | 12/1996 | Bolt et al. | |
| 7,172,750 B2 | 2/2007 | Levinson et al. | |
| 7,470,428 B2 | 12/2008 | Kuchroo et al. | |
| 7,838,220 B2 | 11/2010 | McIntire et al. | |
| 8,101,176 B2 | 1/2012 | Kuchroo et al. | |
| 8,552,156 B2 | 10/2013 | Takayanagi et al. | |
| 8,591,886 B2 | 11/2013 | Ponath et al. | |
| 8,697,069 B2 | 4/2014 | Kuchroo et al. | |
| 8,709,412 B2 | 4/2014 | Jones et al. | |
| 8,709,715 B2 | 4/2014 | Karsunky et al. | |
| 9,132,281 B2 | 9/2015 | Zeng et al. | |
| 9,163,087 B2 | 10/2015 | Kuchroo et al. | |
| 9,333,256 B2 | 5/2016 | Kuchroo et al. | |
| 9,605,070 B2 | 3/2017 | Sabatos-Peyton et al. | |
| 2005/0276756 A1 | 12/2005 | Hoo et al. | |
| 2009/0041752 A1 | 2/2009 | Levinson et al. | |
| 2010/0247521 A1 | 9/2010 | Jones et al. | |
| 2014/0044728 A1 | 2/2014 | Takayanagi et al. | |
| 2015/0037346 A1 | 2/2015 | Lesokhin et al. | |
| 2015/0118222 A1 | 4/2015 | Levy et al. | |
| 2015/0174268 A1 | 6/2015 | Li et al. | |
| 2015/0190505 A1 | 7/2015 | Yeung et al. | |
| 2015/0202291 A1 | 7/2015 | Bosch et al. | |
| 2015/0218274 A1 | 8/2015 | Sabatos-Peyton et al. | |
| 2015/0297677 A1 | 10/2015 | Choe et al. | |
| 2015/0368349 A1* | 12/2015 | Gonzalez ........... | C07K 16/2878 424/139.1 |
| 2016/0159905 A1 | 6/2016 | Abdiche et al. | |
| 2016/0159927 A1 | 6/2016 | Molloy et al. | |
| 2016/0185870 A1 | 6/2016 | Eenennaam et al. | |
| 2016/0193239 A1 | 7/2016 | Baylin et al. | |
| 2016/0222121 A1 | 8/2016 | Duane et al. | |
| 2016/0257758 A1 | 9/2016 | Gray et al. | |
| 2017/0007698 A1 | 1/2017 | Kim et al. | |
| 2017/0028047 A1 | 2/2017 | Akle et al. | |
| 2017/0037133 A1 | 2/2017 | Fiedler et al. | |
| 2017/0042995 A1 | 2/2017 | Ali et al. | |
| 2017/0042997 A1 | 2/2017 | Wirth et al. | |
| 2017/0051061 A1 | 2/2017 | Snyder et al. | |
| 2017/0106048 A1 | 4/2017 | Kunz et al. | |
| 2017/0114135 A1 | 4/2017 | Codarri-Deak et al. | |
| 2017/0143780 A1 | 5/2017 | Zitvogel et al. | |
| 2017/0198040 A1* | 7/2017 | Balke .................. | A61K 39/395 |

(Continued)

FOREIGN PATENT DOCUMENTS

| | | |
|---|---|---|
| CN | 101035561 A | 9/2007 |
| CN | 102492038 B | 6/2012 |

(Continued)

OTHER PUBLICATIONS

Rudikoff et al., PNAS 1982, vol. 79, pp. 1979-1983.*

(Continued)

*Primary Examiner* — Lynn A Bristol
(74) *Attorney, Agent, or Firm* — Lathrop GPM LLP; Andrew T. Wilkins; Rebecca L. Wright

(57) ABSTRACT

The instant disclosure provides antibodies that specifically bind to TIM-3 (e.g., human TIM-3) and antagonize TIM-3 function. Also provided are pharmaceutical compositions comprising these antibodies, nucleic acids encoding these antibodies, expression vectors and host cells for making these antibodies, and methods of treating a subject using these antibodies.

Figure 1:
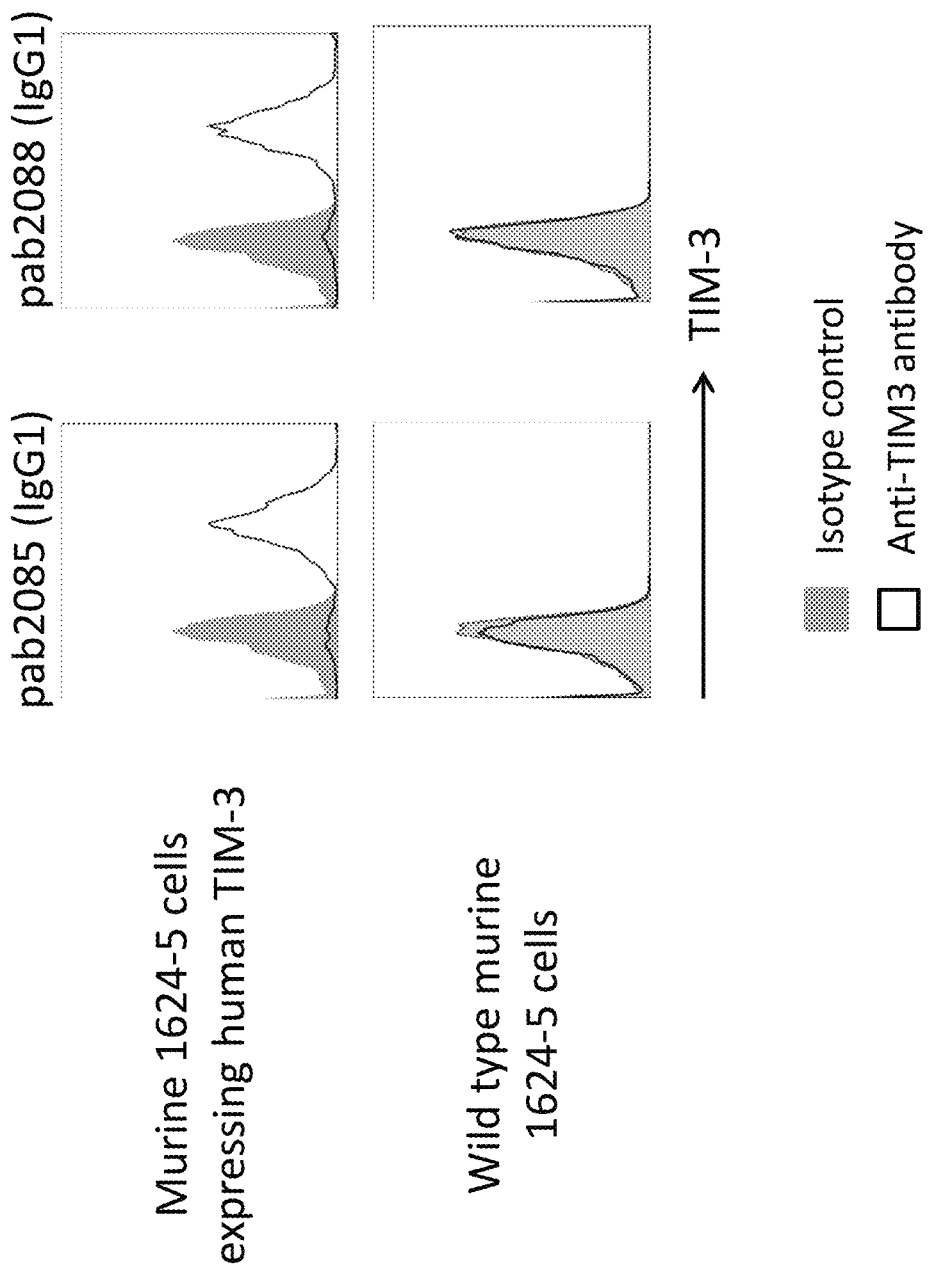

32 Claims, 26 Drawing Sheets
Specification includes a Sequence Listing.

(56) References Cited

U.S. PATENT DOCUMENTS

| | | | |
|---|---|---|---|
| 2018/0127499 A1* | 5/2018 | Wilson | A61K 47/6873 |
| 2018/0244793 A1* | 8/2018 | Gonzalez | C07K 16/2878 |
| 2018/0355051 A1* | 12/2018 | Gonzalez | C07K 16/2878 |
| 2019/0010239 A1* | 1/2019 | Gonzalez | C07K 16/2878 |

FOREIGN PATENT DOCUMENTS

| | | |
|---|---|---|
| EP | 1685159 B1 | 8/2012 |
| EP | 2212350 B1 | 8/2013 |
| EP | 2879709 A1 | 6/2015 |
| EP | 3217993 A1 | 7/2015 |
| EP | 2271672 B1 | 11/2015 |
| WO | WO 1996027603 A1 | 9/1996 |
| WO | WO 2001077342 A1 | 10/2001 |
| WO | WO 2003002722 A2 | 1/2003 |
| WO | WO 2003063792 A2 | 8/2003 |
| WO | WO 2005027846 A2 | 3/2005 |
| WO | WO 2005027854 A2 | 3/2005 |
| WO | WO 2005033144 A2 | 4/2005 |
| WO | WO 2005097211 A2 | 10/2005 |
| WO | WO 2005123779 A2 | 12/2005 |
| WO | WO 2006066229 A2 | 6/2006 |
| WO | WO 2007024715 A2 | 3/2007 |
| WO | WO 2007146968 A2 | 12/2007 |
| WO | WO 2008024188 A2 | 2/2008 |
| WO | WO 2008060617 A2 | 5/2008 |
| WO | WO 2008071447 A2 | 6/2008 |
| WO | WO 2008138017 A2 | 11/2008 |
| WO | WO 2008147143 A2 | 12/2008 |
| WO | WO 2009052623 A1 | 4/2009 |
| WO | WO 2009064290 A1 | 5/2009 |
| WO | WO 2009091547 A1 | 7/2009 |
| WO | WO 2009097394 A2 | 8/2009 |
| WO | WO 2009120899 A2 | 10/2009 |
| WO | WO 2009120903 A2 | 10/2009 |
| WO | WO 2009120905 A2 | 10/2009 |
| WO | WO 2009131572 A1 | 10/2009 |
| WO | WO 2010084999 A1 | 7/2010 |
| WO | WO 2010110346 A1 | 9/2010 |
| WO | WO 2010117057 A1 | 10/2010 |
| WO | WO 2011034969 A1 | 3/2011 |
| WO | WO 2011109789 A2 | 9/2011 |
| WO | WO 2011155607 A1 | 12/2011 |
| WO | WO 2011159877 A2 | 12/2011 |
| WO | WO 2012088290 A2 | 6/2012 |
| WO | WO 2012088302 A2 | 6/2012 |
| WO | WO 2012177624 A2 | 12/2012 |
| WO | WO 2012177788 A1 | 12/2012 |
| WO | WO 2013006490 A2 | 1/2013 |
| WO | WO 2013006727 A1 | 1/2013 |
| WO | WO 2013114367 A2 | 8/2013 |
| WO | WO 2013124327 A1 | 8/2013 |
| WO | WO 2013126809 A1 | 8/2013 |
| WO | WO 2013132044 A1 | 9/2013 |
| WO | WO 2014022332 A1 | 2/2014 |
| WO | WO 2014089113 A1 | 6/2014 |
| WO | WO 2015136541 A2 | 9/2015 |
| WO | WO 2015142675 A2 | 9/2015 |
| WO | WO 2015155738 A2 | 10/2015 |
| WO | WO 2015174439 A1 | 11/2015 |
| WO | WO 2015200828 A1 | 12/2015 |
| WO | WO 2016004875 A1 | 1/2016 |
| WO | WO 2016007513 A1 | 1/2016 |
| WO | WO 2016020538 A1 | 2/2016 |
| WO | WO 2016022971 A1 | 2/2016 |
| WO | WO 2016025647 A1 | 2/2016 |
| WO | WO 2016028656 A1 | 2/2016 |
| WO | WO 2016028672 A1 | 2/2016 |
| WO | WO 2016040892 A1 | 3/2016 |
| WO | WO 2016054555 A2 | 4/2016 |
| WO | WO 2016057898 A1 | 4/2016 |
| WO | WO 2016065330 A1 | 4/2016 |
| WO | WO 2016068802 A1 | 5/2016 |
| WO | WO 2016068803 A1 | 5/2016 |
| WO | WO 2016071448 A1 | 5/2016 |
| WO | WO 2016077553 A1 | 5/2016 |
| WO | WO 2016079050 A1 | 5/2016 |
| WO | WO 2016081746 A2 | 5/2016 |
| WO | WO 2016081947 A2 | 5/2016 |
| WO | WO 2016100882 A1 | 6/2016 |
| WO | WO 2016111947 A2 | 7/2016 |
| WO | WO 2016118654 A1 | 7/2016 |
| WO | WO 2016123285 A1 | 8/2016 |
| WO | WO 2016126213 A1 | 8/2016 |
| WO | WO 2016128542 A1 | 8/2016 |
| WO | WO 2016144976 A1 | 9/2016 |
| WO | WO 2016149665 A1 | 9/2016 |
| WO | WO 2016154544 A1 | 9/2016 |
| WO | WO 2016160972 A1 | 10/2016 |
| WO | WO 2016161270 A1 | 10/2016 |
| WO | WO 2016171722 A1 | 10/2016 |
| WO | WO 2016172417 A2 | 10/2016 |
| WO | WO 2016176761 A1 | 11/2016 |
| WO | WO 2016179194 A1 | 11/2016 |
| WO | WO 2016180781 A1 | 11/2016 |
| WO | WO 2016191643 A2 | 12/2016 |
| WO | WO 2016193680 A1 | 12/2016 |
| WO | WO 2016197204 A1 | 12/2016 |
| WO | WO 2016210223 A1 | 12/2016 |
| WO | WO 2017009829 A1 | 12/2016 |
| WO | WO 2017019767 A1 | 2/2017 |
| WO | WO 2017019897 A1 | 2/2017 |
| WO | WO 2017023749 A1 | 2/2017 |
| WO | WO 2017025496 A1 | 2/2017 |
| WO | WO 2017025871 A1 | 2/2017 |
| WO | WO 2017030823 A2 | 2/2017 |
| WO | WO 2017031242 A1 | 2/2017 |
| WO | WO 2017040666 A2 | 3/2017 |
| WO | WO 2017042633 A2 | 3/2017 |
| WO | WO 2017053748 A2 | 3/2017 |
| WO | WO 2017055393 A1 | 4/2017 |
| WO | WO 2017059095 A1 | 4/2017 |
| WO | WO 2017059319 A2 | 4/2017 |
| WO | WO 2017068186 A1 | 4/2017 |
| WO | WO 2017070110 A1 | 4/2017 |
| WO | WO 2017079116 A2 | 5/2017 |
| WO | WO 2017087547 A1 | 5/2017 |

OTHER PUBLICATIONS

Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Afanasiev, O.K., et al., (2013) "Merkel Polyomavirus-Specific T Cells Fluctuate with Merkel Cell Carcinoma Burden and Express Therapeutically Targetable PD-1 and Tim-3 Exhaustion Markers" Clin. Cancer Res. 19(19):5351-60.
Agenus Slide Deck for Agenus R&D Day (NY) dated Nov. 19, 2015.
Al-Lazikani B et al., (1997) "Standard Conformations for the Canonical Structures of Immunoglobulins" J M Biol 273: 927-948.
Anderson, A.C., (2012) "Tim-3, a negative regulator of anti-tumor immunity" Current Opinion in Immunology 24:213-216.
Anderson, A.C., (2014) "Tim-3: An Emerging Target in the Cancer Immunotherapy Landscape" Cancer Immunol. Res. 2(5):393-8.
Anderson, A.C., et al., (2016) "Lag-3, Tim-3, and TIGIT: Co-inhibitory Receptors with Specialized Functions in Immune Regulation" Immunity 44:989-1004.
Andorsky, D.J., et al., (2011) "Programmed death ligand 1 is expressed by non-Hodgkin Lymphomas and inhibits the activity of tumor-associated T cells" Cancer Res. 17(13):4232-44.
Baghdadi, M., et al., (2014) "The impact of the TIM gene family on tumor immunity and immunosuppression" Cellular & Molecular Immunology 11:41-48.
Cao, E., et al., (2007) "T cell immunoglobulin mucin-3 crystal structure reveals a galectin-9-independent ligand-binding surface" 26(3):311-21.

(56) References Cited

OTHER PUBLICATIONS

Chae, S., et al., (2004) "Molecular variations in Th1-specific cell surface gene Tim-3" Exp. Mol. Moed. 36(3):274-8.
Champe, M et al., (1995) "Monoclonal Antibodies that Blocak the Activity of Leukocyte Functions-Associated Antigen 1" J Biol Chem 270: 1388-1394.
Cheung, RC et al., "Epitope-specific Antibody Response to the Surface of Duck Hepatitis B Virus" (1990) Virology 176: 546-52.
Chiba, S., et al. (2012) "Tumor-infiltrating DCs suppress nucleic acid-mediated innate immune responses through interactions between the receptor TIM-3 and the alarmin HMGB1" Nat. Immunol. 13(9):832-42.
Chothia, C & Lesk AM, (1987), "Canonical Structures for the Hypervariable Regions of Immunoglobulins" J Mol Biol 196: 901-917.
Chothia, C et al., (1992) "Structural Repertoire of Human VH Segments" J Mol Biol 227: 799-817.
Clayton, K.L., et al., (2014) "T Cell Ig an Mucin Domain-Containing Protein 3 Is Recruited to the Immune Synapse, Disrupts Stable Synapse Formation, and Associates with Receptor Phosphatases" J. Immunol. 192:782-791.
Cockett, MI et al., (1990) "High Level Expression of Tissue Inhibitor of Metalloproteinases in Chinese Hamster Ovary Cells Using Glutamine Synthetase Gene Amplification" Biotechnology 8(7): 662-7.
Correia, JDS et al. "Identification and Characterization of a Potent Anti-Human Tim-3 Antagonist" Abstract From ACCR Conference: Tumor Immunology and Immunotherapy: A New Chapter, Dec. 2, 2014.
Cunningham, BC & Wells JA (1989) "High-Resolution Epitope Mapping of hGH-Receptor Interactions by Alanine-Scanning Mutagenesis" Science 244: 1081-1085.
Dall'Acqua, WF et al., (2006) "Properties of Human Igg1s Engineered for Enhanced Binding to the Neonatal Fc Receptor (Fcrn)" J Biol Chem 281: 23514-24.
Da Silva, I.P., et al., (2014) "Reversal of NK-cell Exhaustion in Advanced Melanoma by Tim-3 Blockade" Cancer Immunol. Res. 2(5):410-22.
Dietze, K.K., et al., (2013) "Combining regulatory T cell depletion and inhibitory receptor blockade improves reactivation of exhausted virus-specific CD8+ T cells and efficiently reduces chronic retroviral loads" PLoS Pathog. 9(12):e1003798.
Drake, C.G., (2015) "Combined Immune Checkpoint Blockade" Semin. Oncol. 42:656-662.
Edelman, G.M. et al., (1969) "The Covalent Structure of an Entire Gammag Immunoglobulin" Molecule. Proc. Natl. Acad. Usa, 63, 78-85.
Fehlings, M., et al., (2017) "Checkpoint blockade immunotherapy reshapes the high-dimensional phenotypic heterogeneity of murine intratumoural neoantigen-specific CD8+ T cells" Nature Communications 8(1):562.
Ferris, R.L., et al., (2014) "Too much of a good thing? Tim-3 and TCR signaling in T cell exhaustion" J. of Immunol. 193(4):1525-30.
Fourcade, J., et al., (2010) "Upregulation of Tim-3 and PD-1 expression is associated with tumor antigen-specific CD8+ T cell dysfunction in melanoma patients." J. Exp. Med. 207(10):2175-86.
Fourcade, J., et al., (2014) "PD-1 and Tim-3 regulate the expansion of tumor antigen-specific CD8+ T cells induced by melanoma vaccines." Cancer Res. 74(4):1045-55.
Freeman, G.J., et al., (2010) "TIM genes: a family of cell surface phosphatidylserine receptors that regulate innate and adaptive immunity" 235(1):172-89.
Gallois, A., et al., (2014) "Reversal of natural killer cell exhaustion by TIM-3 blockade" OncoImmunology 3(12):ep46365.
Gao, X., et al., (2012) "TIM-3 Expression Characterizes Regulatory T Cells in Tumor Tissues and is Associated with Lung Cancer Progression" 7(2):e30676.
Gray-Owen, S.D., et al., (2006) "CEACAM1: contact-dependent control of immunity" Nat. Rev. Immunol. 6(6):433-46.

Gros, A., et al., (2014) "PD-1 identifies the patient-specific CD8+ tumor-reactive repertoire infiltrating human tumors." J. Clin. Invest. 124(5):2246-59.
Guo, Z., et al., (2013) "Combined TIM-3 blockade and CD137 activation affords the long-term protection in a murine model of ovarian cancer." J. Tran. Med. 11(215):1-11.
Han, G., et al., (2013) "Tim-3: an activation marker and activation limiter of innate immune cells" Front. In Immunol. 4(449):1-7.
Hastings, W.D., et al., (2009) "TIM-3 is expressed on activated human CD4+ T cells and regulates Th1 and Th17 cytokines." Eur. J. Immunol. 39(9):2492-501.
Hervas-Stubbs, S., et al., (2015) "Identification of TIM3 2'-fluoro oligonucleotide aptamer by HT-SELEX for cancer immunotherapy" Oncotarget 7(4):4522-30.
Ho, L.H., et al., (2007) "IL-33 induces IL-13 production by mouse mast cells independently of IgE-FcεRI signals." J. Leukoc. Biol. 82(6):1481-90.
Hou, H., et al., (2014) "Tim-3 Negatively Mediates Natural Killer Cell Function in LPS-Induced Endotoxic Shock" PLoS One 9(10):e110585.
Huang, Y.H., et al., (2015) "CEACAM1 regulates TIM-3-mediated tolerance and exhaustion" Nature 517(7534):386-90.
Huang, Z., et al., (2007) "Lymphoma endothelium preferentially expresses Tim-3 and facilitates the progression of lymphoma by mediating immune evasion" J. Exp. Med. 207(3):505-520.
Jajosky, A.N., et al., (2014) "RepSox Slows Decay of CD34+ Acute Myeloid Leukemia Cells and Decreases T Cell Immunoglobulin Mucin-3 Expression" Stem Cells Transl. Med. 3:836-848.
Jiang, Y., et al., (2015) "T-cell exhaustion in the tumor microenvironment" Cell Death and Disease 6:e1792.
Jie, H., et al., (2017) "Increased PD-1+ and TIM-3+ TILs during Cetuximab Therapy Inversely Correlate with Response in Head and Neck Cancer Patients" Cancer Immunol Res; 5(5):408-16.
Jin, H., et al., (2010) "Cooperation of Tim-3 and PD-1 in CD8 T-cell exhaustion during chronic viral infection" Proc. Natl. Acad. Sci. USA 107(33):14733-8.
Jing, W., et al., (2015) "Combined immune checkpoint protein blockade and low dose whole body irradiation as immunotherapy for myeloma" Journal for ImmunoTherapy of Cancer 3(2):1-15.
Jinushi, M., et al., (2012) "Regulatory mechanisms of nucleic acid-mediated innate immune responses in the tumor microenvironment" OncoImmunology 1(9):1632-1634.
Jun, H.T., et al., (2014) "Generation of antagonistic anti-TIM-3 and anti-LAG-3 monoclonal antibodies for potential novel immunotherapy combinations" AnaptysBio ACCR Poster LB-266.
Kang, C., et al., (2015) "Apoptosis of tumor infiltrating effector TIM-3+CD8+ T cells in colon cancer" Scientific Reports 5(15659):1-12.
Kikushige, Y., et al., (2010) "TIM-3 Is a Promising Target to Selectively Kill Acute Myeloid Leukemia Stem Cells" Cell Stem Cell 7:708-717.
Kikushige, Y., et al., (2012) "TIM-3 as a therapeutic target for malignant stem cells in acute myelogenous leukemia" Ann. N.Y. Acad. Sci. 1266:118-123.
Kikushige, Y., et al., (2015) "A TIM-3/Gal-9 Autocrine Stimulatory Loop Drives Self-Renewal of Human Myeloid Leukemia Stem Cells and Leukemic Progression" Cell Stem Cell 17(3):341-52.
Kim, P.S., et al., (2010) "Features of responding T cells in cancer and chronic infection" Current Opin. In Immunol. 22:223-230.
Kirkland, TN et al., (1986) "Analysis of the Fine Specificity and Cross-Reactivity of Monoclonal Anti-Lipid A Antibodies" J Immunol 137: 3614-9.
Köhler, G "Immunoglobulin Chain Loss in Hybridoma Lines" (1980) Pnas 77: 2197-2199.
Komohara, Y., et al., (2015) "The Coordinated Actions of TIM-3 on Cancer and Myeloid Cells in the Regulation of Tumorigenicity and Clinical Prognosis in Clear Cell Renal Cell Carcinomas" Cancer Immunol. Res. 3(9):999-1007.
Koyama, S., et al., (2016) "Adaptive resistance to therapeutic PD-1 blockade is associated with upregulation of alternative immune checkpoints" Nature Communications 7(10501):1-9.

(56) References Cited

OTHER PUBLICATIONS

Kuroki M et al., (1990) "Serological Mapping of the Tag-72 Tumor-Associated Antigen Using 19 Distinct Monoclonal Antibodies" Cancer Res 50: 4872-4879.
Kuroki M et al., (1992) "Determination of Epitope Specificities of a Large Number of Monoclonal Antibodies by Solid-Phase Mutual Inhibition Assays Using Biotinylated Antigen" Immunol Invest 21: 523-538.
Kutmeier G et al., (1994), "Assembly of Humanized Antibody Genes From Synthetic Oligonucleotides Using a Single-Round Pcr" Biotechniques 17: 242-6.
Lefranc M-P et al., (1999) "Imgt, The International Immunogenetics Database" Nucleic Acids Res 27: 209-212.
Leitner, J., et al., (2013) "TIM-3 does not act as a receptor for galectin-9" PLoS Pathog 9(3):e1003253.
Li, Y., et al., (2017) "T im-3 signaling in peripheral NK cells promotes maternal-fetal immune tolerance and alleviates pregnancy loss" Sci. Signal. 10(eaah4323):1-15.
Li, Z., et al., (2012) "TIM3 gene polymorphisms in patients with chronic hepatitis B virus infection: impact on disease susceptibility and hepatocellular carcinoma traits" Tissue Antigens 80:151-157.
Maccallum et al., (1996) "Antibody-Antigen Interactions: Contact Analysis and Binding Site Topography" J. Mol. Biol. 262:732-745.
Madireddi, S., et al., (2014) "Galectin-9 controls the therapeutic activity of 4-1BB-targeting antibodies" 211(7):1433-48.
Martin A. (2001) "Protein Sequence and Structure Analysis of Antibody Variable Domains in Antibody Engineering" Kontermann and Dübel, Eds., Chapter 31, pp. 422-439, Springer-Verlag, Berlin.
Mataraza, J., et al., (2015) "Coordinating Immune Checkpoint Blockade for Cancer Immunotherapy in Combination" Immune Oncology, NIBR.
Mataraza, J., et al., (2016) "Checkpoint Inhibitors in Combination: Novartis enters the clinic" Advances in Immuno-oncology Congress.
Mcmahan et al., (2010) "Tim-3 expression on PD-1+ HCV-specific human CTLs is associated with viral persistence, and its blockade restores hepatocyte-directed in vitro cytotoxicity" J. Clin. Invest. 120(12):4546-57.
Mellman, I., et al., (2011) "Cancer immunotherapy comes of age" Nature 480(7378):480-9.
Mercier, I.L., et al., (2015) "Beyond CTLA-4 and PD-1, the generation Z of negative checkpoint regulators" Front. In Immunol. 6(418):1-15.
Meyaard, L., et al., (2012) "Liberating tumor immunity" Current Opin. In Immunol. 24:204-206.
Moldenhauer G et al., (1990) "Identity of Hml-1 Antigen on Intestinal Intraepithelial T Cells and of B-Ly7 Antigen on Hairy Cell Leukaemia" Scand J Immunol 32: 77-82.
Monney, L., et al., (2002) "Th1-specific cell surface protein TIM-3 regulates macrophage activation and severity of an autoimmune disease" Nature Letters vol. 415:536-41.
Nakae et al. (2007) "Phenotypic Differences Between Th1 and Th17 Cells and Negative Regulation of Th1 Cell Differentiation by Il-17" J Leukoc Biol 81: 1258-68.
Ndhlovu, L.C., et al. (2012) "Tim-3 marks human natural killer cell maturation and suppresses cell-mediated cytotoxicity" Blood 119(16):3734-43.
Ngiow, S.F., et al, (2011) "Anti-TIM3 antibody promotes T cell IFN-γ-mediated antitumor immunity and suppresses established tumors." Cancer Res. 71(10):3540-51.
Nguyen, L.T., et al., (2015) "Clinical blockade of PD1 and LAG3-potential mechanisms of action" Nat. Rev. Immunol. 15(1):45-56.
Nigow S.F. et al. (2011) "Prospects for TIM3-Targeted Antitumor Immunotherapy" Cancer Research, AACR—American Association for Cancer Research, US, vol. 71, No. 21, Nov. 1, 2011, pp. 6567-6571.
Nischl, C.J., et al., (2013) "Molecular Pathways: Coexpression of Immune Checkpoint Molecules: Signaling Pathways and Implications for Cancer Immunotherapy" Clin. Cancer Res. 19(18); 4917-24.
Petersson, K., et al., (2002) "Crystal structure of a SEA variant in complex with MHC class II reveals the ability of SEA to crosslink MHC molecules" Structure 10:1619-1626.
Phong, B.L., et al., (2015) "Tim-3 enhances FcεRI-proximal signaling to modulate mast cell activation" J. Exp. Med. 212(13):2289-304.
Rangachari, M., et al., (2012) "Bat3 promotes T cell responses and autoimmunity by repressing Tim-3-mediated cell death and exhaustion" Nature Medicine 18(9):1394-400.
Ryser, S., et al., (2017) "High affinity anti-TIM-3 and anti-KIR monoclonal antibodies cloned from healthy human individuals" PLoS One E 12(7): e0181464.
Sabatos, C.A., et al., (2003) "Interaction of Tim-3 and Tim-3 ligand regulates T helper type 1 responses and induction of peripheral tolerance." Nat. Immunol. 4(11):1102-10.
Sabatos-Peyton, C.A., et al., (2017) "Blockade of Tim-3 binding to phosphatidylserine and CEACAM1 is a shared feature of anti-Tim-3 antibodies that have functional efficacy" Oncoimmunology. 7(2):e1385690.
Sakuishi, K., et al., (2010) "Targeting Tim-3 and PD-1 pathways to reverse T cell exhaustion and restore anti-tumor immunity" J. Exp. Med. 207(10):2187-2194.
Sakuishi, K., et al., (2013) "TIM3+FOXP3+ regulatory T cells are tissue-specific promoters of T-cell dysfunction in cancer" Oncoimmunology. 2(4):e23849.
Severson, J.J., et al., (2015) "PD-1+Tim-3+ CD8+ T Lymphocytes Display Varied Degrees of Functional Exhaustion in Patients with Regionally Metastatic Differentiated Thyroid Cancer" Cancer Immunol Res; 3(6):620-30.
Shayan, G., et al., (2017) "Adaptive resistance to anti-PD1 therapy by Tim-3 upregulation is mediated by the PI3K-Akt pathway in head and neck cancer" OncoImmunology, 6(1):e1261779.
Shields, RL et al., (2001) "High Resolution Mapping of the Binding Site on Human Igg1 for Fc Gamma Ri, Fc Gamma Rii, Fc Gamma Riii, and Fcrn and Design of Igg1 Variants With Improved Binding to the Fc Gamma R" J Biol Chem 276: 6591-604.
Sledzinska, A., et al., (2015) "Negative immune checkpoints on T lymphocytes and their relevance to cancer immunotherapy" Mol. Oncol. 9:1936-65.
Tesaro: Abstract From "Tesaro and Anaptysbio Expand Immuno-Oncology Colloboration to Include Novel Bispecific Antibody Candidate", Dec. 2, 2014.
Thaventhiran, T., et al., (2012) "T Cell Co-inhibitory Receptors: Functions and Signalling Mechanisms" J Clin Cell Immunol S12:1-12.
Thommen, D.S., et al., (2015) "Progression of Lung Cancer Is Associated with Increased Dysfunction of T Cells Defined by Coexpression of Multiple Inhibitory Receptors" Cancer Immunol Res; 3(12); 1344-55.
Tieu, R., et al., (2014) "TIM-3, a Possible Target for Immunotherapy in Cancer and Chronic Viral Infections" Austin Virol. Retro Virol. 1(2):1-12.
Tiller, T., et al., (2013) "A fully synthetic human Fab antibody library based on fixed VH/VL framework pairings with favorable biophysical properties" MAbs 5(3):445-70.
Waight, J., et al., "INCAGN02390, a Novel Antagonist Antibody That Targets the Co-Inhibitory Receptor TIM-3" 3825 Presented at the American Association for Cancer Research 109th Annual Meeting Chicago, IL, USA, Apr. 14-18, 2018.
Xu, B., et al., (2015) "Circulating and tumor-infiltrating Tim-3 in patients with colorectal cancer" Oncotarget 6(24):20592-603.
Yan, J., et al., (2013) "Tim-3 expression defines regulatory T cells in human tumors" PLoS One 8(3):e58006.
Yang, Z., et al., (2012) "IL-12 upregulates TIM-3 expression and induces T cell exhaustion in patients with follicular B cell non-Hodgkin lymphoma" J. Clin. Invest. 122(4):1271-82.
Yin, W., et al., (2016) "Therapeutic HPV Cancer Vaccine Targeted to CD40 Elicits Effective CD8+ T-cell Immunity" Cancer Immunol Res. 4(10):823-834.
Zhang, Y., et al., (2017) "Co-expression of TIM-3 and CEACAM1 promotes T cell exhaustion in colorectal cancer patients" International Immunopharmacology 43:210-218.

(56) References Cited

OTHER PUBLICATIONS

Zhu, C., et al., (2015) "An IL-27/NFIL3 signaling axis drives Tim-3 and IL-10 expression and T-cell dysfunction" Nature Communications 6(6072):1-11.

Zhu, C., et al., (2015) "Corrigendum: An IL-27/NFIL3 signalling axis drives Tim-3 and IL-10 expression and T-cell dysfunction" Nature Communications 6:6072.

* cited by examiner

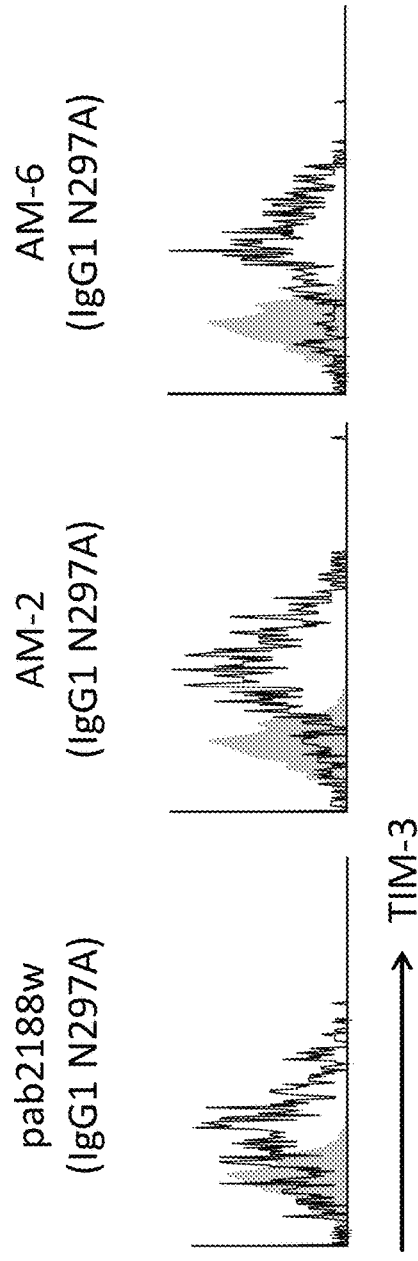
Figure 9C  Binding to SEA-stimulated human CD8+ T cells
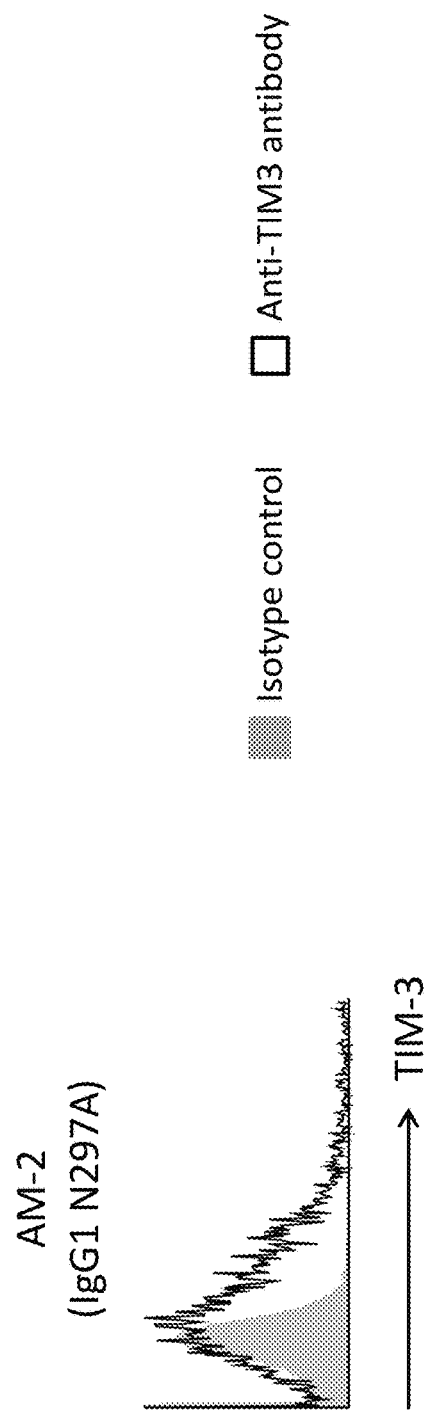
Figure 9D  Binding to SEA-stimulated cynomolgus CD8+ T cells

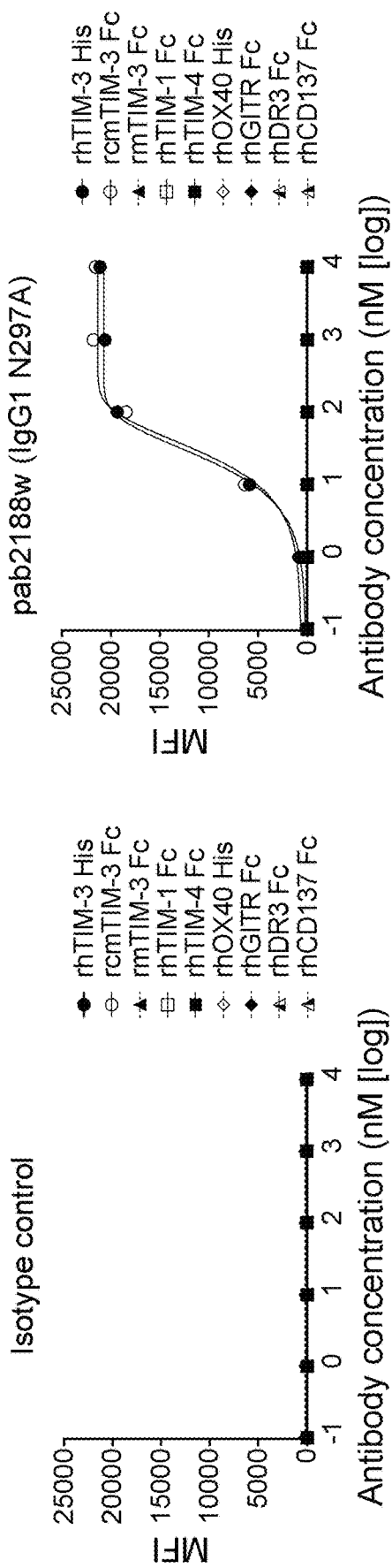
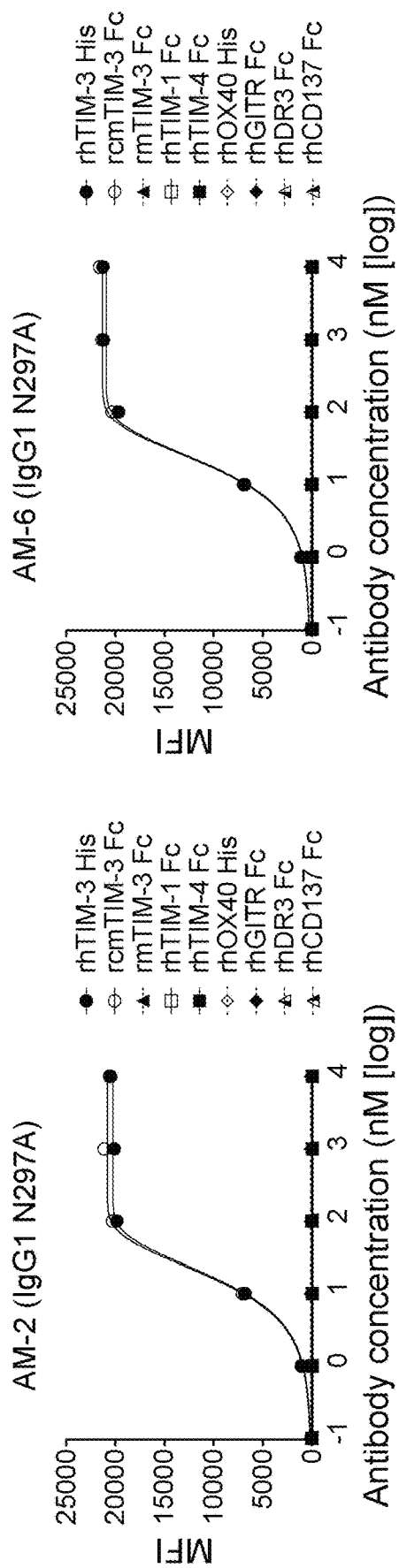
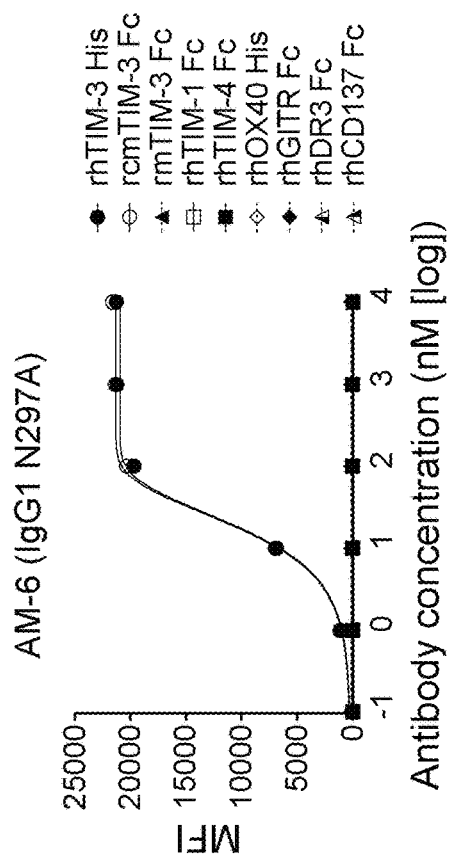
Figure 10A, Figure 10B, Figure 10C, Figure 10D

ANTI-TIM-3 ANTIBODIES AND METHODS OF USE THEREOF

RELATED APPLICATIONS

This application claims the benefit of U.S. Provisional Application Nos. 62/342,610, filed May 27, 2016; and 62/420,276, filed Nov. 10, 2016, each of which is incorporated by reference herein in its entirety.

1. FIELD

The instant disclosure relates to antibodies that specifically bind to TIM-3 (e.g., human TIM-3) and methods of using the same.

2. BACKGROUND

The protein T cell immunoglobulin and mucin domain-3 (TIM-3) is a type I membrane protein in the immunoglobulin (Ig) superfamily. It has an extracellular Ig variable-like (IgV) domain, an extracellular mucin-like domain, and a cytoplasmic domain with six conserved tyrosine residues (Monney et al. (2002) Nature 415:536-41). TIM-3 is expressed on activated T-helper type 1 (Th1) and $CD8^+$ T (Tc1) lymphocytes, some macrophages (Monney et al. (2002) Nature 415:536-41), activated natural killer (NK) cells (Ndhlovu et al. (2012) Blood 119(16):3734-43), and IL-17-producing Th17 cells (Nakae et al. (2007) J Leukoc Biol 81: 1258-68).

Studies have shown that TIM-3 functions to inhibit T cell, myeloid cell, and NK cell-mediated responses and to promote immunological tolerance. For example, TIM-3 IgV peptide fused with an immunoglobulin domain, which binds to and neutralizes TIM-3 ligands, caused hyperproliferation of Th1 cells and Th1 cytokine release in immunized mice (Sabatos et al. (2003) Nat Immunol 4:1102-10). Indeed, in vivo administration of an anti-TIM-3 antibody enhanced the pathological severity of experimental autoimmune encephalomyelitis, an animal model of multiple sclerosis (Monney et al. (2002) Nature 415:536-41). Moreover, TIM-3 expression is upregulated in $CD8^+$ T cells in cancer patients. For example, approximately 30% of NY-ESO-1-specific CD8+ T cells in patients with advanced melanoma exhibit upregulation of TIM-3 expression (Fourcade et al. (2010) J Exp Med 207:2175-86).

Given the apparent role of human TIM-3 in modulating immune responses, therapeutic agents designed to antagonize TIM-3 signaling hold great promise for the treatment of diseases that involve TIM-3-mediated immune suppression.

3. SUMMARY

The instant disclosure provides antibodies that specifically bind to TIM-3 (e.g., human TIM-3) and antagonize TIM-3 function, e.g., TIM-3-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen) and/or decreasing Treg-mediated immune suppression, and hence for treating cancer in a subject or treating or preventing an infectious disease in a subject.

Accordingly, in one aspect, the instant disclosure provides an antibody or isolated antibody comprising a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of $X_1X_2X_3X_4X_5S$ (SEQ ID NO: 48), wherein
  $X_1$ is R, S, A, G, K, M, or T,
  $X_2$ is Q, S, A, G, R, or T,
  $X_3$ is N, Y, G, or Q,
  $X_4$ is A or Q, and
  $X_5$ is W, M, A, S, or T;
(b) CDRH2 comprises the amino acid sequence of WVSAISGSGGSTY (SEQ ID NO: 2);
(c) CDRH3 comprises the amino acid sequence of AKGGDYGGNYFD (SEQ ID NO: 3);
(d) CDRL1 comprises the amino acid sequence of $X_1ASQSVX_2SSYLA$ (SEQ ID NO: 52),
  wherein
  $X_1$ is R or G, and
  $X_2$ is absent or S;
(e) CDRL2 comprises the amino acid sequence of $X_1ASX_2RAT$ (SEQ ID NO: 53), wherein
  $X_1$ is D or G, and
  $X_2$ is N, S, or T; and
(f) CDRL3 comprises the amino acid sequence of $QQYGSSPX_1T$ (SEQ ID NO: 54), wherein $X_1$ is L or I.

In another aspect, the instant disclosure provides an antibody or isolated antibody that specifically binds to human TIM-3, the antibody comprising a heavy chain variable region comprising complementarity determining regions CDRH1, CDRH2 and CDRH3 and a light chain variable region comprising complementarity determining regions CDRL1, CDRL2 and CDRL3, wherein:

(a) CDRH1 comprises the amino acid sequence of $X_1X_2X_3X_4X_5S$ (SEQ ID NO: 48), wherein
  $X_1$ is R, S, A, G, K, M, or T,
  $X_2$ is Q, S, A, G, R, or T,
  $X_3$ is N, Y, G, or Q,
  $X_4$ is A or Q, and
  $X_5$ is W, M, A, S, or T;
(b) CDRH2 comprises the amino acid sequence of WVSAISGSGGSTY (SEQ ID NO: 2);
(c) CDRH3 comprises the amino acid sequence of AKGGDYGGNYFD (SEQ ID NO: 3);
(d) CDRL1 comprises the amino acid sequence of $X_1ASQSVX_2SSYLA$ (SEQ ID NO: 52),
  wherein
  $X_1$ is R or G, and
  $X_2$ is absent or S;
(e) CDRL2 comprises the amino acid sequence of $X_1ASX_2RAT$ (SEQ ID NO: 53), wherein
  $X_1$ is D or G, and
  $X_2$ is N, S, or T; and
(f) CDRL3 comprises the amino acid sequence of $QQYGSSPX_1T$ (SEQ ID NO: 54),
  wherein $X_1$ is L or I.

In another aspect, the instant disclosure provides an antibody or isolated antibody comprising a heavy chain variable region having complementarity determining regions CDRH1, CDRH2 and CDRH3 and a light chain variable region having complementarity determining regions CDRL1, CDRL2 and CDRL3, wherein the antibody is internalized upon binding to cells expressing human TIM-3, and wherein CDRH3 comprises the amino acid sequence of AKGGDYGGNYFD (SEQ ID NO: 3).

In another aspect, the instant disclosure provides an antibody or isolated antibody that specifically binds to human TIM-3, the antibody comprising a heavy chain variable region having complementarity determining regions CDRH1, CDRH2 and CDRH3 and a light chain variable region having complementarity determining regions CDRL1, CDRL2 and CDRL3, wherein the antibody is internalized upon binding to cells expressing human TIM-3, and wherein CDRH3 comprises the amino acid sequence of AKGGDYGGNYFD (SEQ ID NO: 3).

In certain embodiments:
(a) CDRH1 comprises the amino acid sequence of $X_1X_2X_3X_4X_5S$ (SEQ ID NO: 48), wherein
   $X_1$ is R, S, A, G, K, M, or T,
   $X_2$ is Q, S, A, G, R, or T,
   $X_3$ is N, Y, G, or Q,
   $X_4$ is A or Q, and
   $X_5$ is W, M, A, S, or T;
(b) CDRH2 comprises the amino acid sequence of WVSAISGSGGSTY (SEQ ID NO: 2);
(c) CDRL1 comprises the amino acid sequence of $X_1ASQSVX_2SSYLA$ (SEQ ID NO: 52), wherein
   $X_1$ is R or G, and
   $X_2$ is absent or S;
(d) CDRL2 comprises the amino acid sequence of $X_1ASX_2RAT$ (SEQ ID NO: 53), wherein
   $X_1$ is D or G, and
   $X_2$ is N, S, or T; and
(e) CDRL3 comprises the amino acid sequence of $QQYGSSPX_1T$ (SEQ ID NO: 54),
   wherein $X_1$ is L or I.

In certain embodiments, CDRH1 comprises the amino acid sequence of $X_1X_2NAWS$ (SEQ ID NO: 49), wherein: $X_1$ is R or A; and $X_2$ is Q or R. In certain embodiments, CDRH1 comprises the amino acid sequence of $X_1X_2GQX_3S$ (SEQ ID NO: 50), wherein: $X_1$ is K, M, or G; $X_2$ is A or S; and $X_3$ is S or T. In certain embodiments, CDRH1 comprises the amino acid sequence of $X_1X_2QQAS$ (SEQ ID NO: 51), wherein: $X_1$ is S, R, T, or G; and $X_2$ is A, S, T, or G. In certain embodiments, CDRH1 comprises an amino acid sequence selected from the group consisting of SEQ ID NOs: 1 and 4-12.

In certain embodiments, CDRL1 comprises an amino acid sequence selected from the group consisting of SEQ ID NOs: 13-16. In certain embodiments, CDRL2 comprises an amino acid sequence selected from the group consisting of SEQ ID NOs: 17-21. In certain embodiments, CDRL3 comprises an amino acid sequence selected from the group consisting of SEQ ID NOs: 22 and 23.

In certain embodiments, CDRH1, CDRH2 and CDRH3 comprise the CDRH1, CDRH2 and CDRH3 amino acid sequences, respectively, set forth in SEQ ID NOs: 1, 2, and 3; 4, 2, and 3; 5, 2, and 3; 6, 2, and 3; 7, 2, and 3; 8, 2, and 3; 9, 2, and 3; 10, 2, and 3; 11, 2, and 3; or 12, 2, and 3.

In certain embodiments, CDRL1, CDRL2 and CDRL3 comprise the CDRL1, CDRL2 and CDRL3 amino acid sequences, respectively, set forth in SEQ ID NOs: 13, 17, and 22; 14, 17, and 22; 15, 18, and 22; 14, 19, and 22; 14, 20, and 22; 14, 21, and 22; 16, 20, and 22; or 14, 17, and 23.

In certain embodiments, CDRH1, CDRH2, CDRH3, CDRL1, CDRL2, and CDRL3 comprise the amino acid sequences set forth in SEQ ID NOs: 1, 2, 3, 14, 21, and 22; 4, 2, 3, 14, 21, and 22; 5, 2, 3, 14, 21, and 22; 6, 2, 3, 14, 21, and 22; 7, 2, 3, 14, 21, and 22; 8, 2, 3, 14, 21, and 22; 9, 2, 3, 14, 21, and 22; 10, 2, 3, 14, 21, and 22; 11, 2, 3, 14, 21, and 22; or 12, 2, 3, 14, 21, and 22, respectively.

In another aspect, the instant disclosure provides an antibody or isolated antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 14, 21, and 22, respectively.

In another aspect, the instant disclosure provides an antibody or isolated antibody that specifically binds to human TIM-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 14, 21, and 22, respectively.

In another aspect, the instant disclosure provides an antibody or isolated antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 5, 2, 3, 14, 21, and 22, respectively.

In another aspect, the instant disclosure provides an antibody or isolated antibody that specifically binds to human TIM-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 5, 2, 3, 14, 21, and 22, respectively.

In another aspect, the instant disclosure provides an antibody or isolated antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 9, 2, 3, 14, 21, and 22, respectively.

In another aspect, the instant disclosure provides an antibody or isolated antibody that specifically binds to human TIM-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 9, 2, 3, 14, 21, and 22, respectively.

In another aspect, the instant disclosure provides an antibody or isolated comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 15, 18, and 22, respectively.

In another aspect, the instant disclosure provides an antibody or isolated antibody that specifically binds to human TIM-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 15, 18, and 22, respectively.

In certain embodiments, the antibody is internalized upon binding to cells expressing human TIM-3.

In another aspect, the instant disclosure provides an antibody or isolated antibody that specifically binds to human TIM-3, wherein the antibody is internalized upon binding to cells expressing human TIM-3.

In certain embodiments, a lower percentage of the cells expressing human TIM-3 survive in the presence of the antibody than in the presence of pab1944w (IgG$_1$ N297A) in an assay comprising the following steps: (a) plating the cells expressing human TIM-3 at 2×10$^4$ cells per well in a tissue culture plate; (b) adding 1111 ng/ml of αHFc-NC-DM1 and 1111 ng/ml of the antibody or pab1944w (IgG$_1$ N297A) at a final volume of 100 µl/well; (c) incubating at 37° C. and 5% CO$_2$ for 72 hours; (d) measuring survival of the cells expressing human TIM-3; and (e) calculating percentage of cell survival relative to untreated cells expressing human TIM-3. In certain embodiments, the percentage of cell survival in the presence of the antibody is at least 50% lower than the percentage of cell survival in the presence of pab1944w (IgG$_1$ N297A). In certain embodiments, the cells expressing human TIM-3 are Kasumi-3 cells. In certain embodiments, the cells expressing human TIM-3 are Kasumi-3 cells (ATCC® CRL-2725™). In certain embodiments, the cells expressing human TIM-3 are Jurkat cells engineered to express human TIM-3.

In certain embodiments, a lower percentage of the cells expressing human TIM-3 survive in the presence of the antibody than in the presence of Hum11 (IgG$_4$ S228P) in an assay comprising the following steps: (a) plating the cells expressing human TIM-3 at 2×10$^4$ cells per well in a tissue culture plate; (b) adding 1111 ng/ml of αHFc-NC-DM1 and 1111 ng/ml of the antibody or Hum11 (IgG$_4$ S228P) at a final volume of 100 µl/well; (c) incubating at 37° C. and 5% CO$_2$ for 72 hours; (d) measuring survival of the cells expressing human TIM-3; and (e) calculating percentage of cell survival relative to untreated cells expressing human TIM-3. In certain embodiments, the percentage of cell survival in the presence of the antibody is at least 50% lower than the percentage of cell survival in the presence of Hum11 (IgG$_4$ S228P). In certain embodiments, the cells expressing human TIM-3 are Kasumi-3 cells. In certain embodiments, the cells expressing human TIM-3 are Kasumi-3 cells (ATCC® CRL-2725™). In certain embodiments, the cells expressing human TIM-3 are Jurkat cells engineered to express human TIM-3.

In certain embodiments, the antibody comprises a heavy chain variable region comprising the amino acid sequence of SEQ ID NO: 55. In certain embodiments, the antibody comprises a heavy chain variable region comprising an amino acid sequence which is at least 75%, 80%, 85%, 90%, 95%, or 100% identical to an amino acid sequence selected from the group consisting of SEQ ID NOs: 24-35. In certain embodiments, the heavy chain variable region comprises an amino acid sequence selected from the group consisting of SEQ ID NOs: 24-35. In certain embodiments, the heavy chain variable region comprises the amino acid sequence of SEQ ID NO: 25. In certain embodiments, the heavy chain variable region comprises the amino acid sequence of SEQ ID NO: 28. In certain embodiments, the heavy chain variable region comprises the amino acid sequence of SEQ ID NO: 32. In certain embodiments, the N-terminal glutamate (E) residue of a heavy chain variable region of an antibody as described herein is replaced with a pyroglutamate (pE) residue.

In certain embodiments, the antibody comprises a light chain variable region comprising the amino acid sequence of SEQ ID NO: 56. In certain embodiments, the antibody comprises a light chain variable region comprising an amino acid sequence which is at least 75%, 80%, 85%, 90%, 95%, or 100% identical to an amino acid sequence selected from the group consisting of SEQ ID NOs: 36-47. In certain embodiments, the light chain variable region comprises an amino acid sequence selected from the group consisting of SEQ ID NOs: 36-47. In certain embodiments, the light chain variable region comprises the amino acid sequence of SEQ ID NO: 46. In certain embodiments, the N-terminal glutamate (E) residue of a light chain variable region of an antibody as described herein is replaced with a pyroglutamate (pE) residue.

In another aspect, the instant disclosure provides an antibody or isolated antibody comprising a heavy chain variable region comprising an amino acid sequence selected from the group consisting of SEQ ID NOs: 24-35. In certain embodiments, the heavy chain variable region comprises the amino acid sequence of SEQ ID NO: 25. In certain embodiments, the heavy chain variable region comprises the amino acid sequence of SEQ ID NO: 28. In certain embodiments, the heavy chain variable region comprises the amino acid sequence of SEQ ID NO: 32. In certain embodiments, the antibody comprises a heavy chain comprising the amino acid sequence of SEQ ID NO: 58. In certain embodiments, the antibody comprises a heavy chain comprising the amino acid sequence of SEQ ID NO: 61. In certain embodiments, the antibody comprises a heavy chain comprising the amino acid sequence of SEQ ID NO: 65. In certain embodiments, the antibody comprises a heavy chain comprising the amino acid sequence of SEQ ID NO: 70, 71, 72, 73, 74 or 75. In certain embodiments, the N-terminal glutamate (E) residue of a heavy chain of an antibody as described herein is replaced with a pyroglutamate (pE) residue.

In another aspect, the instant disclosure provides an antibody or isolated antibody that specifically binds to human TIM-3, the antibody comprising a heavy chain variable region comprising an amino acid sequence selected from the group consisting of SEQ ID NOs: 24-35. In certain embodiments, the heavy chain variable region comprises the amino acid sequence of SEQ ID NO: 25. In certain embodiments, the heavy chain variable region comprises the amino acid sequence of SEQ ID NO: 28. In certain embodiments, the heavy chain variable region comprises the amino acid sequence of SEQ ID NO: 32. In certain embodiments, the antibody comprises a heavy chain comprising the amino acid sequence of SEQ ID NO: 58. In certain embodiments, the antibody comprises a heavy chain comprising the amino acid sequence of SEQ ID NO: 61. In certain embodiments, the antibody comprises a heavy chain comprising the amino acid sequence of SEQ ID NO: 65. In certain embodiments, the antibody comprises a heavy chain comprising the amino acid sequence of SEQ ID NO: 70, 71, 72, 73, 74 or 75.

In another aspect, the instant disclosure provides an antibody or isolated antibody comprising a light chain variable region comprising an amino acid sequence selected from the group consisting of SEQ ID NOs: 36-47. In certain embodiments, the light chain variable region comprises the amino acid sequence of SEQ ID NO: 46. In certain embodiments, the antibody comprises a light chain comprising the amino acid sequence of SEQ ID NO: 69. In certain embodiments, the antibody comprises a light chain comprising the amino acid sequence of SEQ ID NO: 76 or 77. In certain embodiments, the N-terminal glutamate (E) residue of a light chain of an antibody as described herein is replaced with a pyroglutamate (pE) residue.

In another aspect, the instant disclosure provides an antibody or isolated antibody that specifically binds to human TIM-3, the antibody comprising a light chain variable region comprising an amino acid sequence selected from the group consisting of SEQ ID NOs: 36-47. In certain embodiments, the light chain variable region comprises the amino acid sequence of SEQ ID NO: 46. In certain embodiments, the antibody comprises a light chain comprising the amino acid sequence of SEQ ID NO: 69. In certain embodiments, the antibody comprises a light chain comprising the amino acid sequence of SEQ ID NO: 76 or 77.

In another aspect, the instant disclosure provides an antibody or isolated antibody comprising a heavy chain variable region and a light chain variable region, wherein the heavy chain variable region and the light chain variable region, respectively, comprise the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46. In certain embodiments, the heavy chain variable region and the light chain variable region, respectively, comprise the amino acid sequences set forth in SEQ ID NOs: 25 and 46. In certain embodiments, the heavy chain variable region and the light chain variable region, respectively, comprise the amino acid sequences set forth in SEQ ID NOs: 28 and 46. In certain embodiments, the heavy chain variable region and the light chain variable region, respectively, comprise the amino acid sequences set forth in SEQ ID NOs: 32 and 46. In certain embodiments, the N-terminal glutamate (E) residue of a heavy chain variable region of an antibody as described herein is replaced with a pyroglutamate (pE) residue and/or the N-terminal glutamate (E) residue of a light chain variable region of the antibody is replaced with a pyroglutamate (pE) residue.

In another aspect, the instant disclosure provides an antibody or isolated antibody comprising a heavy chain variable region and a light chain variable region, wherein the amino acid sequences of the heavy chain variable region and the light chain variable region, respectively, consist of the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46. In certain embodiments, the amino acid sequences of the heavy chain variable region and the light chain variable region, respectively, consist of the amino acid sequences set forth in SEQ ID NOs: 25 and 46. In certain embodiments, the amino acid sequences of the heavy chain variable region and the light chain variable region, respectively, consist of the amino acid sequences set forth in SEQ ID NOs: 28 and 46. In certain embodiments, the amino acid sequences of the heavy chain variable region and the light chain variable region, respectively, consist of the amino acid sequences set forth in SEQ ID NOs: 32 and 46.

In another aspect, the instant disclosure provides an antibody or isolated antibody that specifically binds to human TIM-3, the antibody comprising a heavy chain variable region and a light chain variable region, wherein the heavy chain variable region and the light chain variable region, respectively, comprise the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46. In certain embodiments, the heavy chain variable region and the light chain variable region, respectively, comprise the amino acid sequences set forth in SEQ ID NOs: 25 and 46. In certain embodiments, the heavy chain variable region and the light chain variable region, respectively, comprise the amino acid sequences set forth in SEQ ID NOs: 28 and 46. In certain embodiments, the heavy chain variable region and the light chain variable region, respectively, comprise the amino acid sequences set forth in SEQ ID NOs: 32 and 46.

In another aspect, the instant disclosure provides an antibody or isolated antibody that specifically binds to human TIM-3, the antibody comprising a heavy chain variable region and a light chain variable region, wherein the amino acid sequences of the heavy chain variable region and the light chain variable region, respectively, consist of the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46. In certain embodiments, the amino acid sequences of the heavy chain variable region and the light chain variable region, respectively, consist of the amino acid sequences set forth in SEQ ID NOs: 25 and 46. In certain embodiments, the amino acid sequences of the heavy chain variable region and the light chain variable region, respectively, consist of the amino acid sequences set forth in SEQ ID NOs: 28 and 46. In certain embodiments, the amino acid sequences of the heavy chain variable region and the light chain variable region, respectively, consist of the amino acid sequences set forth in SEQ ID NOs: 32 and 46.

In another aspect, the instant disclosure provides an antibody or isolated antibody comprising a heavy chain comprising the amino acid sequence of SEQ ID NO: 58, and a light chain comprising the amino acid sequence of SEQ ID NO: 69.

In another aspect, the instant disclosure provides an antibody or isolated antibody that specifically binds to human TIM-3, the antibody comprising a heavy chain comprising the amino acid sequence of SEQ ID NO: 58, and a light chain comprising the amino acid sequence of SEQ ID NO: 69.

In another aspect, the instant disclosure provides an antibody or isolated antibody comprising a heavy chain comprising the amino acid sequence of SEQ ID NO: 61, and a light chain comprising the amino acid sequence of SEQ ID NO: 69.

In another aspect, the instant disclosure provides an antibody or isolated antibody that specifically binds to human TIM-3, the antibody comprising a heavy chain comprising the amino acid sequence of SEQ ID NO: 61, and a light chain comprising the amino acid sequence of SEQ ID NO: 69.

In another aspect, the instant disclosure provides an antibody or isolated antibody comprising a heavy chain comprising the amino acid sequence of SEQ ID NO: 65, and a light chain comprising the amino acid sequence of SEQ ID NO: 69.

In another aspect, the instant disclosure provides an antibody or isolated antibody that specifically binds to human TIM-3, the antibody comprising a heavy chain comprising the amino acid sequence of SEQ ID NO: 65, and a light chain comprising the amino acid sequence of SEQ ID NO: 69.

In certain embodiments, the N-terminal glutamate (E) residue of a heavy chain of an antibody as described herein is replaced with a pyroglutamate (pE) residue and/or the N-terminal glutamate (E) residue of a light chain of the antibody is replaced with a pyroglutamate (pE) residue.

In certain embodiments, the antibody comprises a heavy chain variable region having an amino acid sequence derived from a human IGHV3-23 germline sequence. In certain embodiments, the antibody comprises a light chain variable region having an amino acid sequence derived from a human germline sequence selected from the group consisting of IGKV1-27, IGKV3-11, IGKV3-20, and IGKV3D-20.

In another aspect, the instant disclosure provides an antibody or isolated antibody that specifically binds to human TIM-3, the antibody comprising a heavy chain variable region having an amino acid sequence derived from a human IGHV3-23 germline sequence, and a light chain variable region having an amino acid sequence derived from a human germline sequence selected from the group consisting of IGKV1-27, IGKV3-11, IGKV3-20, and IGKV3D-20.

In certain embodiments, the antibody comprises a heavy chain constant region selected from the group consisting of human IgG$_1$, IgG$_2$, IgG$_3$, IgG$_4$, IgA$_1$, and IgA$_2$. In certain embodiments, the heavy chain constant region is IgG$_1$. In certain embodiments, the amino acid sequence of IgG$_1$ comprises a N297A mutation, numbered according to the EU numbering system. In certain embodiments, the antibody comprises a heavy chain constant region comprising the amino acid sequence of SEQ ID NO: 72. In certain embodiments, the amino acid sequence of IgG$_1$ comprises a N297Q mutation, numbered according to the EU numbering system. In certain embodiments, the IgG$_1$ is non-fucosylated IgG$_1$. In certain embodiments, the heavy chain constant region is IgG$_4$. In certain embodiments, the amino acid sequence of IgG$_4$ comprises a S228P mutation, numbered according to the EU numbering system. In certain embodiments, the antibody comprises a heavy chain constant region comprising the amino acid sequence of SEQ ID NO: 74.

In certain embodiments, the antibody comprises a light chain constant region selected from the group consisting of human IgGκ and IgGλ. In certain embodiments, the light chain constant region is IgGκ. In certain embodiments, the antibody comprises a light chain constant region comprising the amino acid sequence of SEQ ID NO: 76. In certain embodiments, the light chain constant region is IgGλ.

In another aspect, the instant disclosure provides an antibody or isolated antibody that cross-competes for binding to human TIM-3 with an antibody as disclosed herein. In certain embodiments, the instant disclosure provides an antibody or isolated antibody that cross-competes for binding to human TIM-3 with an antibody comprising the heavy and light chain variable region amino acid sequences set forth in SEQ ID NOs: 55 and 56, respectively. In certain embodiments, the instant disclosure provides an antibody or isolated antibody that cross-competes for binding to human TIM-3 with an antibody comprising the heavy and light chain variable region amino acid sequences set forth in SEQ ID NOs: 25 and 46, respectively. In certain embodiments, the instant disclosure provides an antibody or isolated antibody that cross-competes for binding to human TIM-3 with an antibody comprising the heavy and light chain variable region amino acid sequences set forth in SEQ ID NOs: 28 and 46, respectively. In certain embodiments, the instant disclosure provides an antibody or isolated antibody that cross-competes for binding to human TIM-3 with an antibody comprising the heavy and light chain variable region amino acid sequences set forth in SEQ ID NOs: 32 and 46, respectively.

In another aspect, the instant disclosure provides an antibody or isolated antibody that binds to the same epitope of human TIM-3 as an antibody disclosed herein. In certain embodiments, the instant disclosure provides an antibody or isolated antibody that binds to the same epitope of human TIM-3 as an antibody comprising the heavy and light chain variable region amino acid sequences set forth in SEQ ID NOs: 55 and 56, respectively. In certain embodiments, the instant disclosure provides an antibody or isolated antibody that binds to the same epitope of human TIM-3 as an antibody comprising the heavy and light chain variable region amino acid sequences set forth in SEQ ID NOs: 25 and 46, respectively. In certain embodiments, the instant disclosure provides an antibody or isolated antibody that binds to the same epitope of human TIM-3 as an antibody comprising the heavy and light chain variable region amino acid sequences set forth in SEQ ID NOs: 28 and 46, respectively. In certain embodiments, the instant disclosure provides an antibody or isolated antibody that binds to the same epitope of human TIM-3 as an antibody comprising the heavy and light chain variable region amino acid sequences set forth in SEQ ID NOs: 32 and 46, respectively.

In another aspect, the instant disclosure provides an antibody or isolated antibody that specifically binds to human TIM-3, wherein the antibody specifically binds to a variant TIM-3 protein having the amino acid sequence of SEQ ID NO: 101 with a lower affinity than to a wild-type TIM-3 protein having the amino acid sequence of SEQ ID NO: 79.

In another aspect, the instant disclosure provides an antibody or isolated antibody that specifically binds to the same epitope of human TIM-3 as any antibody of the present invention. In one embodiment, the antibody specifically binds to a variant TIM-3 protein having the amino acid sequence of SEQ ID NO: 101 with a lower affinity than to a wild-type TIM-3 protein having the amino acid sequence of SEQ ID NO: 79.

In another aspect, the instant disclosure provides an antibody or isolated antibody that specifically binds to human TIM-3, wherein the antibody does not specifically bind to a variant TIM-3 protein having the amino acid sequence of SEQ ID NO: 101.

In another aspect, the instant disclosure provides an antibody or isolated antibody that specifically binds to the same epitope of human TIM-3 as any antibody of the present invention. In one embodiment, the antibody does not specifically bind to a variant TIM-3 protein having the amino acid sequence of SEQ ID NO: 101.

In another aspect, the instant disclosure provides an antibody or isolated antibody that specifically binds to human TIM-3, wherein the binding between the antibody and a variant TIM-3 protein having the amino acid sequence of SEQ ID NO: 101 is substantially weakened relative to the binding between the antibody and a wild-type TIM-3 protein having the amino acid sequence of SEQ ID NO: 79.

In another aspect, the instant disclosure provides an antibody or isolated antibody that specifically binds to the same epitope of human TIM-3 as any antibody of the present invention. In one embodiment, the binding between the antibody and a variant TIM-3 protein having the amino acid sequence of SEQ ID NO: 101 is substantially weakened relative to the binding between the antibody and a wild-type TIM-3 protein having the amino acid sequence of SEQ ID NO: 79.

In another aspect, the instant disclosure provides an antibody or isolated antibody that specifically binds to human TIM-3, wherein the antibody exhibits, as compared to binding to a wild-type TIM-3 protein having the amino acid sequence of SEQ ID NO: 79, reduced or absent binding to a variant TIM-3 protein having the amino acid sequence of SEQ ID NO: 101.

In another aspect, the instant disclosure provides an antibody or isolated antibody that specifically binds to the same epitope of human TIM-3 as any antibody of the present invention. In one embodiment, the antibody exhibits, as compared to binding to a wild-type TIM-3 protein having the amino acid sequence of SEQ ID NO: 79, reduced or absent binding to a variant TIM-3 protein having the amino acid sequence of SEQ ID NO: 101.

In another aspect, the instant disclosure provides an antibody or isolated antibody that binds, e.g., specifically binds, to an epitope of human TIM-3. In certain embodiments, the antibody binds to residue 40 of SEQ ID NO: 79.

In another aspect, the instant disclosure provides an antibody or isolated antibody that specifically binds to the same epitope of human TIM-3 as any antibody of the present invention. In certain embodiments, the antibody binds to residue 40 of SEQ ID NO: 79.

In another aspect, the instant disclosure provides an antibody or isolated antibody that binds, e.g., specifically binds, to an epitope of human TIM-3. In certain embodiments, the antibody binds to an epitope located within a region of human TIM-3 consisting of the amino acid sequence of SEQ ID NO: 93. In certain embodiments, the antibody binds to an epitope located within a region of human TIM-3 consisting of the amino acid sequence of SEQ ID NO: 94. In certain embodiments, the antibody binds to an epitope located within a region of human TIM-3 consisting of the amino acid sequence of SEQ ID NO: 95. In certain embodiments, the antibody binds to an epitope located within a region of human TIM-3 consisting of the amino acid sequence of SEQ ID NO: 96. In certain embodiments, the antibody binds to an epitope located within a region of human TIM-3 consisting of the amino acid sequence of SEQ ID NO: 97. In certain embodiments, the antibody binds to an epitope located within a region of human TIM-3 consisting of the amino acid sequence of SEQ ID NO: 98. In certain embodiments, the antibody binds to an epitope located within a region of human TIM-3 consisting of the amino acid sequence of SEQ ID NO: 99. In certain embodiments, the antibody binds to an epitope located within a region of human TIM-3 consisting of the amino acid sequence of SEQ ID NO: 100.

In another aspect, the instant disclosure provides an antibody or isolated antibody that specifically binds to the same epitope of human TIM-3 as any antibody of the present invention. In certain embodiments, the antibody binds to an epitope located within a region of human TIM-3 consisting of the amino acid sequence of SEQ ID NO: 93. In certain embodiments, the antibody binds to an epitope located within a region of human TIM-3 consisting of the amino acid sequence of SEQ ID NO: 94. In certain embodiments, the antibody binds to an epitope located within a region of human TIM-3 consisting of the amino acid sequence of SEQ ID NO: 95. In certain embodiments, the antibody binds to an epitope located within a region of human TIM-3 consisting of the amino acid sequence of SEQ ID NO: 96. In certain embodiments, the antibody binds to an epitope located within a region of human TIM-3 consisting of the amino acid sequence of SEQ ID NO: 97. In certain embodiments, the antibody binds to an epitope located within a region of human TIM-3 consisting of the amino acid sequence of SEQ ID NO: 98. In certain embodiments, the antibody binds to an epitope located within a region of human TIM-3 consisting of the amino acid sequence of SEQ ID NO: 99. In certain embodiments, the antibody binds to an epitope located within a region of human TIM-3 consisting of the amino acid sequence of SEQ ID NO: 100.

In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 93 relative to hydrogen/deuterium exchange in the region consisting of the amino acid sequence set forth in SEQ ID NO: 93 in the absence of the antibody, as determined by a hydrogen/deuterium assay. In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 94 relative to hydrogen/deuterium exchange in the region consisting of the amino acid sequence set forth in SEQ ID NO: 94 in the absence of the antibody, as determined by a hydrogen/deuterium assay. In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 95 relative to hydrogen/deuterium exchange in the region consisting of the amino acid sequence set forth in SEQ ID NO: 95 in the absence of the antibody, as determined by a hydrogen/deuterium assay. In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 96 relative to hydrogen/deuterium exchange in the region consisting of the amino acid sequence set forth in SEQ ID NO: 96 in the absence of the antibody, as determined by a hydrogen/deuterium assay. In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 97 relative to hydrogen/deuterium exchange in the region consisting of the amino acid sequence set forth in SEQ ID NO: 97 in the absence of the antibody, as determined by a hydrogen/deuterium assay. In another aspect, the instant disclosure provides an antibody that, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 98 relative to hydrogen/deuterium exchange in the region consisting of the amino acid sequence set forth in SEQ ID NO: 98 in the absence of the antibody, as determined by a hydrogen/deuterium assay. In some embodiments, the reduction in hydrogen/deuterium exchange is measured using hydrogen-deuterium exchange (HDX), for example as described herein in the examples.

In another aspect, the instant disclosure provides an antibody or isolated antibody that specifically binds to the same epitope of human TIM-3 as any antibody of the present invention. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 93 relative to hydrogen/deuterium exchange in the region consisting of the amino acid sequence set forth in SEQ ID NO: 93 in the absence of the antibody, as determined by a hydrogen/deuterium assay. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 94 relative to hydrogen/deuterium exchange in the region consisting of the amino acid sequence set forth in SEQ ID NO: 94 in the absence of the antibody, as determined by a hydrogen/deuterium assay. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 95 relative to hydrogen/deuterium exchange in the region consisting of the amino acid sequence set forth in SEQ ID NO: 95 in the absence of the antibody, as determined by a hydrogen/deuterium assay. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 96 relative to hydrogen/deuterium exchange in the region consisting of the amino acid sequence set forth in SEQ ID NO: 96 in the absence of the antibody, as determined by a hydrogen/deuterium assay. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 97 relative to hydrogen/deuterium exchange in the region consisting of the amino acid sequence set forth in SEQ ID NO: 97 in the absence of the antibody, as determined by a hydrogen/deuterium assay. In certain embodiments, the antibody, when bound to a human TIM-3 protein or fragment thereof comprising the amino acid sequence of SEQ ID NO: 102, reduces hydrogen/deuterium exchange in a region consisting of the amino acid sequence set forth in SEQ ID NO: 98 relative to hydrogen/deuterium exchange in the region consisting of the amino acid sequence set forth in SEQ ID NO: 98 in the absence of the antibody, as determined by a hydrogen/deuterium assay. In some embodiments, the reduction in hydrogen/deuterium exchange is measured using hydrogen-deuterium exchange (HDX), for example as described herein in the examples.

In another aspect, the instant disclosure provides an antibody or isolated antibody that binds, e.g., specifically binds, to the same epitope of human TIM-3 as any antibody of the present invention, wherein the epitope is determined by hydrogen-deuterium exchange (HDX), for example as described in the examples, by Pepscan analysis, for example as described in the examples, or by Alanine scanning, for example as described in the examples.

In certain embodiments, the antibody comprises a human IgG heavy chain constant region that is a variant of a wild type human IgG heavy chain constant region, wherein the variant human IgG heavy chain constant region binds to a human Fc gamma receptor with lower affinity than the wild type human IgG heavy chain constant region binds to the human Fc gamma receptor. In certain embodiments, the human Fc gamma receptor is selected from the group consisting of FcγRI, FcγRII, and FcγRIII. In certain embodiments, the variant human IgG heavy chain constant region is an IgG$_1$ constant region comprising a N297A mutation.

In certain embodiments, the antibody is a human antibody. In certain embodiments, the antibody is antagonistic to human TIM-3. In certain embodiments, the antibody deactivates, reduces, or inhibits an activity of human TIM-3. In certain embodiments, the antibody inhibits binding of human TIM-3 to phosphatidylserine. In certain embodiments, the antibody induces IFNγ production by peripheral blood mononuclear cells (PBMCs) stimulated with staphylococcal enterotoxin A (SEA). In certain embodiments, the antibody induces IFNγ or TNFα production by tumor infiltrating lymphocytes (TILs) stimulated with anti-CD3 and anti-CD28 antibodies.

In certain embodiments, the antibody is internalized upon binding to cells expressing human TIM-3.

In another aspect, the instant disclosure provides an antibody or isolated antibody as disclosed herein conjugated to a cytotoxic agent.

In another aspect, the instant disclosure provides an antibody or isolated antibody as disclosed herein conjugated to a cytostatic agent.

In another aspect, the instant disclosure provides an antibody or isolated antibody as disclosed herein conjugated to a toxin.

In another aspect, the instant disclosure provides an antibody or isolated antibody as disclosed herein conjugated to a radionuclide.

In another aspect, the instant disclosure provides an antibody or isolated antibody as disclosed herein conjugated to a detectable label.

In another aspect, the instant disclosure provides a pharmaceutical composition comprising an antibody as disclosed herein and a pharmaceutically acceptable carrier or excipient.

In another aspect, the instant disclosure provides a polynucleotide or isolated polynucleotide encoding a heavy and/or light chain of an antibody as disclosed herein. In another aspect, the instant disclosure provides a vector comprising the polynucleotide. In another aspect, the instant disclosure provides a recombinant host cell comprising the polynucleotide. In another aspect, the instant disclosure provides a recombinant host cell comprising the vector. In another aspect, the instant disclosure provides a method of producing an antibody as disclosed herein, the method comprising culturing the host cell so that the polynucleotide is expressed and the antibody is produced. In one embodiment, the method is an in vitro method.

In one embodiment, the present invention relates to an antibody of the invention, or a pharmaceutical composition of the invention, or a polynucleotide of the invention, or a vector of the invention, or a recombinant host cell of the invention for use as a medicament.

In one embodiment, the present invention relates to an antibody of the invention, or a pharmaceutical composition of the invention, or a polynucleotide of the invention, or a vector of the invention, or a recombinant host cell of the invention for use as a diagnostic.

In another aspect, the instant disclosure provides a method of increasing T cell activation in response to an antigen in a subject, the method comprising administering to the subject an effective amount of an antibody or pharmaceutical composition as disclosed herein. In another aspect, the instant disclosure provides a method of treating cancer in a subject, the method comprising administering to the subject an effective amount of an antibody or pharmaceutical composition as disclosed herein. In certain embodiments of the foregoing methods, the antibody or pharmaceutical composition is administered subcutaneously. In certain embodiments of the foregoing methods, the antibody or pharmaceutical composition is administered intravenously. In certain embodiments of the foregoing methods, the antibody or pharmaceutical composition is administered intratumorally. In certain embodiments of the foregoing methods, the antibody or pharmaceutical composition is delivered to a tumor draining lymph node. In certain embodiments of the foregoing methods, the antibody or pharmaceutical composition is administered intra-arterially.

In one aspect, the present invention relates to an antibody, polynucleotide, vector, recombinant host cell, and/or pharmaceutical composition of the present invention for use in a method for increasing T cell activation in response to an antigen.

In one aspect, the present invention relates to an antibody, polynucleotide, vector, recombinant host cell, and/or pharmaceutical composition of the present invention for use in a method for increasing T cell activation in response to an antigen in a subject.

In one aspect, the present invention relates to an antibody, polynucleotide, vector, recombinant host cell, and/or pharmaceutical composition of the present invention for use in a method for increasing T cell activation in response to an antigen in a subject comprising administering to the subject an effective amount of an antibody, polynucleotide, vector, recombinant host cell, and/or pharmaceutical composition of the invention.

In one aspect, the present invention relates to an antibody, polynucleotide, vector, recombinant host cell, and/or pharmaceutical composition of the present invention for use in a method for the treatment of cancer.

In one aspect, the present invention relates to an antibody, polynucleotide, vector, recombinant host cell, and/or pharmaceutical composition of the present invention for use in a method for the treatment of cancer in a subject.

In one aspect, the present invention relates to an antibody, polynucleotide, vector, recombinant host cell, and/or pharmaceutical composition of the present invention for use in a method for the treatment of cancer in a subject comprising administering to the subject an effective amount of an antibody, polynucleotide, vector, recombinant host cell, and/or pharmaceutical composition of the invention.

In one embodiment of an antibody, polynucleotide, vector, recombinant host cell, and/or pharmaceutical composition for use of the present invention, the antibody, polynucleotide, vector, recombinant host cell, and/or pharmaceutical composition is administered subcutaneously or intravenously. In another embodiment of an antibody, polynucleotide, vector, recombinant host cell, and/or pharmaceutical composition for use of the present invention, the antibody, polynucleotide, vector, recombinant host cell, and/or pharmaceutical composition is administered intratumorally or intra-arterially.

In certain embodiments, the foregoing methods further comprise administering an additional therapeutic agent to the subject. Therefore, in one embodiment of an antibody, polynucleotide, vector, recombinant host cell, and/or pharmaceutical composition for use in a method of the present invention, the method further comprises administering an additional therapeutic agent to the subject.

In one aspect, the present invention relates to (a) an antibody, polynucleotide, vector, recombinant host cell, and/or pharmaceutical composition of the present invention and (b) an additional therapeutic agent for use as a medicament.

In one aspect, the present invention relates to (a) an antibody, polynucleotide, vector, recombinant host cell, and/or pharmaceutical composition of the present invention and (b) an additional therapeutic agent for use in a method for the treatment of cancer.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent.

In certain embodiments, the additional therapeutic agent is a chemotherapeutic. In certain embodiments, the additional therapeutic agent is a radiotherapeutic.

In certain embodiments, the additional therapeutic agent is a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-CD137 antibody, an antagonist anti-TIGIT antibody, an antagonist anti-VISTA antibody, an agonist anti-GITR antibody, and an agonist anti-OX40 antibody. In certain embodiments, the additional therapeutic agent is an anti-PD-1 antibody. In certain embodiments, the anti-PD-1 antibody is pembrolizumab. In certain embodiments, the anti-PD-1 antibody is nivolumab.

In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the inhibitor is epacadostat. In certain embodiments, the inhibitor is F001287. In certain embodiments, the inhibitor is indoximod. In certain embodiments, the inhibitor is NLG919.

In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject. In certain embodiments, the additional therapeutic agent comprises a TCR. In certain embodiments, the additional therapeutic agent is a soluble TCR. In certain embodiments, the additional therapeutic agent is a cell expressing a TCR. In certain embodiments, the additional therapeutic agent is a cell expressing a chimeric antigen receptor. In certain embodiments, the additional therapeutic agent is an antibody that specifically binds to a peptide-MHC complex. In certain embodiments, the additional therapeutic agent is an adjuvant. In one aspect, the present invention relates to (a) an antibody, polynucleotide, vector, recombinant host cell, and/or pharmaceutical composition of the present invention and (b) a vaccine for use as a medicament, for example, for use in a method for the treatment of cancer, optionally wherein the vaccine comprises a heat shock protein peptide complex (HSPPC) comprising a heat shock protein complexed with an antigenic peptide. In one aspect, the present invention relates to a pharmaceutical composition, kit or kit-of-parts comprising (a) an antibody, polynucleotide, vector, recombinant host cell, and/or pharmaceutical composition of the present invention and (b) a vaccine, optionally wherein the vaccine comprises a heat shock protein peptide complex (HSPPC) comprising a heat shock protein complexed with an antigenic peptide.

4. BRIEF DESCRIPTION OF THE DRAWINGS

FIG. 1 is a set of histograms showing the binding of anti-TIM-3 antibodies pab2085 ($IgG_1$) and pab2088 ($IgG_1$) or an isotype control antibody to wild type murine 1624-5 cells or 1624-5 cells engineered to express human TIM-3, as measured by flow cytometry.

Figure 2A:
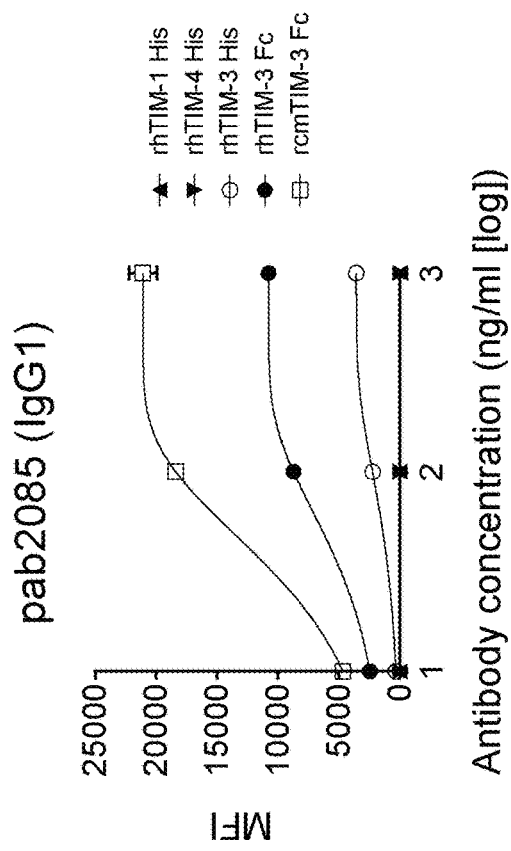
Figure 2B:
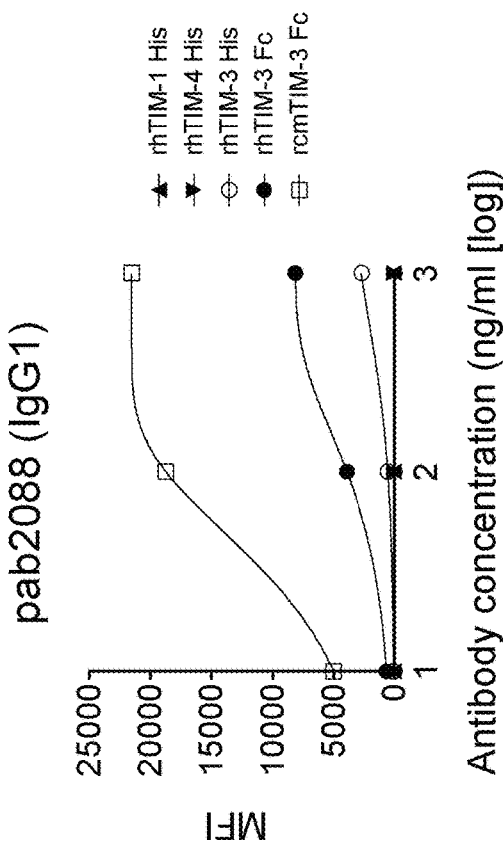
Figure 3A:
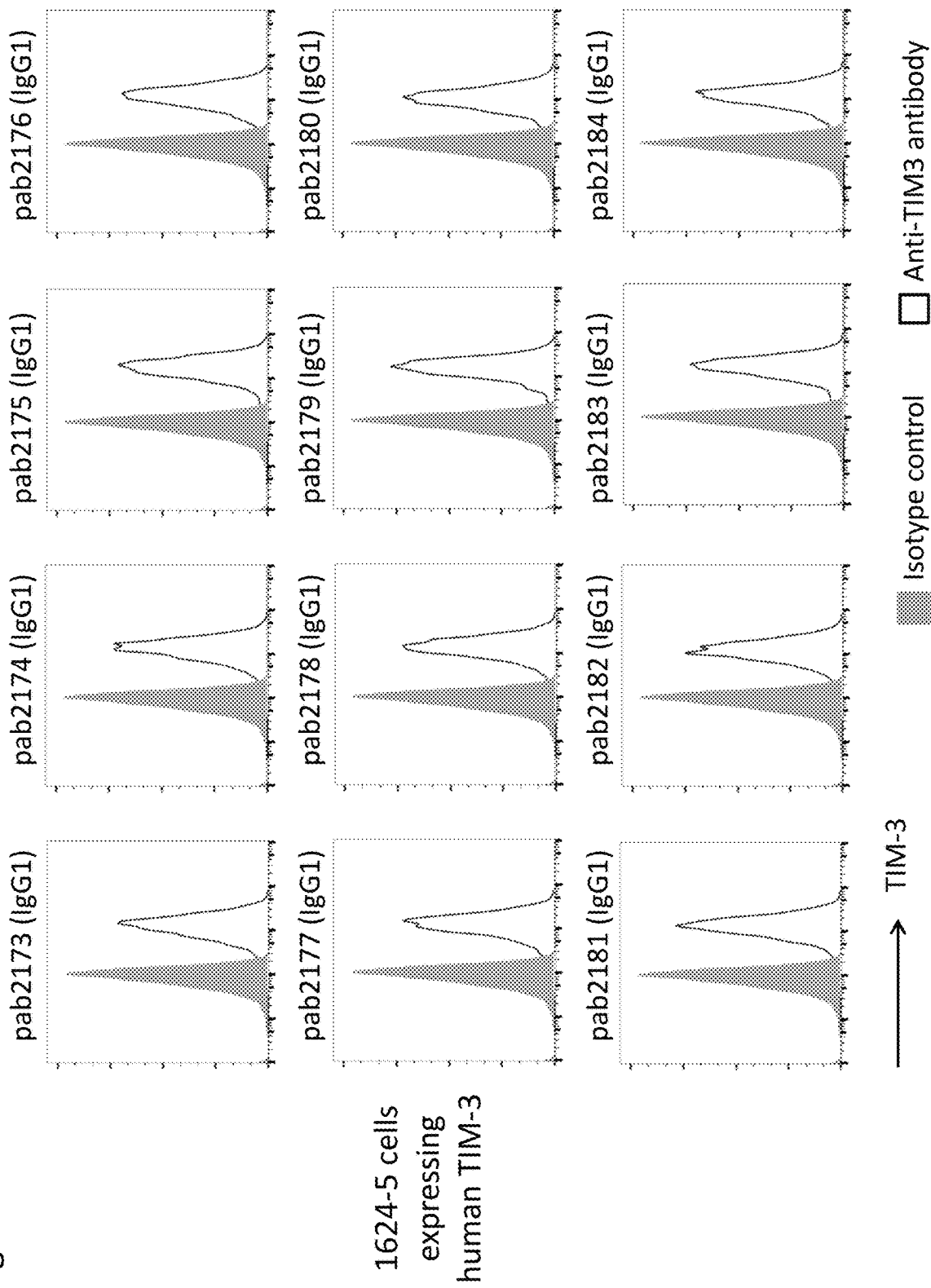
Figure 3B:
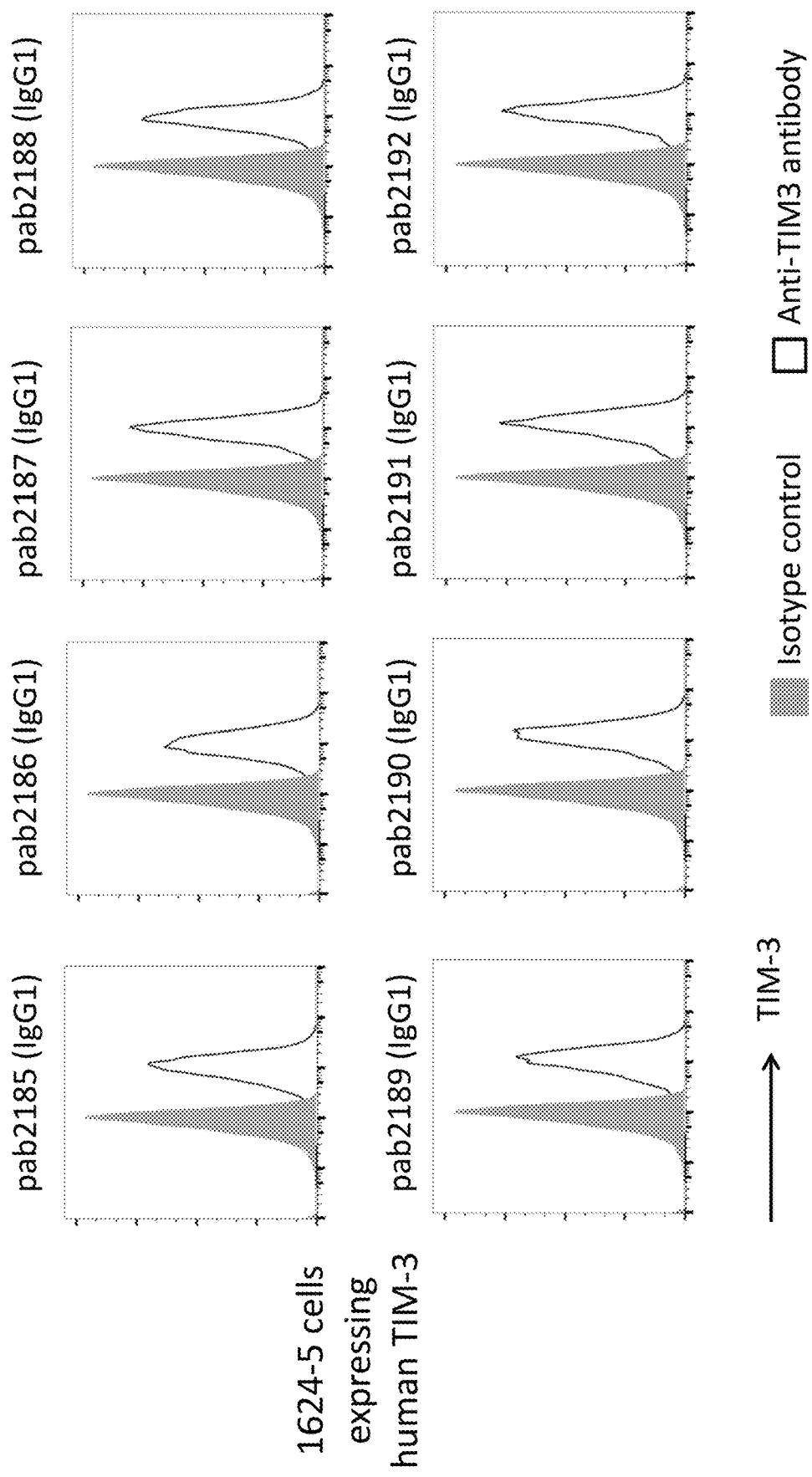
Figure 3C:
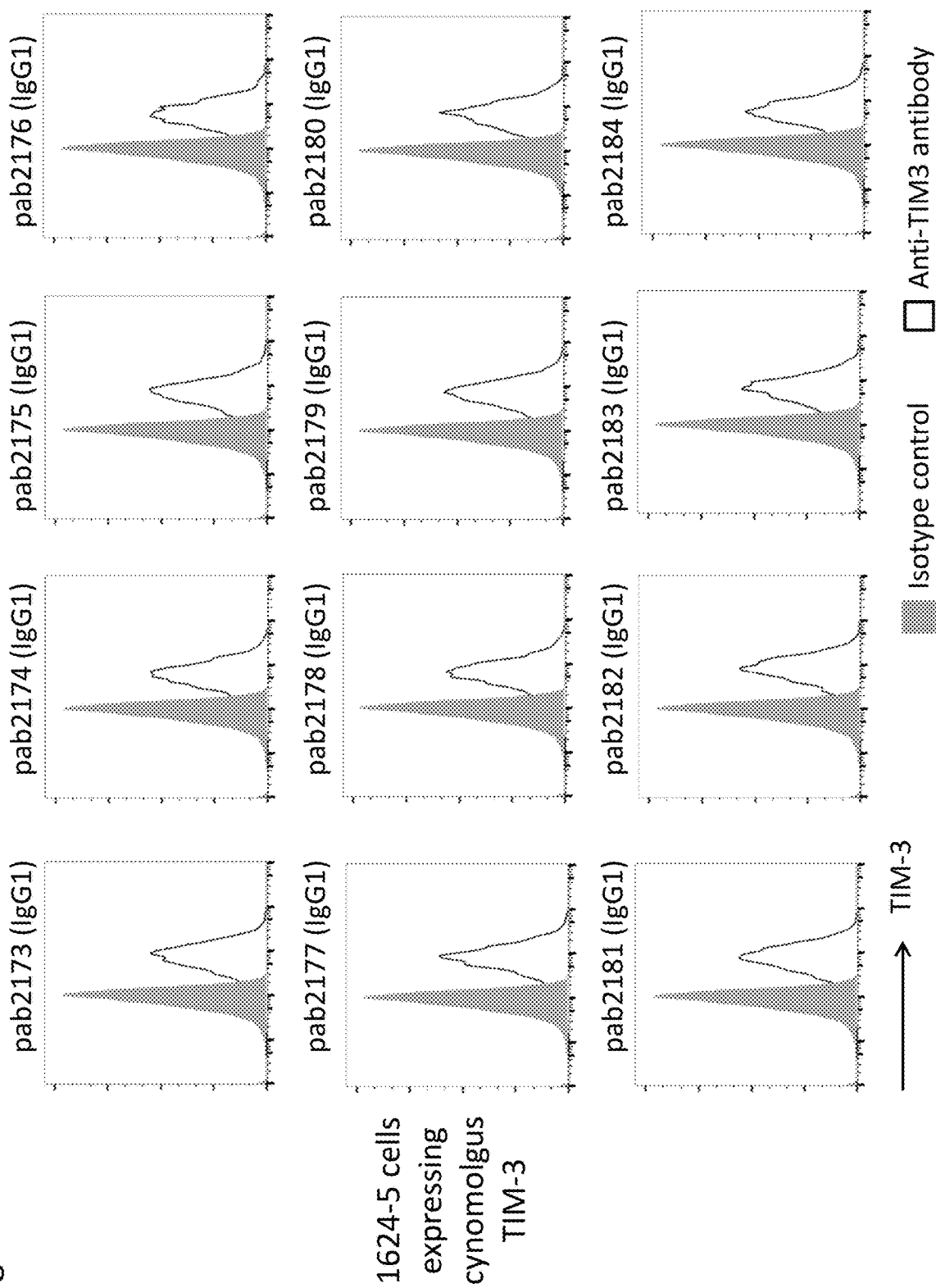
Figure 3D:
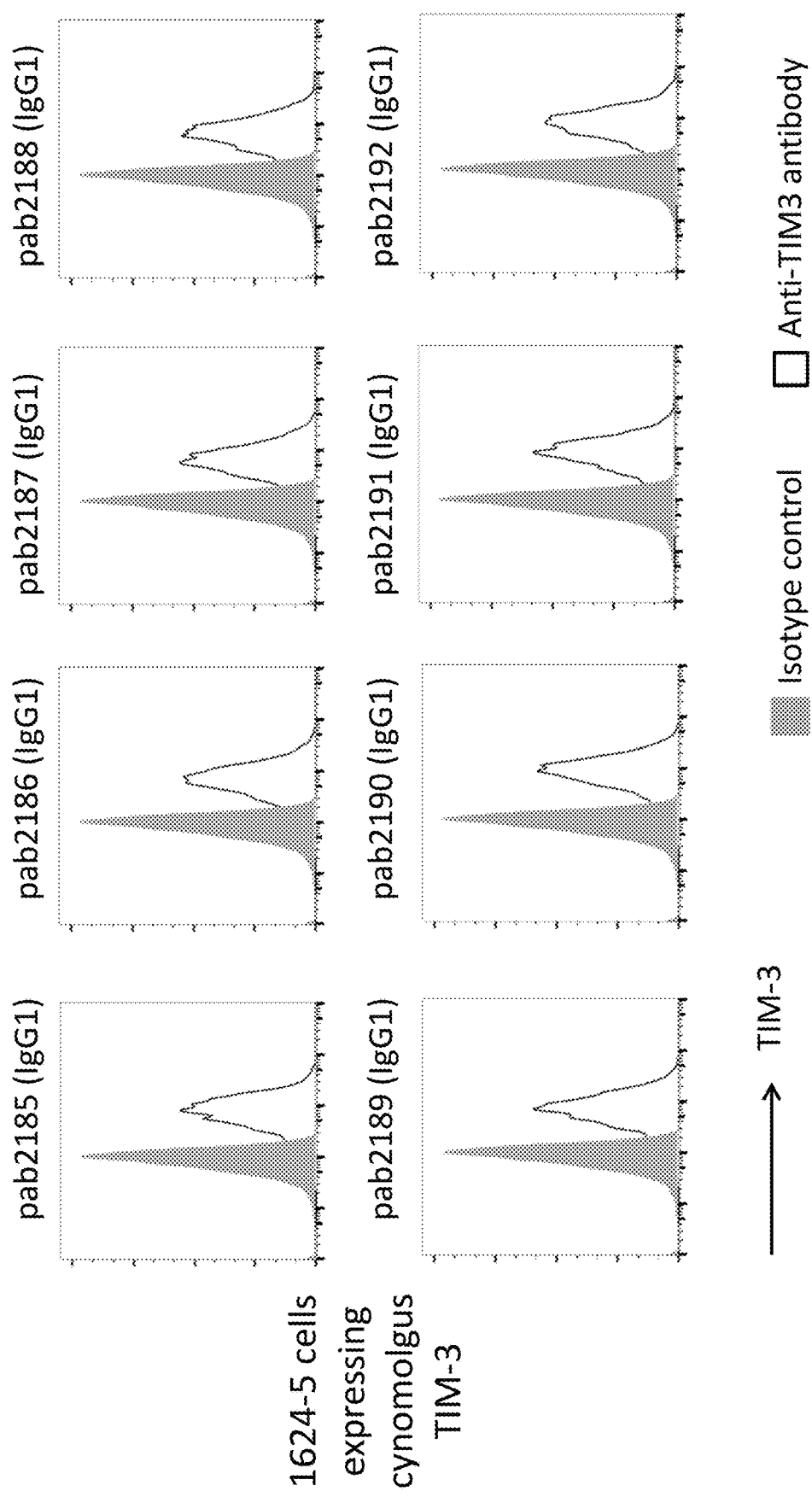

FIGS. 2A and 2B are a pair of graphs showing the binding of anti-TIM-3 antibodies pab2085 ($IgG_1$) (FIG. 2A) and pab2088 ($IgG_1$) (FIG. 2B) to recombinant human TIM-1 His (rhTIM-1 His), recombinant human TIM-4 His (rhTIM-4 His), recombinant human TIM-3 His (rhTIM-3 His), recombinant human TIM-3 Fc (rhTIM-3 Fc), and recombinant cynomolgus TIM-3 Fc (rcmTIM-3 Fc), as measured by a Luminex® assay. The median fluorescence intensity (MFI) values are plotted against antibody concentrations.

FIGS. 3A, 3B, 3C, and 3D are a set of histograms showing the binding of anti-TIM-3 antibodies or an isotype control antibody to murine 1624-5 cells engineered to express human TIM-3 (FIGS. 3A and 3B) or cynomolgus TIM-3 (FIGS. 3C and 3D), as measured by flow cytometry. The anti-TIM-3 antibodies tested in this study include pab2173, pab2174, pab2175, pab2176, pab2177, pab2178, pab2179, pab2180, pab2181, pab2182, pab2183, pab2184, pab2185, pab2186, pab2187, pab2188, pab2189, pab2190, pab2191, and pab2192, all of which contain an $IgG_1$ Fc region.

Figure 4:
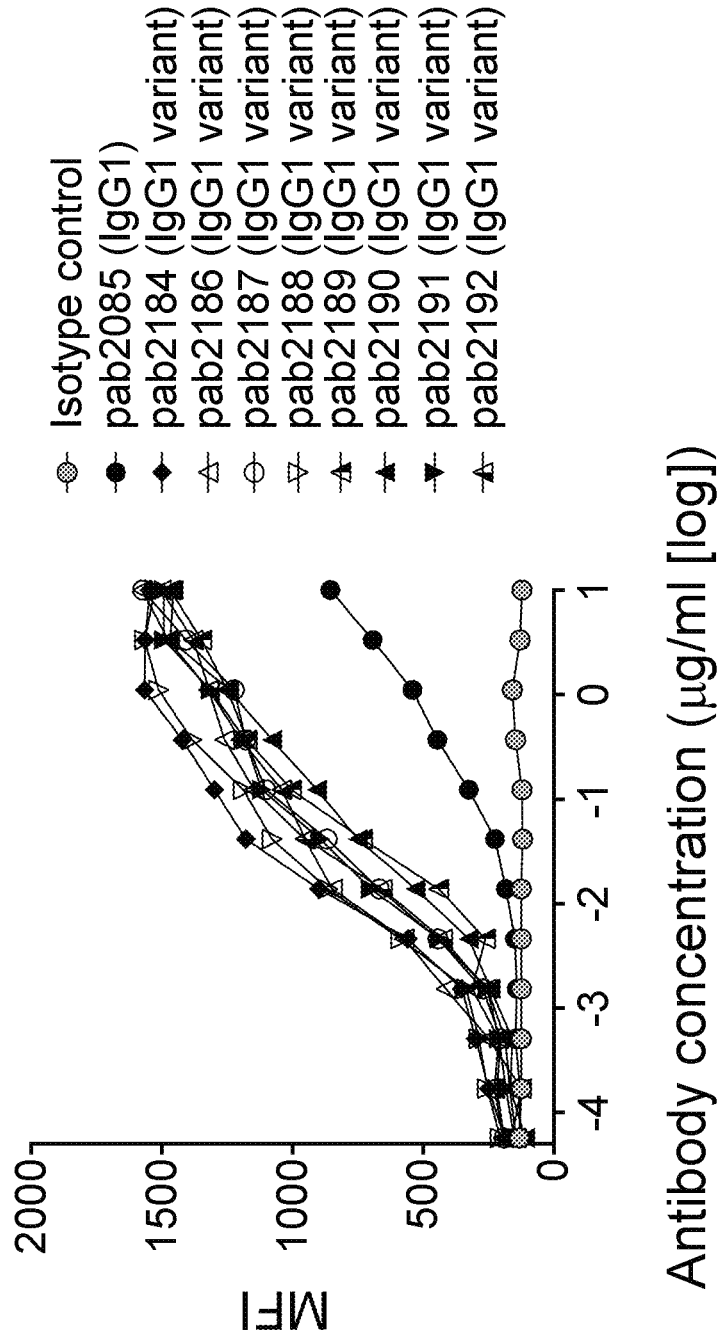

FIG. 4 is a graph showing the binding of anti-TIM-3 antibody pab2085, light-chain optimized variants (pab2184, pab2186, pab2187, pab2188, pab2189, pab2190, pab2191, and pab2192), or an isotype control antibody to primary human CD8+ T cells activated by anti-CD3 and anti-CD28 antibodies, measured by flow cytometry. The light chain optimized variants contain an $IgG_1$ variant Fc region. The MFI values are plotted against a series of antibody concentrations tested.

Figure 5:
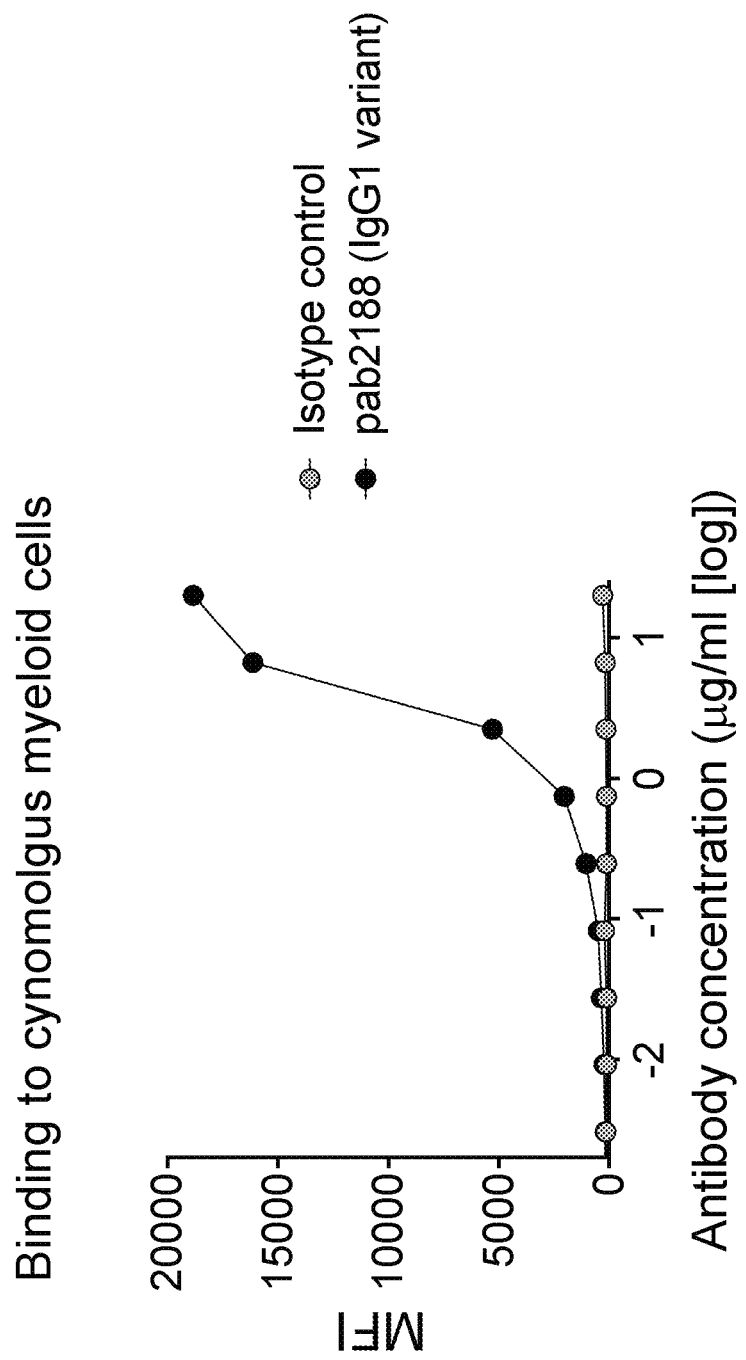

FIG. 5 is a graph showing the binding of the anti-TIM-3 antibody pab2188 ($IgG_1$ variant) or an isotype control antibody to primary cynomolgus CD11b+ myeloid cells, measured by flow cytometry. The MFI values are plotted against antibody concentrations.

Figure 6A:
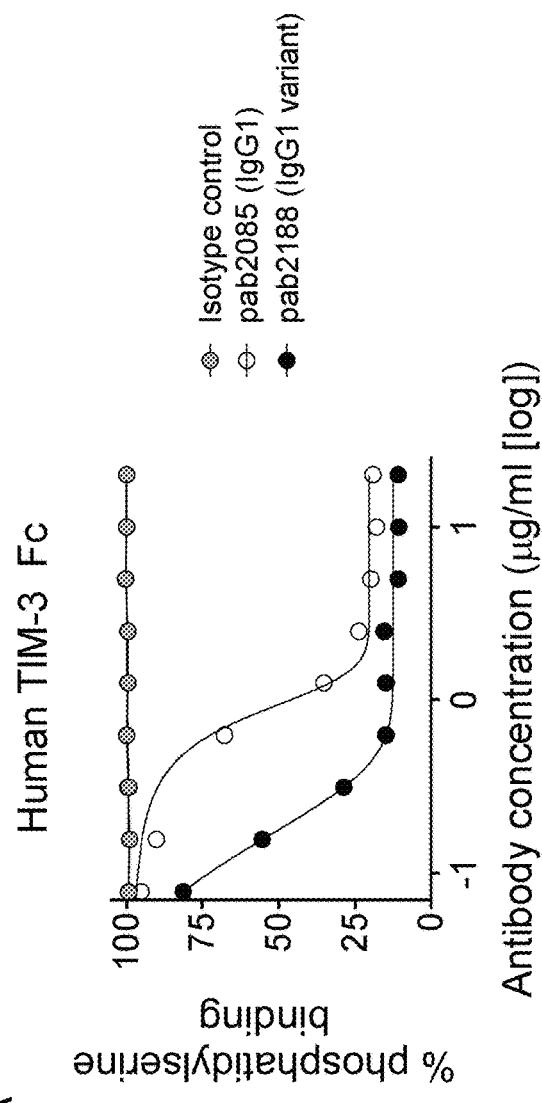
Figure 6B:
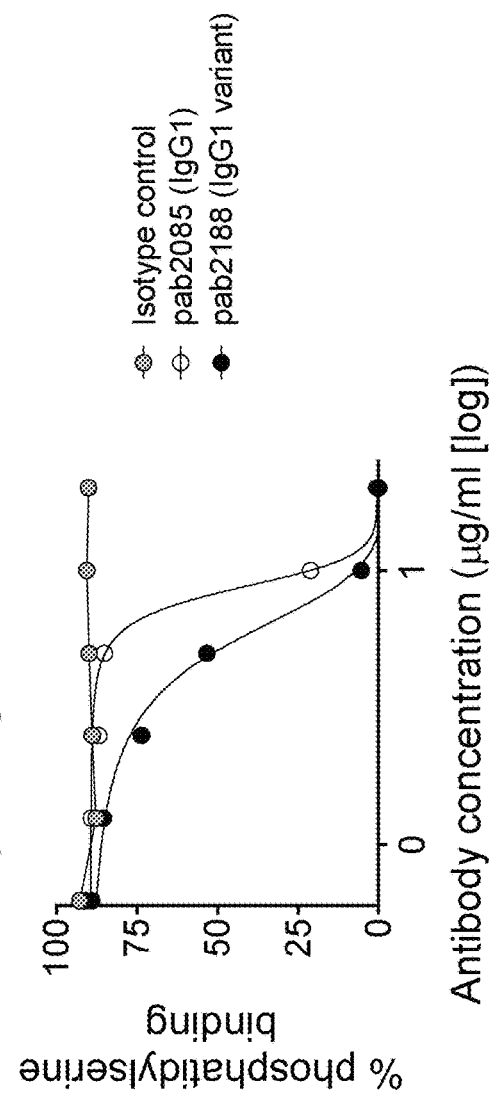

FIGS. 6A and 6B are graphs showing the percent of binding between irradiated phosphatidylserine-expressing WR19L murine lymphoma cells and recombinant human TIM-3 Fc (FIG. 6A) or recombinant cynomolgus TIM-3 Fc (FIG. 6B) in the presence of a dose titration of an anti-TIM-3 antibody or an $IgG_1$ isotype control antibody. The anti-TIM-3 antibodies tested in this study are pab2085 ($IgG_1$) and pab2188 ($IgG_1$ variant).

Figure 7:
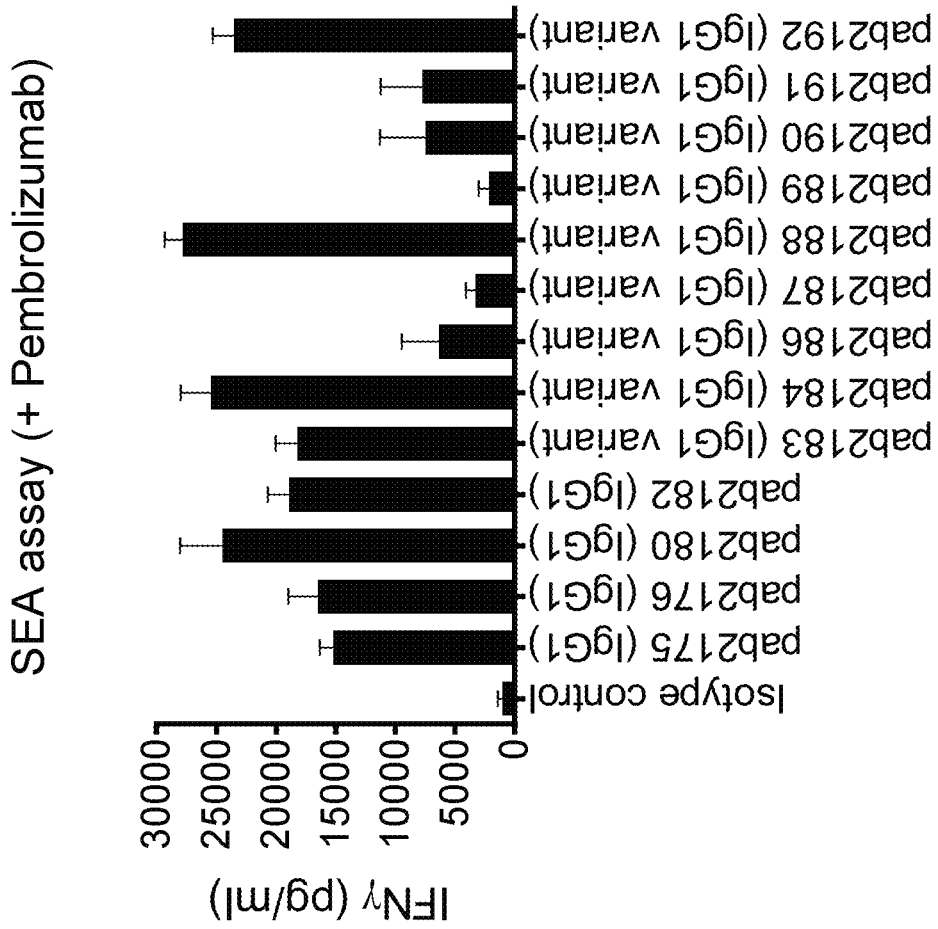
Figure 8A:
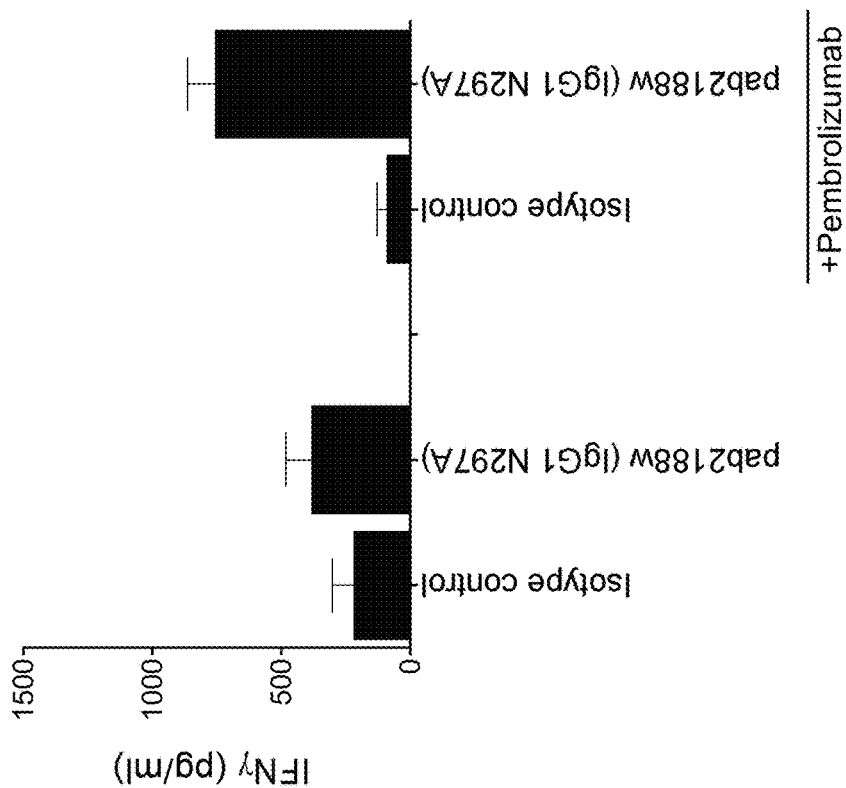
Figure 8B:
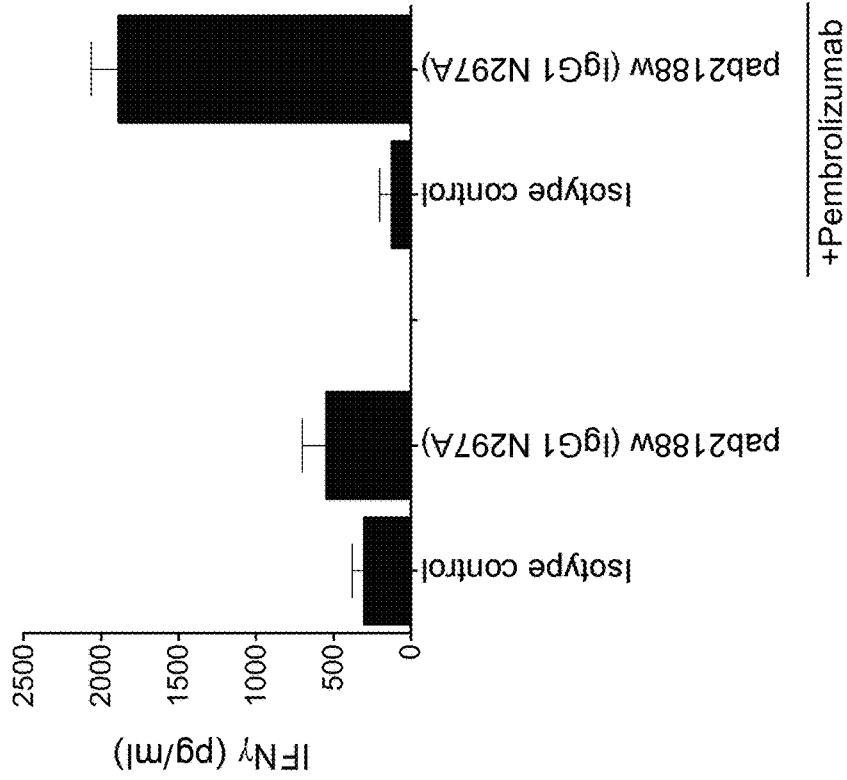
Figure 8C:
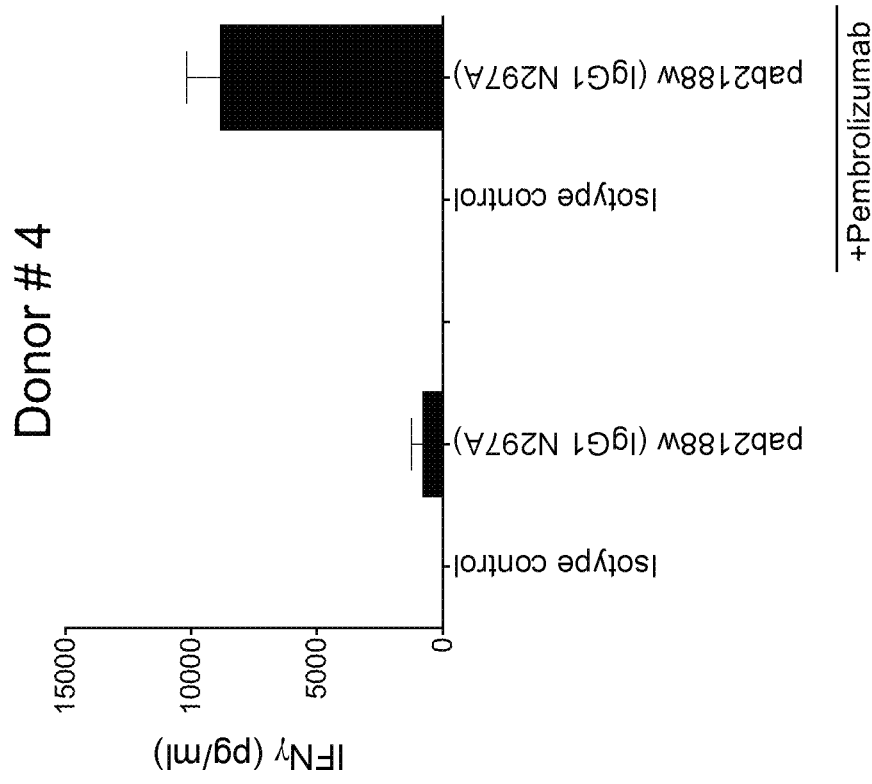
Figure 8D:
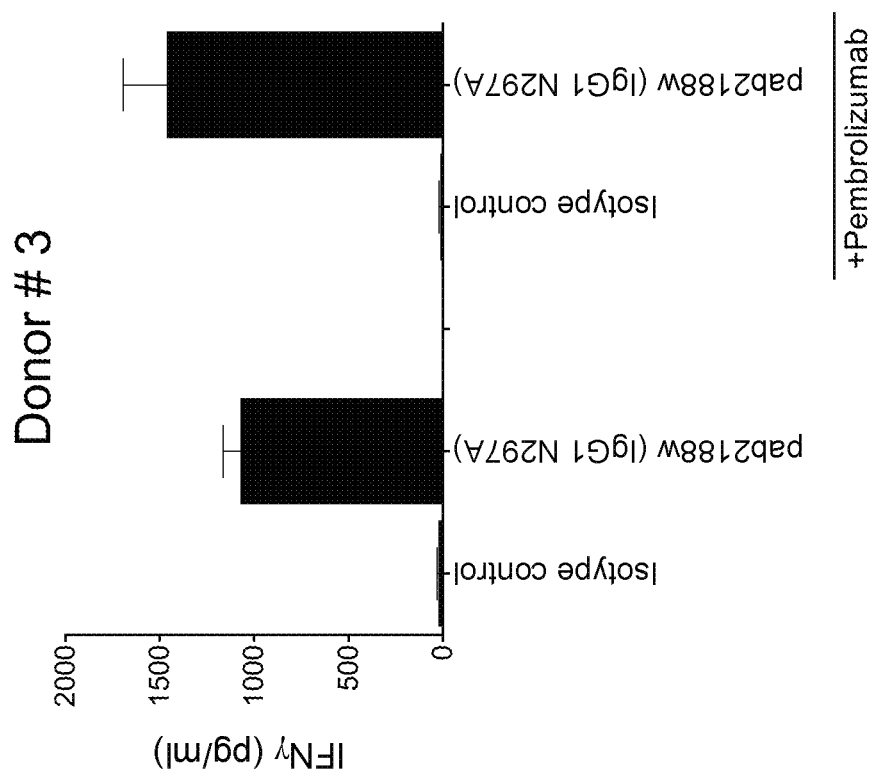
Figure 8E:
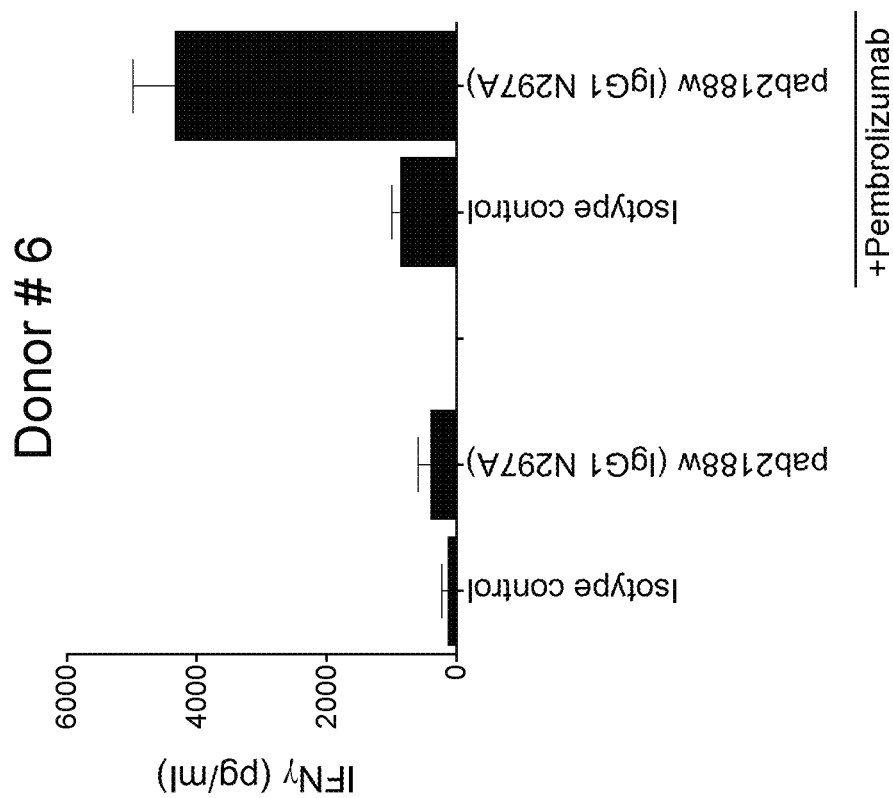
Figure 8F:
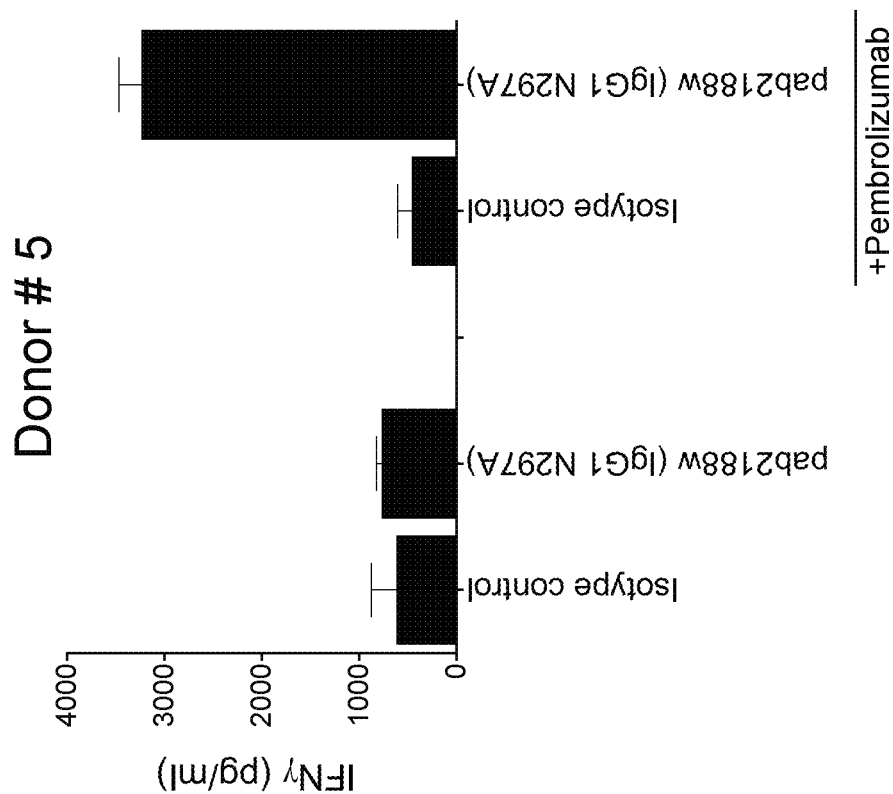

FIG. 7 is a bar graph showing the production of IFNγ induced by anti-TIM-3 antibodies or an $IgG_1$ isotype control antibody in combination with the anti-PD-1 antibody pembrolizumab in human peripheral blood mononuclear cells (PBMCs) upon *Staphylococcus* Enterotoxin A (SEA) stimulation. The anti-TIM-3 antibodies tested in this study include the light-chain optimized variants pab2175 (Ig pab2176 (Ig pab2180 (Ig pab2182 ($IgG_1$), pab2183 ($IgG_1$ variant), pab2184 ($IgG_1$ variant), pab2186 ($IgG_1$ variant), pab2187 ($IgG_1$ variant), pab2188 ($IgG_1$ variant), pab2189 ($IgG_1$ variant), pab2190 ($IgG_1$ variant), pab2191 ($IgG_1$ variant), and pab2192 ($IgG_1$ variant).

FIGS. 8A, 8B, 8C, 8D, 8E, and 8F are a set of bar graphs showing the production of IFNγ induced by the anti-TIM-3 antibody pab2188w ($IgG_1$ N297A) or an $IgG_1$ N297A isotype control antibody, either alone or in combination with the anti-PD-1 antibody pembrolizumab, in human PBMCs from six different donors upon SEA stimulation. The protocol used in the study depicted in FIGS. 8A-8F was modified from the protocol used in the study depicted in FIG. 7.

Figure 9A:
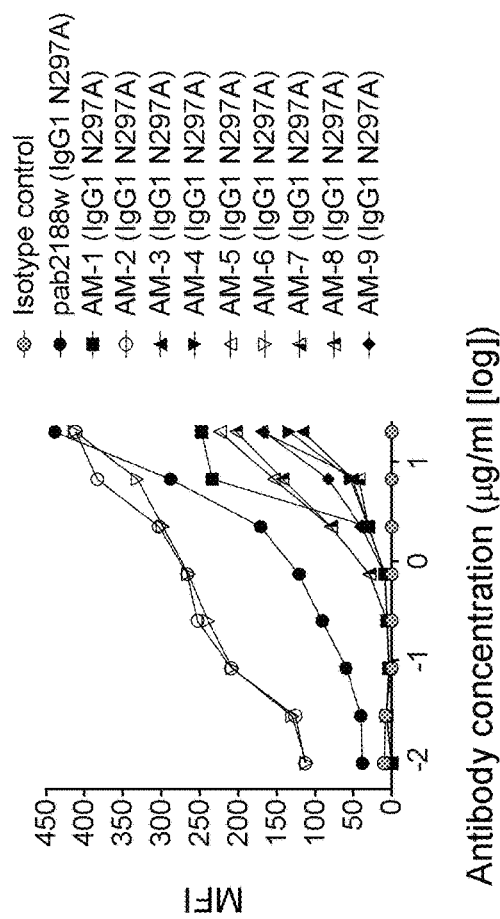
Figure 9B:
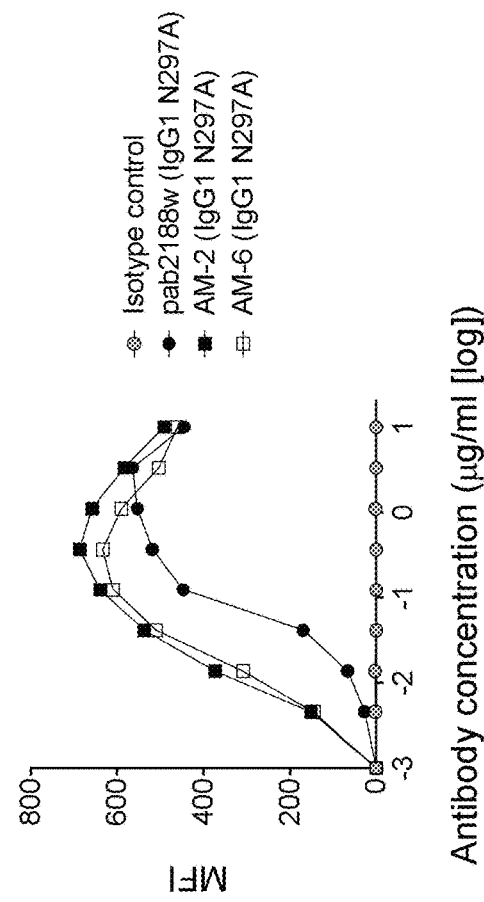
Figure 9E:
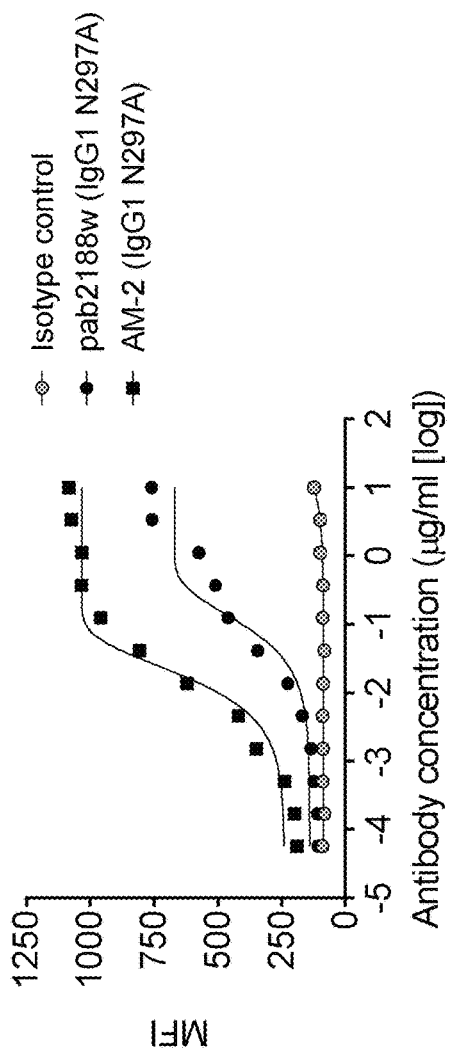
Figure 9F:
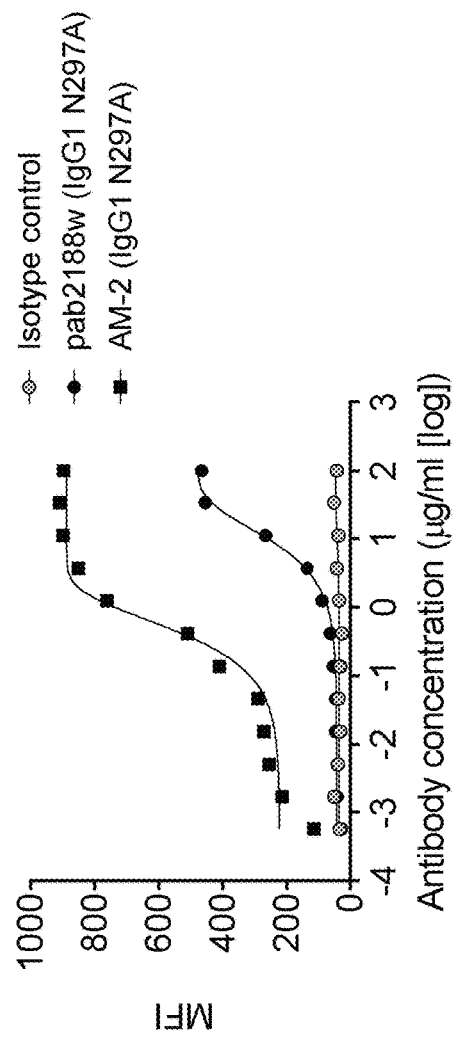

FIGS. 9A, 9B, 9C, 9D, 9E, and 9F are graphs or histograms showing binding of anti-TIM-3 antibodies to cells expressing TIM-3. In FIGS. 9A, 9B, 9E, and 9F, MFI values are plotted against a series of antibody concentrations tested. FIGS. 9C and 9D are a set of histograms showing binding of anti-TIM-3 antibodies to TIM-3-expressing cells. The anti-TIM-3 antibodies tested include pab2188w ($IgG_1$ N297A), AM-1 ($IgG_1$ N297A), AM-2 ($IgG_1$ N297A), AM-3 ($IgG_1$ N297A), AM-4 ($IgG_1$ N297A), AM-5 ($IgG_1$ N297A), AM-6 ($IgG_1$ N297A), AM-7 ($IgG_1$ N297A), AM-8 ($IgG_1$ N297A), and AM-9 ($IgG_1$ N297A). The cells tested were Jurkat cells ectopically expressing human TIM-3 (FIG. 9A), Kasumi-3, a human acute myeloid leukemia cell line endogenously expressing TIM-3 (FIG. 9B), human CD8+ T cells stimulated with Staphylococcal Enterotoxin A (SEA) (FIG. 9C), cynomolgus CD8+ T cells stimulated with SEA (FIG. 9D), and primary human (FIG. 9E) and cynomolgus (FIG. 9F) CD14+ myeloid cells.

FIGS. 10A, 10B, 10C, and 10D are graphs showing the binding of anti-TIM-3 antibodies or an $IgG_1$ N297A isotype control antibody to recombinant human TIM-3 His (rhTIM-3 His), recombinant cynomolgus TIM-3 Fc (rcmTIM-3 Fc), recombinant mouse TIM-3 Fc (rmTIM-3 Fc), recombinant human TIM-1 His (rhTIM-1 His), recombinant human TIM-4 His (rhTIM-4 His), recombinant human OX40 His (rhOX40 His), recombinant human GITR Fc (rhGITR Fc), recombinant human DR3 Fc (rhDR3 Fc), and recombinant human CD137 Fc (rhCD137 Fc), measured by a Luminex® assay. The MFI values are plotted against antibody concentrations. The anti-TIM-3 antibodies tested in this study include pab2188w ($IgG_1$ N297A) (FIG. 10B), AM-2 ($IgG_1$ N297A) (FIG. 10C), and AM-6 ($IgG_1$ N297A) (FIG. 10D).

Figure 11A:
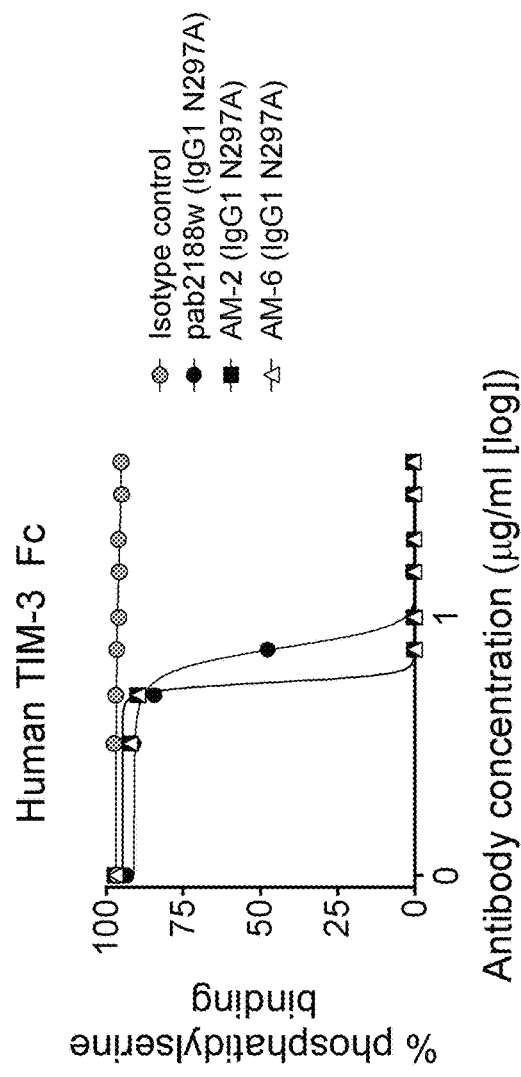
Figure 11B:
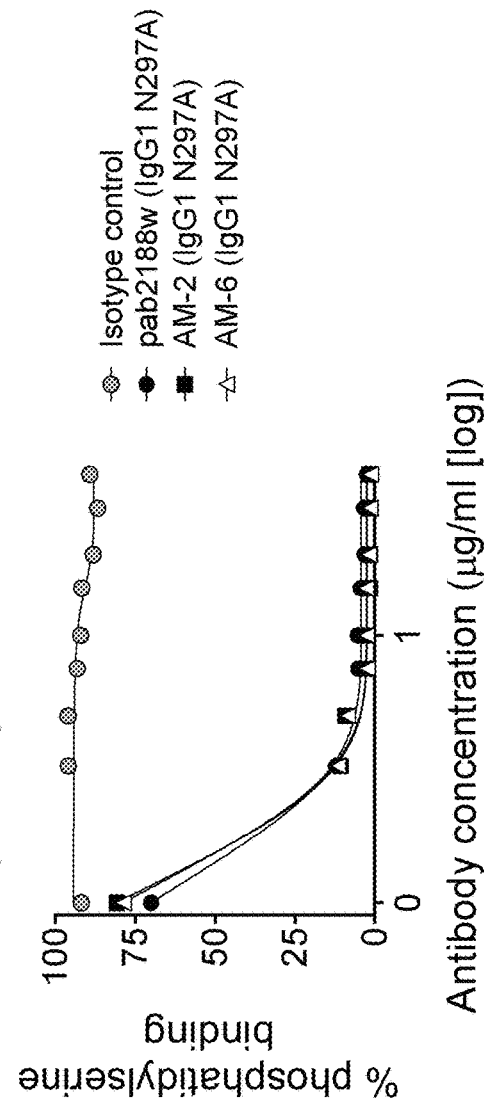

FIGS. 11A and 11B are graphs showing the percent of binding of recombinant human TIM-3 Fc (FIG. 11A) or recombinant cynomolgus TIM-3 Fc (FIG. 11B) to phosphatidylserine-expressing WR19L cells in the presence of a dose titration of anti-TIM-3 antibodies or an $IgG_1$ N297A isotype control antibody. The anti-TIM-3 antibodies tested in this study include pab2188w ($IgG_1$ N297A), AM-2 ($IgG_1$ N297A), and AM-6 ($IgG_1$ N297A).

Figure 12A:
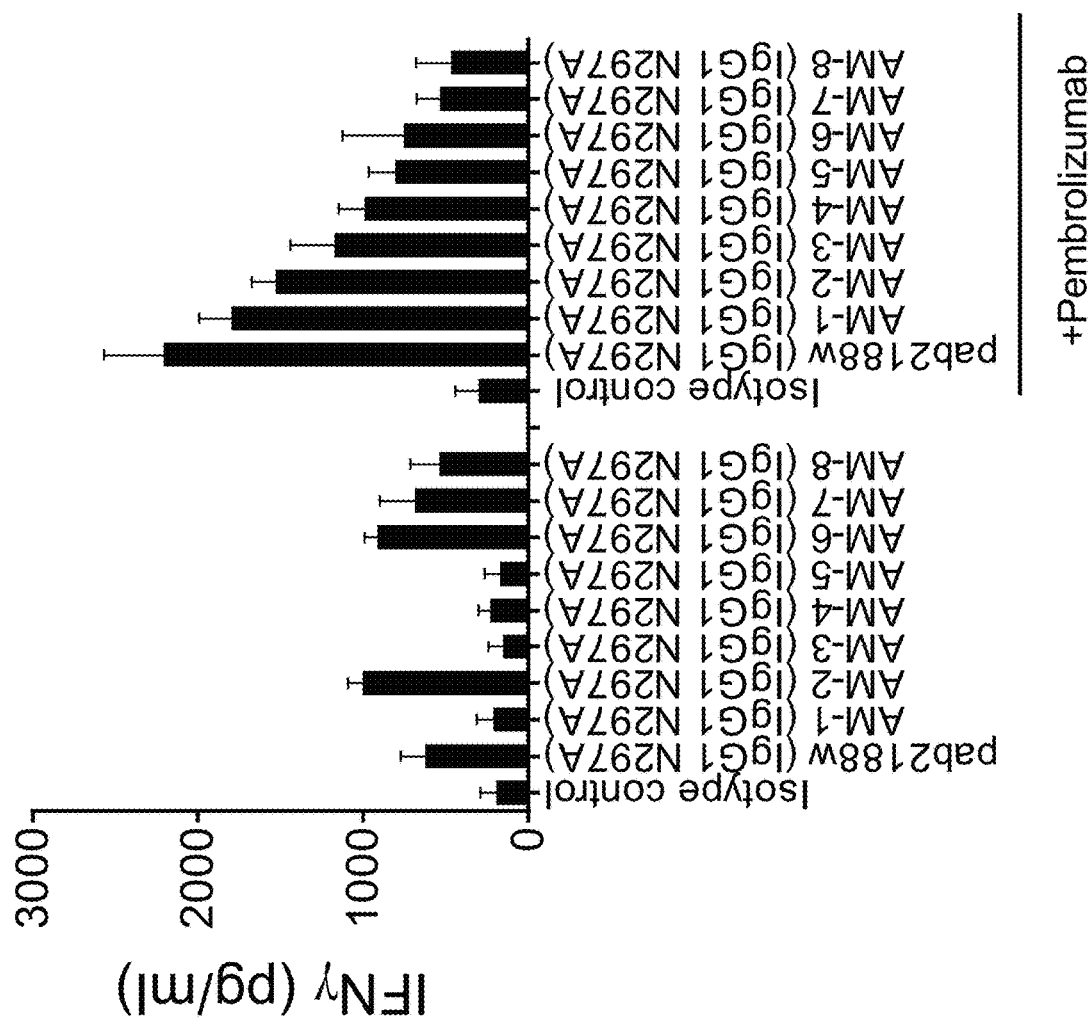
Figure 12B:
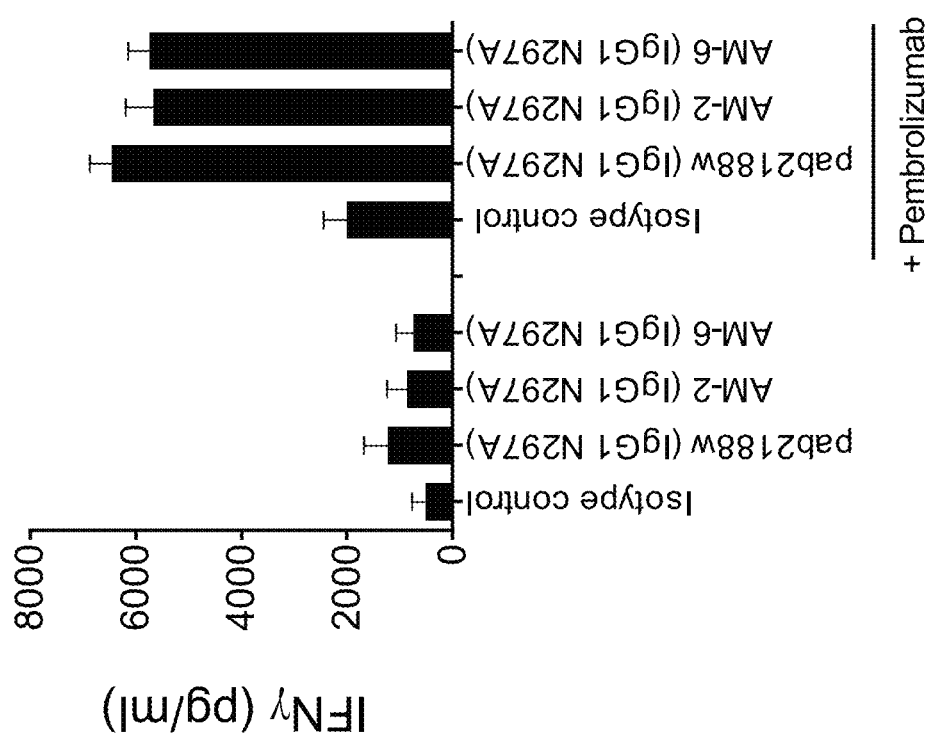
Figure 13A:
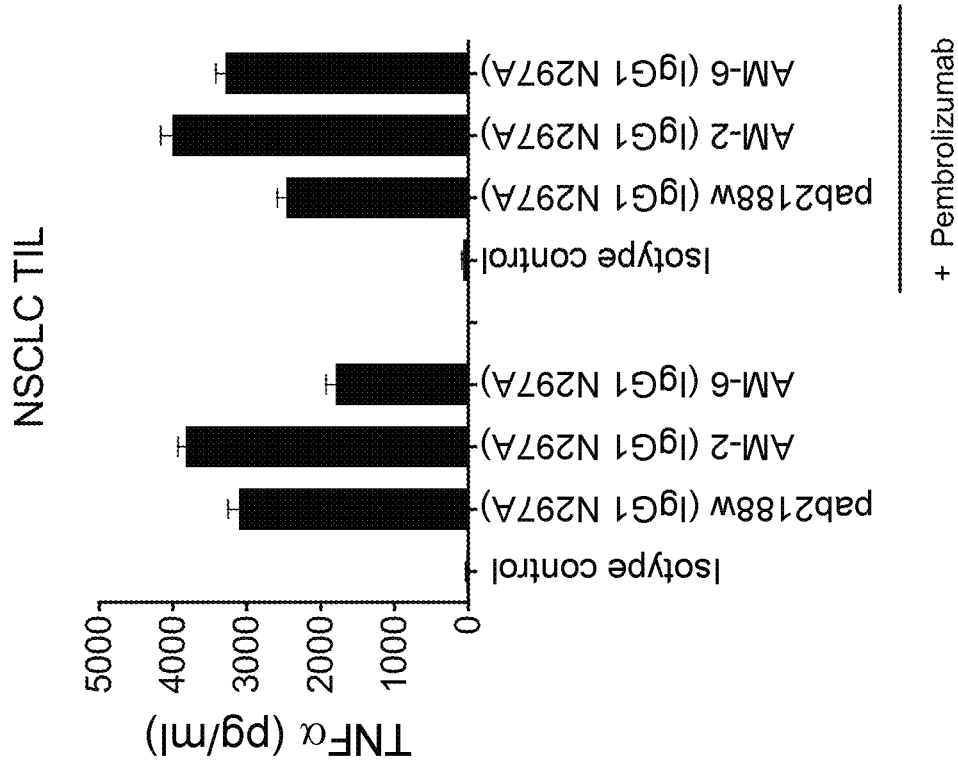
Figure 13B:
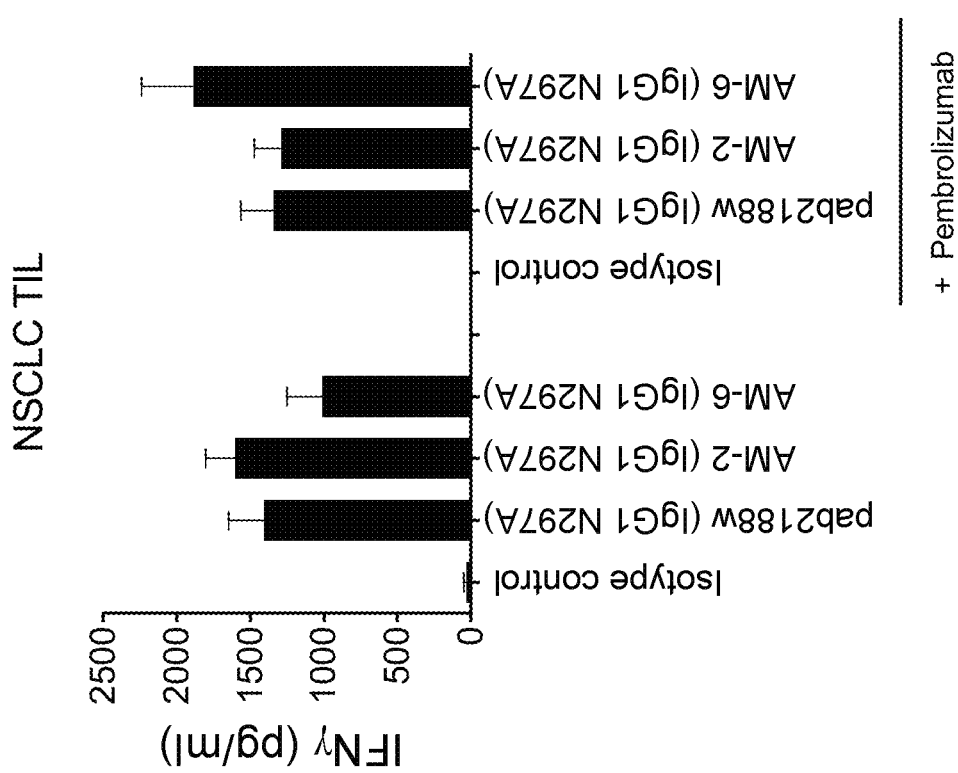
Figure 13C:
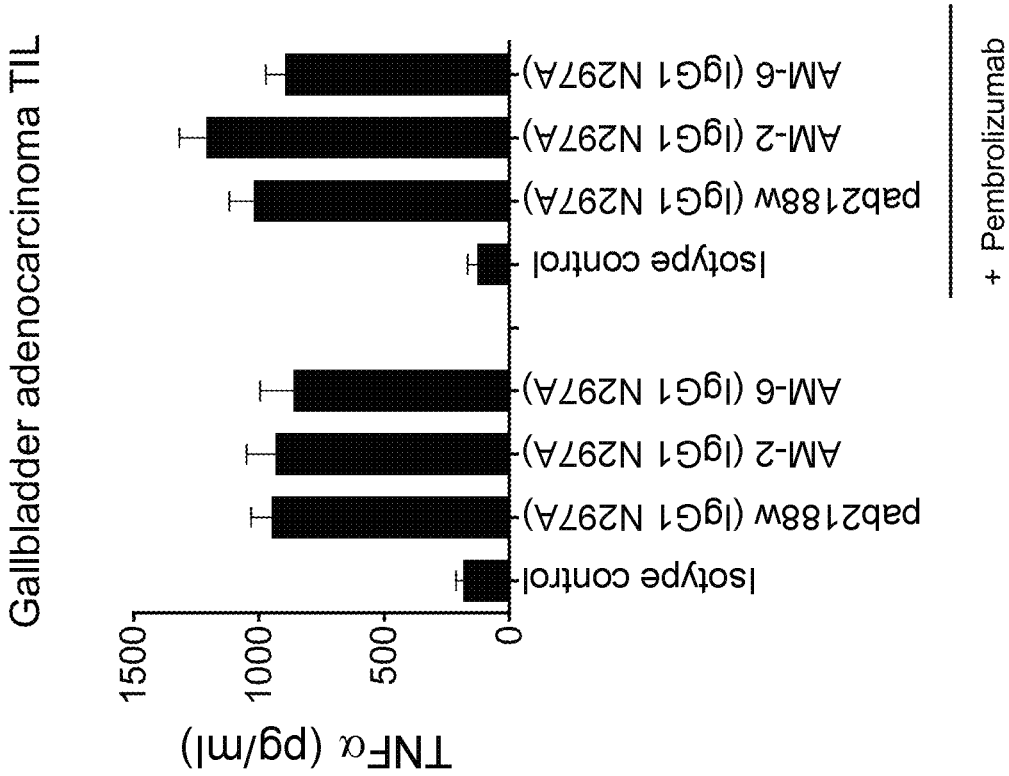
Figure 13D:
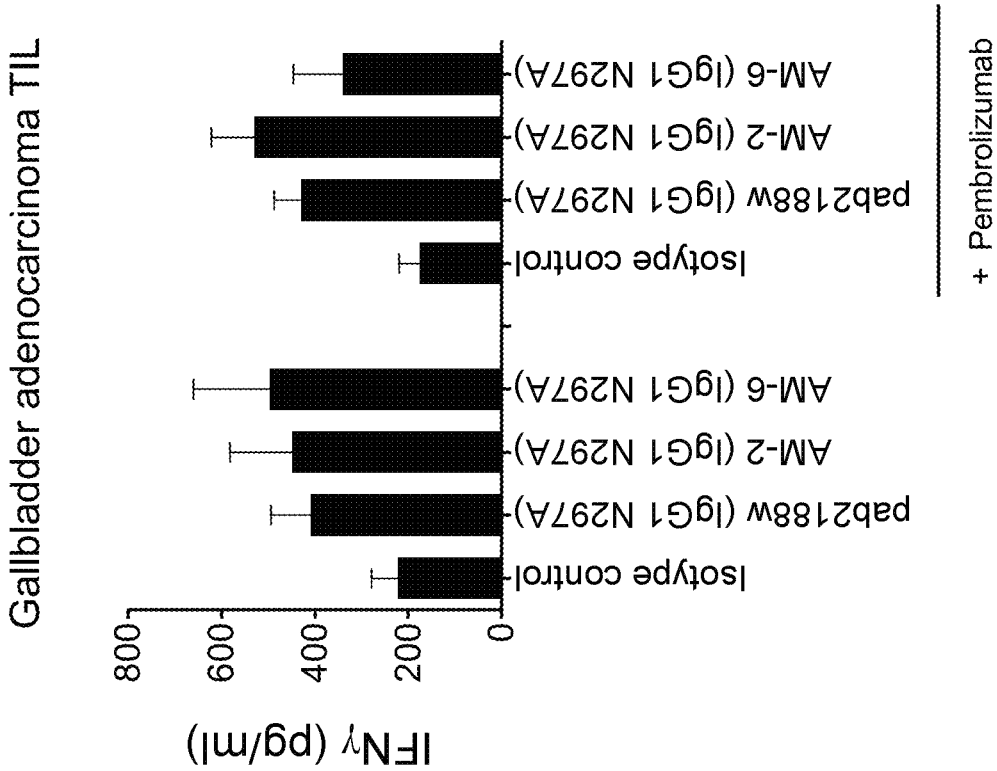
Figure 13E:
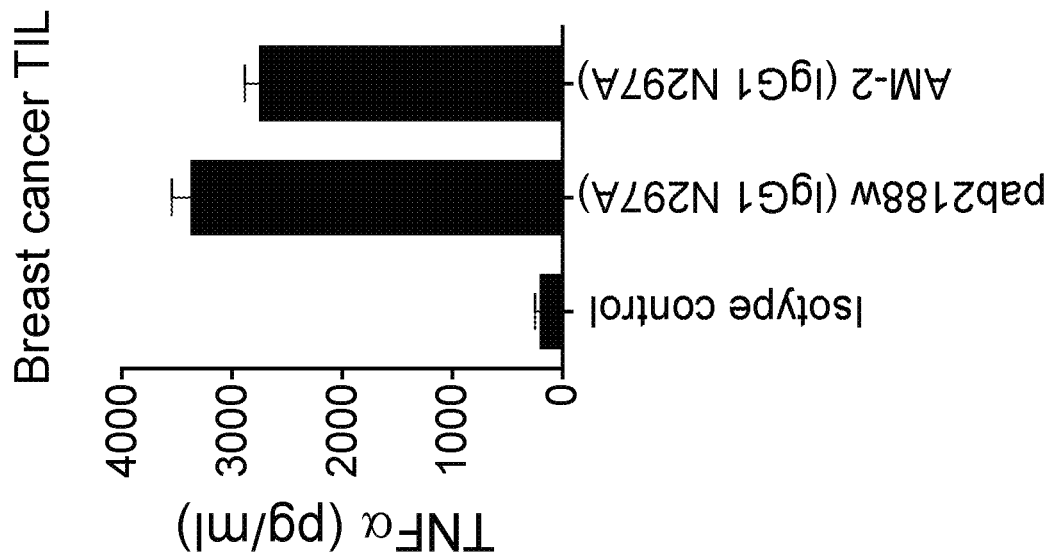
Figure 13F:
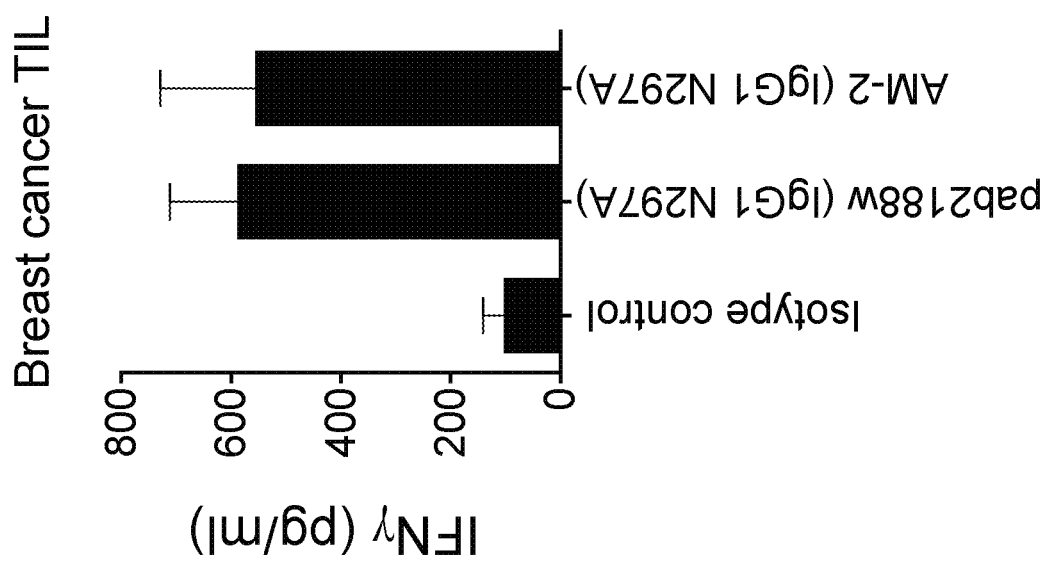

FIGS. 12A and 12B are bar graphs showing the production of IFNγ induced by anti-TIM-3 antibodies or an IgG$_1$ N297A isotype control antibody, either alone or in combination with the anti-PD-1 antibody pembrolizumab, in human PBMCs from two different donors upon SEA stimulation. The anti-TIM-3 antibodies tested include pab2188w (IgG$_1$ N297A), AM-1 (IgG$_1$ N297A), AM-2 (IgG$_1$ N297A), AM-3 (IgG$_1$ N297A), AM-4 (IgG$_1$ N297A), AM-5 (IgG$_1$ N297A), AM-6 (IgG$_1$ N297A), AM-7 (IgG$_1$ N297A), and AM-8 (IgG$_1$ N297A).

FIGS. 13A, 13B, 13C, 13D, 13E, and 13F are graphs showing IFNγ or TNFα production by primary tumor infiltrating lymphocytes (TILs) induced by anti-TIM-3 antibodies or an IgG$_1$ N297A isotype control antibody, either alone or in combination with the anti-PD-1 antibody pembrolizumab. The TILs were isolated from non-small cell lung cancer (NSCLC) (FIGS. 13A and 13B), gallbladder adenocarcinoma (FIGS. 13C and 13D), or breast cancer (FIGS. 13E and 13F) tumors and activated with anti-CD3/CD28 microbeads. The anti-TIM-3 antibodies tested in this study include pab2188w (IgG$_1$ N297A), AM-2 (IgG$_1$ N297A), and AM-6 (IgG$_1$ N297A).

Figure 14A:
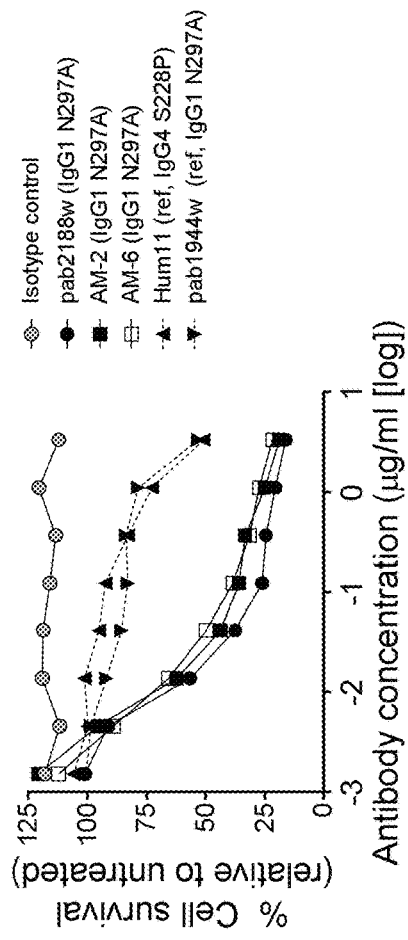
Figure 14B:
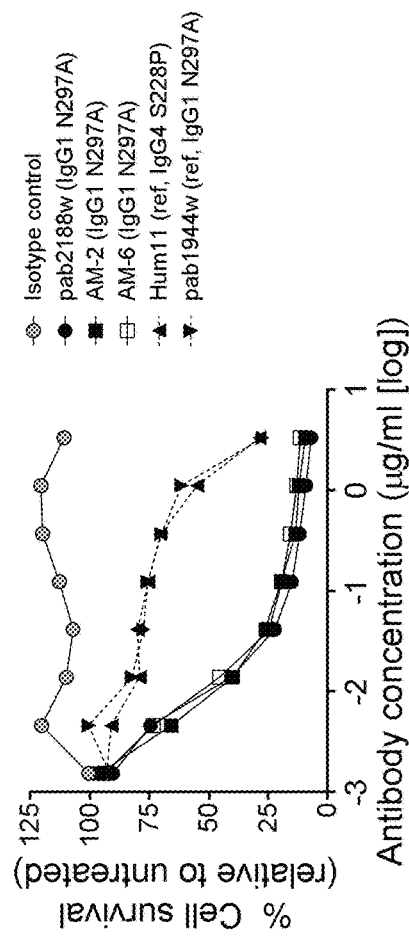
Figure 14C:
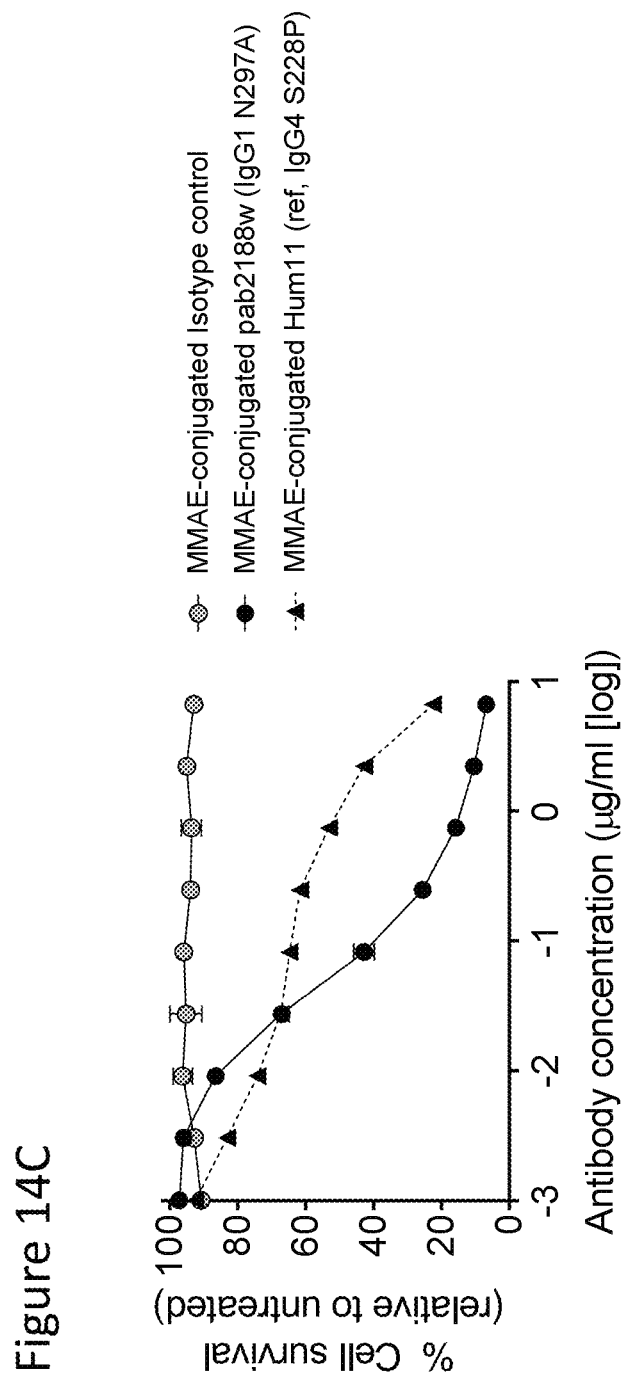

FIGS. 14A, 14B, and 14C are graphs showing the percent of cell survival, relative to an untreated control group, after incubation with an anti-TIM-3 antibody or an IgG$_1$ N297A isotype control antibody. FIGS. 14A and 14B show treatment with the indicated antibody in combination with a secondary antibody drug conjugate αHFc-NC-DM1. The cells tested were Jurkat cells engineered to overexpress TIM-3 (FIG. 14A) or Kasumi-3 cells, an acute myeloid leukemia cell line endogenously expressing TIM-3 (FIG. 14B). FIG. 14C shows treatment with the indicated antibody as a conjugate with monomethyl auristatin E (MMAE). The anti-TIM-3 antibodies tested in this study include pab2188w (IgG$_1$ N297A), AM-2 (IgG$_1$ N297A), AM-6 (IgG$_1$ N297A), and reference antibodies Hum11 (IgG$_4$ S228P) and pab1944w (IgG$_1$ N297A).

Figure 15:
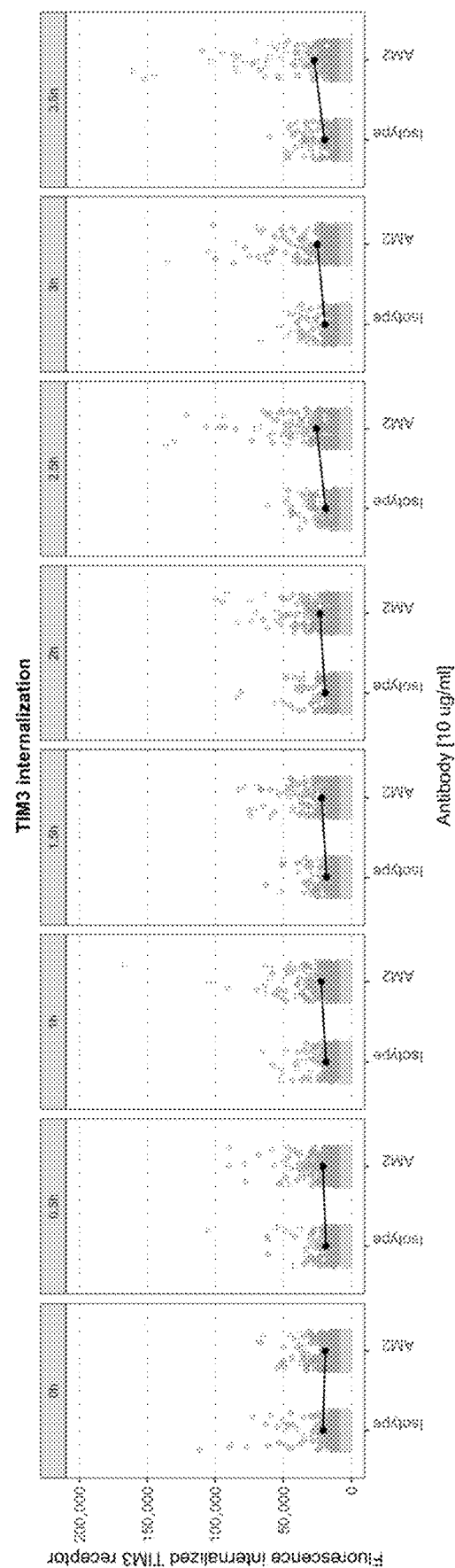

FIG. 15 is a series of graphs showing TIM-3 internalization in Jurkat cells expressing a HaloTag®-TIM-3 fusion protein when incubated with 10 μg/mL of either anti-TIM-3 antibody AM-2 or an isotype control antibody, as determined by live cell confocal fluorescence microscopy, at various time points (i.e., at 0-3.5 hours). Black dots indicate the mean fluorescence level observed for each condition at a given time point.

5. DETAILED DESCRIPTION

The instant disclosure provides antibodies that specifically bind to TIM-3 (e.g., human TIM-3) and antagonize TIM-3 function, e.g., TIM-3-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen), and hence for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "TIM-3" refers to T cell immunoglobulin and mucin domain-3 (also known as T cell immunoglobulin and mucin-domain containing-3 protein or Hepatitis A virus cellular receptor 2 (HAVCR2)) that in humans is encoded by the HAVCR2 gene. Swiss-Prot accession number Q8TDQ0-1 provides an exemplary human TIM-3 amino acid sequence. The immature amino acid sequence of human TIM-3 is provided as SEQ ID NO: 78. The mature amino acid sequence of human TIM-3 is provided as SEQ ID NO: 79. As used herein, the term "human TIM-3" refers to TIM-3 comprising the amino acid sequence of SEQ ID NO: 79.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

As used herein, the terms "VH region" and "VL region" refer to single antibody heavy and light chain variable regions, respectively, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-

6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. For example, in certain embodiments, the heavy chain CDRs are defined according to MacCallum (supra), and the light CDRs are defined according to Kabat (supra). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as Biacore™ Assay or KinExA®. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, Biacore™ Assay, KinExA® 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to TIM-3 do not cross react with other non-TIM-3 proteins. In a specific embodiment, provided herein is an antibody that binds to TIM-3 (e.g., human TIM-3) with higher affinity than to another unrelated antigen. In certain embodiments, provided herein is an antibody that binds to TIM-3 (e.g., human TIM-3) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-TIM-3 antibody described herein to an unrelated, non-TIM-3 protein is less than 10%, 15%, or 20% of the binding of the antibody to TIM-3 protein as measured by, e.g., a radioimmunoassay.

As used herein, the term "afucosylation" or "afucosylated" in the context of an Fc refers to a substantial lack of a fucose covalently attached, directly or indirectly, to residue 297 of the human $IgG_1$ Fc region, numbered according to the EU numbering system, or the corresponding residue in non-$IgG_1$ or non-human $IgG_1$ immunoglobulins. Thus, in a composition comprising a plurality of afucosylated antibodies, at least 70% of the antibodies will not be fucosylated, directly or indirectly (e.g., via intervening sugars) at residue 297 of the Fc region of the antibodies, and in some embodiments at least 80%, 85%, 90%, 95%, or 99% will not be fucosylated, directly or indirectly, at residue 297 of the Fc region.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics.

As used herein, the term "an epitope located within a region of human TIM-3" consisting of a particular amino acid sequence or a set of amino acid residues refers to an epitope comprising one or more of the amino acid residues of the specified region, wherein the specified region includes the first specified amino acid residue and the last specified amino acid residue of the region of human TIM-3. In certain embodiments, the epitope comprises each one of the amino acid residues located within the specified region. In certain embodiments, one or more additional amino acid residues of human TIM-3 outside the specified region bind to an antibody together with an epitope located within the specified region.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multispecific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "internalization" or "internalized" refers to the uptake of an antibody into an intracellular compartment of a cell upon binding of the antibody to an antigen expressed at the surface of the cell.

5.2 Anti-TIM-3 Antibodies

In one aspect, the instant disclosure provides antibodies that specifically bind to TIM-3 (e.g., human TIM-3) and antagonize TIM-3 function. The amino acid sequences of exemplary antibodies are set forth in Tables 1-4, herein.

TABLE 1

Amino acid sequences of exemplary anti-TIM-3 antibodies.

| SEQ ID NO: | Description* | Amino acid sequence |
|---|---|---|
| 1 | BADD456-2919 CDRH1 | SSYAMS |
| 2 | BADD456-2919 CDRH2 | WVSAISGSGGSTY |
| 3 | BADD456-2919 CDRH3 | AKGGDYGGNYFD |
| 4 | AM-1 CDRH1 | KAGQSS |
| 5 | AM-2 CDRH1 | RQNAWS |
| 6 | AM-3 CDRH1 | MSGQTS |
| 7 | AM-4 CDRH1 | GAGQSS |
| 8 | AM-5 CDRH1 | SAQQAS |
| 9 | AM-6 CDRH1 | ARNAWS |
| 10 | AM-7 CDRH1 | RSQQAS |
| 11 | AM-8 CDRH1 | TTQQAS |
| 12 | AM-9 CDRH1 | GGQQAS |
| 13 | BADD197-1181 CDRL1 | RASQSVSSSYLA |
| 14 | BADD412-2513 CDRL1 | RASQSVSSYLA |
| 15 | BADD456-2928 CDRL1 | RASQGISNYLA |
| 16 | BADD466-3169 CDRL1 | GASQSVSSSYLA |
| 17 | BADD197-1181 CDRL2 | GASSRAT |
| 18 | BADD456-2928 CDRL2 | AASTLQS |
| 19 | BADD466-3165 CDRL2 | GASTRAT |
| 20 | BADD466-3166 CDRL2 | DASSRAT |

TABLE 1-continued

Amino acid sequences of exemplary anti-TIM-3 antibodies.

| SEQ ID NO: | Description* | Amino acid sequence |
|---|---|---|
| 21 | BADD466-3167 CDRL2 | DASNRAT |
| 22 | BADD197-1181 CDRL3 | QQYGSSPLT |
| 23 | BADD392-2234 CDRL3 | QQYGSSPIT |
| 24 | BADD456-2919 VH | EVQLVESGGGLVQPGGSLRLSCAASGFTFSSYAMSWVRQAPGKGLEWVSAISGSGGSTYYADSVKGRFTISRDNSKNTLYLQMNSLRAEDTAVYYCAKGGDYGGNYFDYWGQGTLVTVSS |
| 25 | BADD466-3162 VH | EVQLVESGGGLVQPGGSLRLSCAASGFTFSSYAMSWVRRAPGKGLEWVSAISGSGGSTYYADSVKGRFTISRDNSKNTLYLQMNSLRAEDTAVYYCAKGGDYGGNYFDYWGQGTLVTVSS |
| 26 | BADD466-3163 VH | EVQLVESGGGLVQPRGSLRLSCAASGFTFSSYAMSWVRQAPGKGLEWVSAISGSGGSTYYADSVKGRFTISRDNSKNTLYLQMNSLRAEDTAVYYCAKGGDYGGNYFDYWGQGTLVTVSS |
| 27 | AM-1-VH | EVQLVESGGGLVQPGGSLRLSCAASGFTFKAGQSSWVRRAPGKGLEWVSAISGSGGSTYYADSVKGRFTISRDNSKNTLYLQMNSLRAEDTAVYYCAKGGDYGGNYFDYWGQGTLVTVSS |
| 28 | AM-2-VH | EVQLVESGGGLVQPGGSLRLSCAASGFTFRQNAWSWVRRAPGKGLEWVSAISGSGGSTYYADSVKGRFTISRDNSKNTLYLQMNSLRAEDTAVYYCAKGGDYGGNYFDYWGQGTLVTVSS |
| 29 | AM-3-VH | EVQLVESGGGLVQPGGSLRLSCAASGFTFMSGQTSWVRRAPGKGLEWVSAISGSGGSTYYADSVKGRFTISRDNSKNTLYLQMNSLRAEDTAVYYCAKGGDYGGNYFDYWGQGTLVTVSS |
| 30 | AM-4-VH | EVQLVESGGGLVQPGGSLRLSCAASGFTFGAGQSSWVRRAPGKGLEWVSAISGSGGSTYYADSVKGRFTISRDNSKNTLYLQMNSLRAEDTAVYYCAKGGDYGGNYFDYWGQGTLVTVSS |
| 31 | AM-5-VH | EVQLVESGGGLVQPGGSLRLSCAASGFTFSAQQASWVRRAPGKGLEWVSAISGSGGSTYYADSVKGRFTISRDNSKNTLYLQMNSLRAEDTAVYYCAKGGDYGGNYFDYWGQGTLVTVSS |
| 32 | AM-6-VH | EVQLVESGGGLVQPGGSLRLSCAASGFTFARNAWSWVRRAPGKGLEWVSAISGSGGSTYYADSVKGRFTISRDNSKNTLYLQMNSLRAEDTAVYYCAKGGDYGGNYFDYWGQGTLVTVSS |
| 33 | AM-7-VH | EVQLVESGGGLVQPGGSLRLSCAASGFTFRSQQASWVRRAPGKGLEWVSAISGSGGSTYYADSVKGRFTISRDNSKNTLYLQMNSLRAEDTAVYYCAKGGDYGGNYFDYWGQGTLVTVSS |
| 34 | AM-8-VH | EVQLVESGGGLVQPGGSLRLSCAASGFTFTTQQASWVRRAPGKGLEWVSAISGSGGSTYYADSVKGRFTISRDNSKNTLYLQMNSLRAEDTAVYYCAKGGDYGGNYFDYWGQGTLVTVSS |
| 35 | AM-9-VH | EVQLVESGGGLVQPGGSLRLSCAASGFTFGGQQASWVRRAPGKGLEWVSAISGSGGSTYYADSVKGRFTISRDNSKNTLYLQMNSLRAEDTAVYYCAKGGDYGGNYFDYWGQGTLVTVSS |
| 36 | BADD197-1181 VL | EIVLTQSPGTLSLSPGERATLSCRASQSVSSYLAWYQQKPGQAPRLLIYGASSRATGIPDRFSGSGSGTDFTLTISRLEPEDFAVYYCQQYGSSPLTFGGGTKVEIK |
| 37 | BADD412-2513 VL | EIVLTQSPGTLSLSPGERATLSCRASQSVSSYLAWYQQKPGQAPRLLIYGASSRATGIPDRFSGSGSGTDFTLTISRLEPEDFAVYYCQQYGSSPLTFGGGTKVEIK |

TABLE 1-continued

Amino acid sequences of exemplary anti-TIM-3 antibodies.

| SEQ ID NO: | Description* | Amino acid sequence |
|---|---|---|
| 38 | BADD456-2928 VL | DIQMTQSPSSLSASVGDRVTITCRASQGISNYLAWYQQKPGKVPKLLIYAASTLQSGVPSRFSGSGSGTDFTLTISRLEPEDFAVYYCQQYGSSPLTFGGGTKVEIK |
| 39 | BADD466-3164 VL | EIVLTQSPATLSLSPGERATLSCRASQSVSSYLAWYQQKPGQAPRLLIYGASSRATGIPDRFSGSGSGTDFTLTISRLEPEDFAVYYCQQYGSSPLTFGGGTKVKIK |
| 40 | BADD466-3165 VL | EIVLTQSPATLSLSPGERATLSCRASQSVSSYLAWYQQKPGQAPRLLIYGASTRATGIPARFSGSGSGTDFTLTISRLEPEDFAVYYCQQYGSSPLTFGGGTKVEIK |
| 41 | BADD466-3166 VL | EIVLTQSPGTLSLSPGERATLSCRASQSVSSYLAWYQQKPGQAPRLLIYDASSRATGIPDRFSGSGSGTDFTLTISRLEPEDFAVYYCQQYGSSPLTFGGGTKVEIK |
| 42 | BADD466-3167 VL | EIVLTQSPATLSLSPGERATLSCRASQSVSSYLAWYQQKPGQAPRLLIYDASNRATGIPARFSGSGSGTDFTLTISRLEPEDFAVYYCQQYGSSPLTFGGGTKVEIK |
| 43 | BADD466-3168 VL | EIVLTQSPGTLSLSPGERATLSCRASQSVSSYLAWYQQKPGQAPRLLIYDASNRATGIPARFSGSGSGTDFTLTISRLEPEDFAVYYCQQYGSSPLTFGGGTKVEIK |
| 44 | BADD466-3169 VL | EIVLTQSPATLSLSPGERATLSCGASQSVSSSYLAWYQQKPGLAPRLLIYDASSRATGIPDRFSGSGSGTDFTLTISRLEPEDFAVYYCQQYGSSPLTFGGGTKVEIK |
| 45 | BADD466-3170 VL | EIVLTQSPATLSLSPGERATLSCRASQSVSSYLAWYQQKPGQAPRLLIYDASNRATGIPARFSGSGSGTDFTLTISSLEPEDFAVYYCQQYGSSPLTFGGGTKVEIK |
| 46 | BADD466-3171 VL | EIVLTQSPATLSLSPGERATLSCRASQSVSSYLAWYQQKPGQAPRLLIYDASNRATGIPASFSGSGSGTDFTLTISRLEPEDFAVYYCQQYGSSPLTFGGGTKVEIK |
| 47 | BADD466-3172 | VLEIVLTQSPGTLSLSPGERATLSCRASQSVSSYLAWYQQKPGQAPRLLIYGASSRATGIPARFSGSGSGTDFTLTISRLEPEDFAVYYCQQYGSSPITFGGGTKVEIK |
| 48 | CDRH1 consensus sequence 1 | $X_1X_2X_3X_4X_5S$, wherein:<br>$X_1$ is R, S, A, G, K, M, or T;<br>$X_2$ is Q, S, A, G, R, or T;<br>$X_3$ is N, Y, G, or Q;<br>$X_4$ is A or Q; and<br>$X_5$ is W, M, A, S, or T |
| 49 | CDRH1 consensus sequence 2 | $X_1X_2$NAWS, wherein:<br>$X_1$ is R or A; and<br>$X_2$ is Q or R |
| 50 | CDRH1 consensus sequence 3 | $X_1X_2GQX_3S$, wherein:<br>$X_1$ is K, M, or G;<br>$X_2$ is A or S; and<br>$X_3$ is S or T |
| 51 | CDRH1 consensus sequence 4 | $X_1X_2$QQAS, wherein:<br>$X_1$ is S, R, T, or G; and<br>$X_2$ is A, S, T, or G |
| 52 | CDRL1 consensus sequence | $X_1$ASQSV$X_2$SSYLA, wherein<br>$X_1$ is R or G; and<br>$X_2$ is absent or S |

TABLE 1-continued

Amino acid sequences of exemplary anti-TIM-3 antibodies.

| SEQ ID NO: | Description* | Amino acid sequence |
|---|---|---|
| 53 | CDRL2 consensus sequence | $X_1ASX_2RAT$, wherein:<br>$X_1$ is D or G; and<br>$X_2$ is N, S, or T |
| 54 | CDRL3 consensus sequence | $QQYGSSPX_1T$, wherein<br>$X_1$ is L or I |
| 55 | VH consensus sequence | EVQLVESGGGLVQPX$_1$GSLRLSCAASGFTF<br>X$_2$X$_3$X$_4$X$_5$X$_6$SWVRX$_7$APGKGLEWVSAISGSGGSTY<br>YADSVKGRFTISRDNSKNTLYLQMNSLRAEDTAV<br>YYCAKGGDYGGNYFDYWGQGTLVTVSS,<br>wherein:<br>$X_1$ is G or R;<br>$X_2$ is R, S, A, G, K, M, or T;<br>$X_3$ is Q, S, A, G, R, or T;<br>$X_4$ is N, Y, G, or Q;<br>$X_5$ is A or Q;<br>$X_6$ is W, M, A, S, or T; and<br>$X_7$ is R or Q |
| 56 | VL consensus sequence | EIVLTQSPX$_1$TLSLSPGERATLSCX$_2$ASQSVX$_3$SSYL<br>AWYQQKPGX$_4$APRLLIYX$_5$ASX$_6$RATGIPX$_7$X$_8$FSGS<br>GSGTDFTLTISX$_9$LEPEDFAVYYCQQYGSSPX$_{10}$TFG<br>GGTKVX$_{11}$IK, wherein:<br>$X_1$ is A or G;<br>$X_2$ is R or G;<br>$X_3$ is absent or S;<br>$X_4$ is Q or L;<br>$X_5$ is D or G;<br>$X_6$ is N, S, or T;<br>$X_7$ is A or D;<br>$X_8$ is S or R;<br>$X_9$ is R or S;<br>$X_{10}$ is L or I; and<br>$X_{11}$ is E or K |
| 57 | pab2188 full length IgG$_1$ heavy chain | EVQLVESGGGLVQPGGSLRLSCAASGFTFSSYAM<br>SWVRRAPGKGLEWVSAISGSGGSTYYADSVKGR<br>FTISRDNSKNTLYLQMNSLRAEDTAVYYCAKGGD<br>YGGNYFDYWGQGTLVTVSSASTKGPSVFPLAPSS<br>KSTSGGTAALGCLVKDYFPEPVTVSWNSGALTSG<br>VHTFPAVLQSSGLYSLSSVVTVPSSSLGTQTYICN<br>VNHKPSNTKVDKRVEPKSCDKTHTCPPCPAPELL<br>GGPSVFLFPPKPKDTLMISRTPEVTCVVVDVSHED<br>PEVKFNWYVDGVEVHNAKTKPREEQYNSTYRVV<br>SVLTVLHQDWLNGKEYKCKVSNKALPAPIEKTIS<br>KAKGQPREPQVYTLPPSREEMTKNQVSLTCLVKG<br>FYPSDIAVEWESNGQPENNYKTTPPVLDSDGSFFL<br>YSKLTVDKSRWQQGNVFSCSVMHEALHNHYTQK<br>SLSLSPG |
| 58 | pab2188 full length IgG$_1$ N297A heavy chain | EVQLVESGGGLVQPGGSLRLSCAASGFTFSSYAM<br>SWVRRAPGKGLEWVSAISGSGGSTYYADSVKGR<br>FTISRDNSKNTLYLQMNSLRAEDTAVYYCAKGGD<br>YGGNYFDYWGQGTLVTVSSASTKGPSVFPLAPSS<br>KSTSGGTAALGCLVKDYFPEPVTVSWNSGALTSG<br>VHTFPAVLQSSGLYSLSSVVTVPSSSLGTQTYICN<br>VNHKPSNTKVDKRVEPKSCDKTHTCPPCPAPELL<br>GGPSVFLFPPKPKDTLMISRTPEVTCVVVDVSHED<br>PEVKFNWYVDGVEVHNAKTKPREEQYASTYRVV<br>SVLTVLHQDWLNGKEYKCKVSNKALPAPIEKTIS<br>KAKGQPREPQVYTLPPSREEMTKNQVSLTCLVKG<br>FYPSDIAVEWESNGQPENNYKTTPPVLDSDGSFFL<br>YSKLTVDKSRWQQGNVFSCSVMHEALHNHYTQK<br>SLSLSPG |
| 59 | pab2188 full length IgG$_4$ S228P heavy chain | EVQLVESGGGLVQPGGSLRLSCAASGFTFSSYAM<br>SWVRRAPGKGLEWVSAISGSGGSTYYADSVKGR<br>FTISRDNSKNTLYLQMNSLRAEDTAVYYCAKGGD<br>YGGNYFDYWGQGTLVTVSSASTKGPSVFPLAPCS<br>RSTSESTAALGCLVKDYFPEPVTVSWNSGALTSG<br>VHTFPAVLQSSGLYSLSSVVTVPSSSLGTKTYTCN<br>VDHKPSNTKVDKRVESKYGPPCPPCPAPEFLGGPS<br>VFLFPPKPKDTLMISRTPEVTCVVVDVSQEDPEVQ<br>FNWYVDGVEVHNAKTKPREEQFNSTYRVVSVLT |

TABLE 1-continued

Amino acid sequences of exemplary anti-TIM-3 antibodies.

| SEQ ID NO: | Description* | Amino acid sequence |
|---|---|---|
| | | VLHQDWLNGKEYKCKVSNKGLPSSIEKTISKAKG QPREPQVYTLPPSQEEMTKNQVSLTCLVKGFYPS DIAVEWESNGQPENNYKTTPPVLDSDGSFFLYSRL TVDKSRWQEGNVFSCSVMHEALHNHYTQKSLSL SLG |
| 60 | AM-1 full length IgG$_1$ N297A heavy chain | EVQLVESGGGLVQPGGSLRLSCAASGFTFKAGQS SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 61 | AM-2 full length IgG$_1$ N297A heavy chain | EVQLVESGGGLVQPGGSLRLSCAASGFTFRQNAW SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 62 | AM-3 full length IgG$_1$ N297A heavy chain | EVQLVESGGGLVQPGGSLRLSCAASGFTFMSGQT SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 63 | AM-4 full length IgG$_1$ N297A heavy chain | EVQLVESGGGLVQPGGSLRLSCAASGFTFGAGQS SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 64 | AM-5 full length IgG$_1$ N297A heavy chain | EVQLVESGGGLVQPGGSLRLSCAASGFTFSAQQA SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV |

TABLE 1-continued

Amino acid sequences of exemplary anti-TIM-3 antibodies.

| SEQ ID NO: | Description* | Amino acid sequence |
|---|---|---|
| | | SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 65 | AM-6 full length IgG₁ N297A heavy chain | EVQLVESGGGLVQPGGSLRLSCAASGFTFARNAW SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 66 | AM-7 full length IgG₁ N297A heavy chain | EVQLVESGGGLVQPGGSLRLSCAASGFTFRSQQA SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 67 | AM-8 full length IgG₁ N297A heavy chain | EVQLVESGGGLVQPGGSLRLSCAASGFTFTTQQA SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 68 | AM-9 full length IgG₁ N297A heavy chain | EVQLVESGGGLVQPGGSLRLSCAASGFTFGGQQA SWVRRAPGKGLEWVSAISGSGGSTYYADSVKGR FTISRDNSKNTLYLQMNSLRAEDTAVYYCAKGGD YGGNYFDYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYICN VNHKPSNTKVDKRVEPKSCDKTHTCPPCPAPELL GGPSVFLFPPKPKDTLMISRTPEVTCVVVDVSHED PEVKFNWYVDGVEVHNAKTKPREEQYASTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFFL YSKLTVDKSRWQQGNVFSCSVMHEALHNHYTQK SLSLSPG |
| 69 | BADD466-3171 full length light chain sequence | EIVLTQSPATLSLSPGERATLSCRASQSVSSYLAW YQQKPGQAPRLLIYDASNRATGIPASFSGSGSGTD FTLTISRLEPEDFAVYYCQQYGSSPLTFGGGTKVEI KRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC |

TABLE 1-continued

Amino acid sequences of exemplary anti-TIM-3 antibodies.

| SEQ ID NO: | Description* | Amino acid sequence |
|---|---|---|
| 70 | Human Ig$_1$ G1m3 allotype (without C-terminal lysine) | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPG |
| 71 | Human IgG$_1$ G1m3 allotype | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPGK |
| 72 | IgG$_1$ N297A (without C-terminal lysine) | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISRT PEVTCVVVDVSHEDPEVKFNWYVDGVEVHNAKT KPREEQYASTYRVVSVLTVLHQDWLNGKEYKCK VSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPG |
| 73 | IgG$_1$ N297A | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISRT PEVTCVVVDVSHEDPEVKFNWYVDGVEVHNAKT KPREEQYASTYRVVSVLTVLHQDWLNGKEYKCK VSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPGK |
| 74 | IgG$_4$ S228P (without C-terminal lysine) | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKYG PPCPPCPAPEFLGGPSVFLFPPKPKDTLMISRTPEV TCVVVDVSQEDPEVQFNWYVDGVEVHNAKTKPR EEQFNSTYRVVSVLTVLHQDWLNGKEYKCKVSN KGLPSSIEKTISKAKGQPREPQVYTLPPSQEEMTK NQVSLTCLVKGFYPSDIAVEWESNGQPENNYKTT PPVLDSDGSFFLYSRLTVDKSRWQEGNVFSCSVM HEALHNHYTQKSLSLSLG |
| 75 | IgG$_4$ S228P | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKYG PPCPPCPAPEFLGGPSVFLFPPKPKDTLMISRTPEV TCVVVDVSQEDPEVQFNWYVDGVEVHNAKTKPR EEQFNSTYRVVSVLTVLHQDWLNGKEYKCKVSN KGLPSSIEKTISKAKGQPREPQVYTLPPSQEEMTK NQVSLTCLVKGFYPSDIAVEWESNGQPENNYKTT PPVLDSDGSFFLYSRLTVDKSRWQEGNVFSCSVM HEALHNHYTQKSLSLSLGK |
| 76 | Human kappa light chain constant region IGKC*01 Km3 allotype | RTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSF NRGEC |
| 77 | Human kappa light chain constant region IGKC*01 | RSVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSF |

TABLE 1-continued

Amino acid sequences of exemplary anti-TIM-3 antibodies.

| SEQ ID NO: | Description* | Amino acid sequence |
|---|---|---|
| | Km3 allotype (with T109S mutation) | NRGEC |
| 84 | IGHV3-23*04 | QVQLVESGGGLVQPGGSLRLSCAASGFTFSSYAM SWVRQAPGKGLEWVSAISGSGGSTYYADSVKGR FTISRDNSKNTLYLQMNSLRAEDTAVYYCAK |
| 85 | IGKV1-27*01 | DIQMTQSPSSLSASVGDRVTITCRASQGISNYLAW YQQKPGKVPKLLIYAASTLQSGVPSRFSGSGSGTD FTLTISSLQPEDVATYYCQKYNSAP |
| 86 | IGKV3-11*01 | EIVLTQSPATLSLSPGERATLSCRASQSVSSYLAW YQQKPGQAPRLLIYDASNRATGIPARFSGSGSGTD FTLTISSLEPEDFAVYYCQQRSNWP |
| 87 | IGKV3-20*01 | EIVLTQSPGTLSLSPGERATLSCRASQSVSSSYLA WYQQKPGQAPRLLIYGASSRATGIPDRFSGSGSGT DFTLTISRLEPEDFAVYYCQQYGSSP |
| 88 | IGKV3D-20*01 | EIVLTQSPATLSLSPGERATLSCGASQSVSSSYLA WYQQKPGLAPRLLIYDASSRATGIPDRFSGSGSGT DFTLTISRLEPEDFAVYYCQQYGSSP |

*Heavy chain CDRs are defined according to the MacCallum numbering system and light chain CDRs are defined according to the Kabat numbering system.

TABLE 2

Heavy chain CDR amino acid sequences of exemplary anti-TIM-3 antibodies.

| VH | CDRH1* | SEQ ID NO: | CDRH2* | SEQ ID NO: | CDRH3* | SEQ ID NO: |
|---|---|---|---|---|---|---|
| BADD456-2919 | SSYAMS | 1 | WVSAISGSGGSTY | 2 | AKGGDYGGNYFD | 3 |
| BADD466-3162 | SSYAMS | 1 | WVSAISGSGGSTY | 2 | AKGGDYGGNYFD | 3 |
| BADD466-3163 | SSYAMS | 1 | WVSAISGSGGSTY | 2 | AKGGDYGGNYFD | 3 |
| AM-1 | KAGQSS | 4 | WVSAISGSGGSTY | 2 | AKGGDYGGNYFD | 3 |
| AM-2 | RQNAWS | 5 | WVSAISGSGGSTY | 2 | AKGGDYGGNYFD | 3 |
| AM-3 | MSGQTS | 6 | WVSAISGSGGSTY | 2 | AKGGDYGGNYFD | 3 |
| AM-4 | GAGQSS | 7 | WVSAISGSGGSTY | 2 | AKGGDYGGNYFD | 3 |
| AM-5 | SAQQAS | 8 | WVSAISGSGGSTY | 2 | AKGGDYGGNYFD | 3 |
| AM-6 | ARNAWS | 9 | WVSAISGSGGSTY | 2 | AKGGDYGGNYFD | 3 |
| AM-7 | RSQQAS | 10 | WVSAISGSGGSTY | 2 | AKGGDYGGNYFD | 3 |
| AM-8 | TTQQAS | 11 | WVSAISGSGGSTY | 2 | AKGGDYGGNYFD | 3 |
| AM-9 | GGQQAS | 12 | WVSAISGSGGSTY | 2 | AKGGDYGGNYFD | 3 |

*Defined according to the MacCallum numbering system.

TABLE 3

Light chain CDR amino acid sequences of exemplary anti-TIM-3 antibodies.

| VL | CDRL1* | SEQ ID NO: | CDRL2* | SEQ ID NO: | CDRL3* | SEQ ID NO: |
|---|---|---|---|---|---|---|
| BADD197-1181 | RASQSVSSSYLA | 13 | GASSRAT | 17 | QQYGSSPLT | 22 |
| BADD412-2513 | RASQSVSSYLA | 14 | GASSRAT | 17 | QQYGSSPLT | 22 |
| BADD456-2928 | RASQGISNYLA | 15 | AASTLQS | 18 | QQYGSSPLT | 22 |
| BADD466-3164 | RASQSVSSYLA | 14 | GASSRAT | 17 | QQYGSSPLT | 22 |
| BADD466-3165 | RASQSVSSYLA | 14 | GASTRAT | 19 | QQYGSSPLT | 22 |
| BADD466-3166 | RASQSVSSYLA | 14 | DASSRAT | 20 | QQYGSSPLT | 22 |
| BADD466-3167 | RASQSVSSYLA | 14 | DASNRAT | 21 | QQYGSSPLT | 22 |
| BADD466-3168 | RASQSVSSYLA | 14 | DASNRAT | 21 | QQYGSSPLT | 22 |
| BADD466-3169 | GASQSVSSSYLA | 16 | DASSRAT | 20 | QQYGSSPLT | 22 |
| BADD466-3170 | RASQSVSSYLA | 14 | DASNRAT | 21 | QQYGSSPLT | 22 |
| BADD466-3171 | RASQSVSSYLA | 14 | DASNRAT | 21 | QQYGSSPLT | 22 |
| BADD466-3172 | RASQSVSSYLA | 14 | GASSRAT | 17 | QQYGSSPIT | 23 |

*Defined according to the Kabat numbering system.

TABLE 4

Exemplary anti-TIM-3 antibodies.

| Antibody | Heavy chain variable region | SEQ ID NO: | Light chain variable region | SEQ ID NO: |
|---|---|---|---|---|
| pab2085 | BADD456-2919 | 24 | BADD197-1181 | 36 |
| pab2088 | BADD456-2919 | 24 | BADD456-2928 | 38 |
| pab2173 | BADD466-3163 | 26 | BADD466-3167 | 42 |
| pab2174 | BADD456-2919 | 24 | BADD466-3167 | 42 |
| pab2175 | BADD456-2919 | 24 | BADD466-3171 | 46 |
| pab2176 | BADD456-2919 | 24 | BADD466-3168 | 43 |
| pab2177 | BADD466-3163 | 26 | BADD466-3168 | 43 |
| pab2178 | BADD466-3163 | 26 | BADD466-3171 | 46 |
| pab2179 | BADD466-3163 | 26 | BADD466-3166 | 41 |
| pab2180 | BADD456-2919 | 24 | BADD466-3166 | 41 |
| pab2181 | BADD466-3162 | 25 | BADD466-3164 | 39 |
| pab2182 | BADD456-2919 | 24 | BADD466-3172 | 47 |
| pab2183 | BADD466-3162 | 25 | BADD466-3165 | 40 |
| pab2184 | BADD466-3163 | 26 | BADD466-3172 | 47 |
| pab2185 | BADD466-3162 | 25 | BADD412-2513 | 37 |
| pab2186 | BADD466-3162 | 25 | BADD466-3170 | 45 |
| pab2187 | BADD466-3162 | 25 | BADD466-3169 | 44 |
| pab2188 | BADD466-3162 | 25 | BADD466-3171 | 46 |
| pab2189 | BADD466-3162 | 25 | BADD466-3167 | 42 |
| pab2190 | BADD466-3162 | 25 | BADD466-3166 | 41 |
| pab2191 | BADD466-3162 | 25 | BADD466-3168 | 43 |
| pab2192 | BADD466-3162 | 25 | BADD466-3172 | 47 |
| AM-1 | AM-1-VH | 27 | BADD466-3171 | 46 |
| AM-2 | AM-2-VH | 28 | BADD466-3171 | 46 |
| AM-3 | AM-3-VH | 29 | BADD466-3171 | 46 |
| AM-4 | AM-4-VH | 30 | BADD466-3171 | 46 |
| AM-5 | AM-5-VH | 31 | BADD466-3171 | 46 |
| AM-6 | AM-6-VH | 32 | BADD466-3171 | 46 |
| AM-7 | AM-7-VH | 33 | BADD466-3171 | 46 |
| AM-8 | AM-8-VH | 34 | BADD466-3171 | 46 |
| AM-9 | AM-9-VH | 35 | BADD466-3171 | 46 |

TABLE 5

Closest germline genes.

| Heavy chain or light chain variable region | Closest germline gene | SEQ ID NO for germline gene: |
|---|---|---|
| BADD456-2919 VH | IGHV3-23*04 | 84 |
| BADD466-3162 VH | IGHV3-23*04 | 84 |
| BADD466-3163 VH | IGHV3-23*04 | 84 |
| AM-1-VH | IGHV3-23*04 | 84 |
| AM-2-VH | IGHV3-23*04 | 84 |
| AM-3-VH | IGHV3-23*04 | 84 |
| AM-4-VH | IGHV3-23*04 | 84 |
| AM-5-VH | IGHV3-23*04 | 84 |
| AM-6-VH | IGHV3-23*04 | 84 |
| AM-7-VH | IGHV3-23*04 | 84 |
| AM-8-VH | IGHV3-23*04 | 84 |
| AM-9-VH | IGHV3-23*04 | 84 |
| BADD197-1181 VL | IGKV3-20*01 | 87 |
| BADD412-2513 VL | IGKV3-20*01 | 87 |
| BADD456-2928 VL | IGKV1-27*01 | 85 |
| BADD466-3164 VL | IGKV3-20*01 | 87 |
| BADD466-3165 VL | IGKV3-20*01 | 87 |
| BADD466-3166 VL | IGKV3-20*01 | 87 |
| BADD466-3167 VL | IGKV3-11*01 | 86 |
| BADD466-3168 VL | IGKV3-20*01 | 87 |
| BADD466-3169 VL | IGKV3D-20*01 | 88 |
| BADD466-3170 VL | IGKV3-11*01 | 86 |
| BADD466-3171 VL | IGKV3-11*01 | 86 |
| BADD466-3172 VL | IGKV3-20*01 | 87 |

TABLE 6

Exemplary sequences of TIM-3.

| SEQ ID NO: | Description* | Amino acid Sequence |
|---|---|---|
| 78 | Human TIM-3 immature protein (Q8TDQ0-1) | MFSHLPFDCVLLLLLLLLTRSSEVEYRAEVGQNA YLPCFYTPAAPGNLVPVCWGKGACPVFECGNVV LRTDERDVNYWTSRYWLNGDFRKGDVSLTIENV TLADSGIYCCRIQIPGIMNDEKFNLKLVIKPAKVTP APTQRDFTAAFPRMLTTRGHGPAETQTLGSLPDI NLTQISTLANELRDSRLANDLRDSGATIRIGIYIGA GICAGLALALIFGALIFKWYSHSKEKIQNLSLISLA NLPPSGLANAVAEGIRSEENIYTIEENVYEVEEPNE YYCYVSSRQQPSQPLGCRFAMP |
| 79 | Human TIM-3 mature protein | SEVEYRAEVGQNAYLPCFYTPAAPGNLVPVCWG KGACPVFECGNVVLRTDERDVNYWTSRYWLNG DFRKGDVSLTIENVTLADSGIYCCRIQIPGIMNDEK FNLKLVIKPAKVTPAPTQRDFTAAFPRMLTTRG HGPAETQTLGSLPDINLTQISTLANELRDSRLAND LRDSGATIRIGIYIGAGICAGLALALIFGALIFKWYS HSKEKIQNLSLISLANLPPSGLANAVAEGIRSEENI YTIEENVYEVEEPNEYYCYVSSRQQPSQPLGCRFA MP |
| 101 | Human TIM-3 F40A | SEVEYRAEVGQNAYLPCFYTPAAPGNLVPVCWG KGACPVAECGNVVLRTDERDVNYWTSRYWLNG DFRKGDVSLTIENVTLADSGIYCCRIQIPGIMNDEK FNLKLVIKPAKVTPAPTQRDFTAAFPRMLTTRG HGPAETQTLGSLPDINLTQISTLANELRDSRLAND LRDSGATIRIGIYIGAGICAGLALALIFGALIFKWYS HSKEKIQNLSLISLANLPPSGLANAVAEGIRSEENI YTIEENVYEVEEPNEYYCYVSSRQQPSQPLGCRFA MP |
| 102 | Human TIM-3 fragment | SEVEYRAEVGQNAYLPCFYTPAAPGNLVPVCWG KGACPVFECGNVVLRTDERDVNYWTSRYWLNG DFRKGDVSLTIENVTLADGIYCCRIQIPGIMNDEK FNLKLVIKPAKVTPAPTQRDFTAAFPRMLTTRG HGPAETQTLGSLPDINLTQISTLANELRDSRLAND LRDSGATIR |
| 93 | TIM-3 epitope | PVFECGN |
| 94 | TIM-3 epitope | VCWGKGACPVFECGNVVL |
| 95 | TIM-3 epitope | RIQIPGIMND |
| 96 | TIM-3 epitope | RIQIPGIMNDEKFNLKL |
| 97 | TIM-3 epitope | EKFNLKL |
| 98 | TIM-3 epitope | PAAPGNLVP |
| 99 | TIM-3 epitope | GKGACPVFE |
| 100 | TIM-3 epitope | DFTAAFPR |

In certain embodiments, the instant disclosure provides an isolated antibody that specifically binds to TIM-3 (e.g., human TIM-3), the antibody comprising a VH domain comprising one, two, or all three of the CDRs of a VH domain set forth in Table 1 herein. In certain embodiments, the antibody comprises the CDRH1 of one of VH domains set forth in Table 1. In certain embodiments, the antibody comprises the CDRH2 of one of the VH domains set forth in Table 1. In certain embodiments, the antibody comprises the CDRH3 of one of the VH domains set forth in Table 1.

In certain embodiments, the instant disclosure provides an isolated antibody that specifically binds to TIM-3 (e.g., human TIM-3), the antibody comprising a VL domain comprising one, two, or all three of the CDRs of a VL domain disclosed in Table 1 herein. In certain embodiments, the antibody comprises the CDRL1 of one of VL domains set forth in Table 1. In certain embodiments, the antibody comprises the CDRL2 of one of the VL domains set forth in Table 1. In certain embodiments, the antibody comprises the CDRL3 of one of the VL domains set forth in Table 1.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety. In certain embodiments, the heavy chain CDRs of an antibody are determined according to MacCallum and the light chain CDRs of an antibody are determined according to a different method.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety. In certain embodiments, the light chain CDRs of an antibody are determined according to Kabat and the heavy chain CDRs of an antibody are determined according to MacCallum (supra).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to TIM-3 (e.g., human TIM-3), the antibody comprising the Chothia VH CDRs of a VH disclosed in Table 1 herein. In certain embodiments, the instant disclosure provides an isolated antibody that specifically binds to TIM-3 (e.g., human TIM-3), the antibody comprising the Chothia VL CDRs of a VL disclosed in Table 1 herein. In certain embodiments, the instant disclosure provides an isolated antibody that specifically binds to TIM-3 (e.g., human TIM-3), the antibody comprising the Chothia VH CDRs and Chothia VL CDRs of an antibody disclosed in Table 1 herein. In certain embodiments, antibodies that specifically bind to TIM-3 (e.g., human TIM-3) comprise one or more CDRs, in which the Chothia and Kabat CDRs have the same amino acid sequence. In certain embodiments, the instant disclosure provides an isolated antibody that specifically binds to TIM-3 (e.g., human TIM-3) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the instant disclosure provides antibodies that specifically bind to TIM-3 (e.g., human TIM-3) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to TIM-3 (e.g., human TIM-3) and comprise CDRs of an antibody disclosed in Table 1 herein as determined by the AbM numbering scheme.

In certain embodiments, the instant disclosure provides an isolated antibody that specifically binds to TIM-3 (e.g., human TIM-3), wherein the antibody comprises a heavy chain variable region comprising the CDRH1, CDRH2, and CDRH3 region amino acid sequences of a VH domain set forth in SEQ ID NO: 24, 25, 26, 27, 28, 29, 30, 31, 32, 33, 34, or 35, and a light chain variable region comprising the CDRL1, CDRL2, and CDRL3 region amino acid sequences of a VL domain set forth in SEQ ID NO: 36, 37, 38, 39, 40, 41, 42, 43, 44, 45, 46, or 47, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the instant disclosure provides an isolated antibody that specifically binds to TIM-3 (e.g., human TIM-3), the antibody comprising:
(a) a CDRH1 comprises the amino acid sequence of $X_1X_2X_3X_4X_5S$ (SEQ ID NO: 48), wherein
  $X_1$ is R, S, A, G, K, M, or T,
  $X_2$ is Q, S, A, G, R, or T,
  $X_3$ is N, Y, G, or Q,
  $X_4$ is A or Q, and
  $X_5$ is W, M, A, S, or T; and/or
(b) a CDRH2 comprises the amino acid sequence of WVSAISGSGGSTY (SEQ ID NO: 2); and/or
(c) a CDRH3 comprises the amino acid sequence of AKGGDYGGNYFD (SEQ ID NO: 3); and/or
(d) a CDRL1 comprises the amino acid sequence of $X_1ASQSVX_2SSYLA$ (SEQ ID NO: 52), wherein
  $X_1$ is R or G, and
  $X_2$ is absent or S; and/or
(e) a CDRL2 comprises the amino acid sequence of $X_1ASX_2RAT$ (SEQ ID NO: 53), wherein
  $X_1$ is D or G, and
  $X_2$ is N, S, or T; and/or
(f) a CDRL3 comprises the amino acid sequence of $QQYGSSPX_1T$ (SEQ ID NO: 54),
  wherein $X_1$ is L or I.

In certain embodiments, CDRH1 comprises the amino acid sequence of $X_1X_2NAWS$ (SEQ ID NO: 49), wherein: $X_1$ is R or A; and $X_2$ is Q or R. In certain embodiments, CDRH1 comprises the amino acid sequence of $X_1X_2GQX_3S$ (SEQ ID NO: 50), wherein: $X_1$ is K, M, or G; $X_2$ is A or S; and $X_3$ is S or T. In certain embodiments, CDRH1 comprises the amino acid sequence of $X_1X_2QQAS$ (SEQ ID NO: 51), wherein: $X_1$ is S, R, T, or G; and $X_2$ is A, S, T, or G. In certain embodiments, CDRH1 comprises an amino acid sequence selected from the group consisting of SEQ ID NOs: 1, and 4-12. In certain embodiments, CDRL1 comprises an amino acid sequence selected from the group consisting of SEQ ID NOs: 13-16. In certain embodiments, CDRL2 comprises an amino acid sequence selected from the group consisting of SEQ ID NOs: 17-21. In certain embodiments, CDRL3 comprises an amino acid sequence selected from the group consisting of SEQ ID NOs: 22 and 23.

In certain embodiments, the instant disclosure provides an isolated antibody that specifically binds to TIM-3 (e.g., human TIM-3), wherein the antibody comprises a VH domain comprising the CDRH1, CDRH2 and CDRH3 amino acid sequences set forth in SEQ ID NOs: 1, 2, and 3; 4, 2, and 3; 5, 2, and 3; 6, 2, and 3; 7, 2, and 3; 8, 2, and 3; 9, 2, and 3; 10, 2, and 3; 11, 2, and 3; or 12, 2, and 3, respectively. In certain embodiments, the instant disclosure provides an isolated antibody that specifically binds to TIM-3 (e.g., human TIM-3), wherein the antibody comprises a VH domain comprising the CDRH1, CDRH2 and CDRH3 amino acid sequences set forth in SEQ ID NOs: 1, 2, and 3, respectively. In certain embodiments, the instant disclosure provides an isolated antibody that specifically binds to TIM-3 (e.g., human TIM-3), wherein the antibody comprises a VH domain comprising the CDRH1, CDRH2 and CDRH3 amino acid sequences set forth in SEQ ID NOs: 5, 2, and 3, respectively. In certain embodiments, the instant disclosure provides an isolated antibody that specifically binds to TIM-3 (e.g., human TIM-3), wherein the antibody comprises a VH domain comprising the CDRH1, CDRH2 and CDRH3 amino acid sequences set forth in SEQ ID NOs: 9, 2, and 3, respectively.

In certain embodiments, the instant disclosure provides an isolated antibody that specifically binds to TIM-3 (e.g., human TIM-3), wherein the antibody comprises a VL domain comprising the CDRL1, CDRL2 and CDRL3 amino acid sequences set forth in SEQ ID NOs: 13, 17, and 22; 14, 17, and 22; 15, 18, and 22; 14, 19, and 22; 14, 20, and 22; 14, 21, and 22; 16, 20, and 22; or 14, 17, and 23, respectively. In certain embodiments, the instant disclosure provides an isolated antibody that specifically binds to TIM-3 (e.g., human TIM-3), wherein the antibody comprises a VL domain comprising the CDRL1, CDRL2 and CDRL3 amino acid sequences set forth in SEQ ID NOs: 14, 21, and 22, respectively.

In certain embodiments, the instant disclosure provides an isolated antibody that specifically binds to TIM-3 (e.g., human TIM-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 14, 21, and 22; 4, 2, 3, 14, 21, and 22; 5, 2, 3, 14, 21, and 22; 6, 2, 3, 14, 21, and 22; 7, 2, 3, 14, 21, and 22; 8, 2, 3, 14, 21, and 22; 9, 2, 3, 14, 21, and 22; 10, 2, 3, 14, 21, and 22; 11, 2, 3, 14, 21, and 22; or 12, 2, 3, 14, 21, and 22, respectively. In certain embodiments, the instant disclosure provides an isolated antibody that specifically binds to TIM-3 (e.g., human TIM-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 14, 21, and 22, respectively. In certain embodiments, the instant disclosure provides an isolated antibody that specifically binds to TIM-3 (e.g., human TIM-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 5, 2, 3, 14, 21, and 22, respectively. In certain embodiments, the instant disclosure provides an isolated antibody that specifically binds to TIM-3 (e.g., human TIM-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 9, 2, 3, 14, 21, and 22.

In certain embodiments, the instant disclosure provides an isolated antibody that specifically binds to TIM-3 (e.g., human TIM-3), comprising a heavy chain variable region comprising an amino acid sequence of SEQ ID NO: 55. In certain embodiments, the instant disclosure provides an isolated antibody that specifically binds to TIM-3 (e.g., human TIM-3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 24, 25, 26, 27, 28, 29, 30, 31, 32, 33, 34, or 35. In certain embodiments, the antibody comprises a heavy chain variable region having the amino acid sequence set forth in SEQ ID NO: 24, 25, 26, 27, 28, 29, 30, 31, 32, 33, 34, or 35. In certain embodiments, the antibody comprises a heavy chain variable region having the amino acid sequence set forth in SEQ ID NO: 24. In certain embodiments, the antibody comprises a heavy chain variable region having the amino acid sequence set forth in SEQ ID NO: 25. In certain embodiments, the antibody comprises a heavy chain variable region having the amino acid sequence set forth in SEQ ID NO: 26. In certain embodiments, the antibody comprises a heavy chain variable region having the amino acid sequence set forth in SEQ ID NO: 27. In certain embodiments, the antibody comprises a heavy chain variable region having the amino acid sequence set forth in SEQ ID NO: 28. In certain embodiments, the antibody comprises a heavy chain variable region having the amino acid sequence set forth in SEQ ID NO: 29. In certain embodiments, the antibody comprises a heavy chain variable region having the amino acid sequence set forth in SEQ ID NO: 30. In certain embodiments, the antibody comprises a heavy chain variable region having the amino acid sequence set forth in SEQ ID NO: 31. In certain embodiments, the antibody comprises a heavy chain variable region having the amino acid sequence set forth in SEQ ID NO: 32. In certain embodiments, the antibody comprises a heavy chain variable region having the amino acid sequence set forth in SEQ ID NO: 33. In certain embodiments, the antibody comprises a heavy chain variable region having the amino acid sequence set forth in SEQ ID NO: 34. In certain embodiments, the antibody comprises a heavy chain variable region having the amino acid sequence set forth in SEQ ID NO: 35. In certain embodiments, the N-terminal glutamate (E) residue of a heavy chain variable region of an antibody as described herein is replaced with a pyroglutamate (pE) residue.

In certain embodiments, the instant disclosure provides an isolated antibody that specifically binds to TIM-3 (e.g., human TIM-3), comprising a light chain variable region comprising an amino acid sequence of SEQ ID NO: 56. In certain embodiments, the instant disclosure provides an isolated antibody that specifically binds to TIM-3 (e.g., human TIM-3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 36, 37, 38, 39, 40, 41, 42, 43, 44, 45, 46, or 47. In certain embodiments, the antibody comprises a light chain variable region having the amino acid sequence set forth in SEQ ID NO: 36, 37, 38, 39, 40, 41, 42, 43, 44, 45, 46, or 47. In certain embodiments, the antibody comprises a light chain variable region having the amino acid sequence set forth in SEQ ID NO: 36. In certain embodiments, the antibody comprises a light chain variable region having the amino acid sequence set forth in SEQ ID NO: 37. In certain embodiments, the antibody comprises a light chain variable region having the amino acid sequence set forth in SEQ ID NO: 38. In certain embodiments, the antibody comprises a light chain variable region having the amino acid sequence set forth in SEQ ID NO: 39. In certain embodiments, the antibody comprises a light chain variable region having the amino acid sequence set forth in SEQ ID NO: 40. In certain embodiments, the antibody comprises a light chain variable region having the amino acid sequence set forth in SEQ ID NO: 41. In certain embodiments, the antibody comprises a light chain variable region having the amino acid sequence set forth in SEQ ID NO: 42. In certain embodiments, the antibody comprises a light chain variable region having the amino acid sequence set forth in SEQ ID NO: 43. In certain embodiments, the antibody comprises a light chain variable region having the amino acid sequence set forth in SEQ ID NO: 44. In certain embodiments, the antibody comprises a light chain variable region having the amino acid sequence set forth in SEQ ID NO: 45. In certain embodiments, the antibody comprises a light chain variable region having the amino acid sequence set forth in SEQ ID NO: 46. In certain embodiments, the antibody comprises a light chain variable region having the amino acid sequence set forth in SEQ ID NO: 47. In certain embodiments, the N-terminal glutamate (E) residue of a light chain variable region of an antibody as described herein is replaced with a pyroglutamate (pE) residue.

In certain embodiments, the instant disclosure provides an isolated antibody that specifically binds to TIM-3 (e.g., human TIM-3), comprising a heavy chain variable region comprising an amino acid sequence of SEQ ID NO: 55, and a light chain variable region comprising an amino acid sequence of SEQ ID NO: 56. In certain embodiments, the instant disclosure provides an isolated antibody that specifically binds to TIM-3 (e.g., human TIM-3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 24, 25, 26, 27, 28, 29, 30, 31, 32, 33, 34, or 35, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 36, 37, 38, 39, 40, 41, 42, 43, 44, 45, 46, or 47. In certain embodiments, the antibody comprises a heavy chain variable region having the amino acid sequence set forth in SEQ ID NO: 24, 25, 26, 27, 28, 29, 30, 31, 32, 33, 34, or 35, and a light chain variable region having the amino acid sequence set forth in SEQ ID NO: 36, 37, 38, 39, 40, 41, 42, 43, 44, 45, 46, or 47. In certain embodiments, the antibody comprises a heavy chain variable region and light chain variable region having the amino acid sequences set forth in SEQ ID NO: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46, respectively. In certain embodiments, the antibody comprises a heavy chain variable region and light chain variable region having the amino acid sequences set forth in SEQ ID NO: 24 and 36, respectively. In certain embodiments, the antibody comprises a heavy chain variable region and light chain variable region having the amino acid sequences set forth in SEQ ID NO: 24 and 38, respectively. In certain embodiments, the antibody comprises a heavy chain variable region and light chain variable region having the amino acid sequences set forth in SEQ ID NO: 26 and 42, respectively. In certain embodiments, the antibody comprises a heavy chain variable region and light chain variable region having the amino acid sequences set forth in SEQ ID NO: 24 and 42, respectively. In certain embodiments, the antibody comprises a heavy chain variable region and light chain variable region having the amino acid sequences set forth in SEQ ID NO: 24 and 46, respectively. In certain embodiments, the antibody comprises a heavy chain variable region and light chain variable region having the amino acid sequences set forth in SEQ ID NO: 24 and 43, respectively. In certain embodiments, the antibody comprises a heavy chain variable region and light chain variable region having the amino acid sequences set forth in SEQ ID NO: 26 and 43, respectively. In certain embodiments, the antibody comprises a heavy chain variable region and light chain variable region having the amino acid sequences set forth in SEQ ID NO: 26 and 46, respectively. In certain embodiments, the antibody comprises a heavy chain variable region and light chain variable region having the amino acid sequences set forth in SEQ ID NO: 26 and 41, respectively. In certain embodiments, the antibody comprises a heavy chain variable region and light chain variable region having the amino acid sequences set forth in SEQ ID NO: 24 and 41, respectively. In certain embodiments, the antibody comprises a heavy chain variable region and light chain variable region having the amino acid sequences set forth in SEQ ID NO: 25 and 39, respectively. In certain embodiments, the antibody comprises a heavy chain variable region and light chain variable region having the amino acid sequences set forth in SEQ ID NO: 24 and 47, respectively. In certain embodiments, the antibody comprises a heavy chain variable region and light chain variable region having the amino acid sequences set forth in SEQ ID NO: 25 and 40, respectively. In certain embodiments, the antibody comprises a heavy chain variable region and light chain variable region having the amino acid sequences set forth in SEQ ID NO: 26 and 47, respectively. In certain embodiments, the antibody comprises a heavy chain variable region and light chain variable region having the amino acid sequences set forth in SEQ ID NO: 25 and 37, respectively. In certain embodiments, the antibody comprises a heavy chain variable region and light chain variable region having the amino acid sequences set forth in SEQ ID NO: 25 and 45, respectively. In certain embodiments, the antibody comprises a heavy chain variable region and light chain variable region having the amino acid sequences set forth in SEQ ID NO: 25 and 44, respectively. In certain embodiments, the antibody comprises a heavy chain variable region and light chain variable region having the amino acid sequences set forth in SEQ ID NO: 25 and 46, respectively. In certain embodiments, the antibody comprises a heavy chain variable region and light chain variable region having the amino acid sequences set forth in SEQ ID NO: 25 and 42, respectively. In certain embodiments, the antibody comprises a heavy chain variable region and light chain variable region having the amino acid sequences set forth in SEQ ID NO: 25 and 41, respectively. In certain embodiments, the antibody comprises a heavy chain variable region and light chain variable region having the amino acid sequences set forth in SEQ ID NO: 25 and 43, respectively. In certain embodiments, the antibody comprises a heavy chain variable region and light chain variable region having the amino acid sequences set forth in SEQ ID NO: 25 and 47, respectively. In certain embodiments, the antibody comprises a heavy chain variable region and light chain variable region having the amino acid sequences set forth in SEQ ID NO: 27 and 46, respectively. In certain embodiments, the antibody comprises a heavy chain variable region and light chain variable region having the amino acid sequences set forth in SEQ ID NO: 28 and 46, respectively. In certain embodiments, the antibody comprises a heavy chain variable region and light chain variable region having the amino acid sequences set forth in SEQ ID NO: 29 and 46, respectively. In certain embodiments, the antibody comprises a heavy chain variable region and light chain variable region having the amino acid sequences set forth in SEQ ID NO: 30 and 46, respectively. In certain embodiments, the antibody comprises a heavy chain variable region and light chain variable region having the amino acid sequences set forth in SEQ ID NO: 31 and 46, respectively. In certain embodiments, the antibody comprises a heavy chain variable region and light chain variable region having the amino acid sequences set forth in SEQ ID NO: 32 and 46, respectively. In certain embodiments, the antibody comprises a heavy chain variable region and light chain variable region having the amino acid sequences set forth in SEQ ID NO: 33 and 46, respectively. In certain embodiments, the antibody comprises a heavy chain variable region and light chain variable region having the amino acid sequences set forth in SEQ ID NO: 34 and 46, respectively. In certain embodiments, the antibody comprises a heavy chain variable region and light chain variable region having the amino acid sequences set forth in SEQ ID NO: 35 and 46, respectively. In certain embodiments, the N-terminal glutamate (E) residue of a heavy chain variable region of an antibody as described herein is replaced with a pyroglutamate (pE) residue and/or the N-terminal glutamate (E) residue of a light chain variable region of the antibody is replaced with a pyroglutamate (pE) residue.

In certain embodiments, the instant disclosure provides an isolated antibody that specifically binds to TIM-3 (e.g., human TIM-3), comprising a heavy chain variable region having an amino acid sequence derived from a human IGHV3-23 germline sequence (e.g., IGHV3-23*04, e.g., having the amino acid sequence of SEQ ID NO: 84). One or more regions selected from framework 1, framework 2, framework 3, CDRH1, and CDRH2 (e.g., two, three, four or five of these regions) can be derived from a human IGHV3-23 germline sequence (e.g., IGHV3-23*04, e.g., having the amino acid sequence of SEQ ID NO: 84). In one embodiment, framework 1, framework 2, framework 3, CDRH1, and CDRH2 are all derived from a human IGHV3-23 germline sequence (e.g., IGHV3-23*04, e.g., having the amino acid sequence of SEQ ID NO: 84).

In certain embodiments, the instant disclosure provides an isolated antibody that specifically binds to TIM-3 (e.g., human TIM-3), comprising a light chain variable region having an amino acid sequence derived from a human germline sequence selected from the group consisting of IGKV1-27 (e.g., IGKV1-27*01, e.g., having the amino acid sequence of SEQ ID NO: 85), IGKV3-11 (e.g., IGKV3-11*01, e.g., having the amino acid sequence of SEQ ID NO: 86), IGKV3-20 (e.g., IGKV3-20*01, e.g., having the amino acid sequence of SEQ ID NO: 87), and IGKV3D-20 (e.g., IGKV3D-20*01, e.g., having the amino acid sequence of SEQ ID NO: 88). One or more regions selected from framework 1, framework 2, framework 3, CDRL1, and CDRL2 (e.g., two, three, four or five of these regions) can be derived from a human germline sequence selected from the group consisting of IGKV1-27 (e.g., IGKV1-27*01, e.g., having the amino acid sequence of SEQ ID NO: 85), IGKV3-11 (e.g., IGKV3-11*01, e.g., having the amino acid sequence of SEQ ID NO: 86), IGKV3-20 (e.g., IGKV3-20*01, e.g., having the amino acid sequence of SEQ ID NO: 87), and IGKV3D-20 (e.g., IGKV3D-20*01, e.g., having the amino acid sequence of SEQ ID NO: 88). In one embodiment, framework 1, framework 2, framework 3, CDRL1, and CDRL2 are all derived from a human germline sequence selected from the group consisting of IGKV1-27 (e.g., IGKV1-27*01, e.g., having the amino acid sequence of SEQ ID NO: 85), IGKV3-11 (e.g., IGKV3-11*01, e.g., having the amino acid sequence of SEQ ID NO: 86), IGKV3-20 (e.g., IGKV3-20*01, e.g., having the amino acid sequence of SEQ ID NO: 87), and IGKV3D-20 (e.g., IGKV3D-20*01, e.g., having the amino acid sequence of SEQ ID NO: 88).

In certain embodiments, the instant disclosure provides an isolated antibody that specifically binds to TIM-3 (e.g., human TIM-3), comprising a heavy chain variable region having an amino acid sequence derived from a human IGHV3-23 germline sequence (e.g., IGHV3-23*04, e.g., having the amino acid sequence of SEQ ID NO: 84), and a light chain variable region having an amino acid sequence derived from a human germline sequence selected from the group consisting of IGKV1-27 (e.g., IGKV1-27*01, e.g., having the amino acid sequence of SEQ ID NO: 85), IGKV3-11 (e.g., IGKV3-11*01, e.g., having the amino acid sequence of SEQ ID NO: 86), IGKV3-20 (e.g., IGKV3-20*01, e.g., having the amino acid sequence of SEQ ID NO: 87), and IGKV3D-20 (e.g., IGKV3D-20*01, e.g., having the amino acid sequence of SEQ ID NO: 88).

In certain embodiments, the instant disclosure provides an isolated antibody that cross-competes for binding to TIM-3 (e.g., human TIM-3) with an antibody comprising the heavy and light chain variable region amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46, respectively.

In certain embodiments, the instant disclosure provides an isolated antibody that binds to the same or an overlapping epitope of TIM-3 (e.g., an epitope of human TIM-3) as an antibody described herein, e.g., an antibody comprising the heavy and light chain variable region amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46, respectively. In certain embodiments, the epitope of an antibody can be determined by, e.g., NMR spectroscopy, surface plasmon resonance (BIAcore™), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274;

McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of TIM-3 (e.g., human TIM-3) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as TIM-3 (e.g., human TIM-3). Numerous types of competitive binding assays are known, for example: solid phase direct or indirect radioimmunoassay (MA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using 1-125 label (see Morel G A et al., (1988) Mol Immunol 25(1): 7-15); solid phase direct biotin-avidin EIA (see Cheung R C et al., (1990) Virology 176: 546-52); and direct labeled MA (see Moldenhauer G et al., (1990) Scand J Immunol 32: 77-82), all of which are herein incorporated by reference in their entireties. Typically, such an assay involves the use of purified antigen (e.g., TIM-3 such as human TIM-3) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the instant disclosure provides an isolated antibody that specifically binds to TIM-3 (e.g., human TIM-3), the antibody comprising a heavy chain comprising the amino acid sequence set forth in SEQ ID NO: 57, 58, 59, 60, 61, 62, 63, 64, 65, 66, 67, or 68. In certain embodiments, the antibody comprises a heavy chain comprising the amino acid sequence set forth in SEQ ID NO: 57. In certain embodiments, the antibody comprises a heavy chain comprising the amino acid sequence set forth in SEQ ID NO: 58. In certain embodiments, the antibody comprises a heavy chain comprising the amino acid sequence set forth in SEQ ID NO: 59. In certain embodiments, the antibody comprises a heavy chain comprising the amino acid sequence set forth in SEQ ID NO: 60. In certain embodiments, the antibody comprises a heavy chain comprising the amino acid sequence set forth in SEQ ID NO: 61. In certain embodiments, the antibody comprises a heavy chain comprising the amino acid sequence set forth in SEQ ID NO: 62. In certain embodiments, the antibody comprises a heavy chain comprising the amino acid sequence set forth in SEQ ID NO: 63. In certain embodiments, the antibody comprises a heavy chain comprising the amino acid sequence set forth in SEQ ID NO: 64. In certain embodiments, the antibody comprises a heavy chain comprising the amino acid sequence set forth in SEQ ID NO: 65. In certain embodiments, the antibody comprises a heavy chain comprising the amino acid sequence set forth in SEQ ID NO: 66. In certain embodiments, the antibody comprises a heavy chain comprising the amino acid sequence set forth in SEQ ID NO: 67. In certain embodiments, the antibody comprises a heavy chain comprising the amino acid sequence set forth in SEQ ID NO: 68. In certain embodiments, the N-terminal glutamate (E) residue of a heavy chain of an antibody as described herein is replaced with a pyroglutamate (pE) residue.

In certain embodiments, the instant disclosure provides an isolated antibody that specifically binds to TIM-3 (e.g., human TIM-3), the antibody comprising a light chain comprising the amino acid sequence set forth in SEQ ID NO: 69. In certain embodiments, the N-terminal glutamate (E) residue of a light chain of an antibody as described herein is replaced with a pyroglutamate (pE) residue.

In certain embodiments, the instant disclosure provides an isolated antibody that specifically binds to TIM-3 (e.g., human TIM-3), the antibody comprising a heavy chain comprising the amino acid sequence of SEQ ID NO: 57; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 58; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 59; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 60; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 61; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 62; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 63; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 64; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 65; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 66; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 67; and a light chain comprising the amino acid sequence of SEQ ID NO: 69. In certain embodiments, the instant disclosure provides an isolated antibody that specifically binds to TIM-3 (e.g., human TIM-3), the antibody comprising a heavy chain comprising the amino acid sequence of SEQ ID NO: 68; and a light chain comprising the amino acid sequence of SEQ ID NO: 69. In certain embodiments, the N-terminal glutamate (E) residue of a heavy chain of an antibody as described herein is replaced with a pyroglutamate (pE) residue and/or the N-terminal glutamate (E) residue of a light chain of the antibody is replaced with a pyroglutamate (pE) residue.

Any Ig constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In certain embodiments, the instant disclosure provides an isolated antibody that specifically binds to TIM-3 (e.g., human TIM-3), the antibody comprising a heavy chain constant region comprising the amino acid sequence of SEQ ID NO: 70, 71, 72, 73, 74 or 75. In certain embodiments, the instant disclosure provides an isolated antibody that specifically binds to TIM-3 (e.g., human TIM-3), the antibody comprising a light chain constant region comprising the amino acid sequence of SEQ ID NO: 76 or 77.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In some embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In some embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU numbering system. In certain embodiments, a mutation selected from the group consisting of D265A, P329A, and a combination thereof, numbered according to the EU numbering system, may be made in the constant region of an antibody described herein.

In a specific embodiment, an antibody described herein comprises the constant domain of an IgG$_1$ with an N297Q or N297A amino acid substitution, numbered according to the EU numbering system. In one embodiment, an antibody described herein comprises the constant domain of an IgG$_1$ with a mutation selected from the group consisting of D265A, P329A, and a combination thereof, numbered according to the EU numbering system. In another embodiment, an antibody described herein comprises the constant domain of an IgG$_1$ with a mutation selected from the group consisting of L234A, L235A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In some embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to TIM-3 (e.g., human TIM-3), the antibody comprising a heavy chain constant region comprising the amino acid sequence of SEQ ID NO: 74. In certain embodiments, the instant disclosure provides an isolated antibody that specifically binds to TIM-3 (e.g., human TIM-3), the antibody comprising a heavy chain constant region comprising the amino acid sequence of SEQ ID NO: 75.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to TIM-3 (e.g., human TIM-3) and functions as an antagonist.

In certain embodiments, the instant disclosure provides an isolated antibody that specifically binds to TIM-3 (e.g., human TIM-3) and decreases TIM-3 (e.g., human TIM-3) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to TIM-3 (e.g., human TIM-3) activity without any antibody or with an unrelated antibody (e.g., an antibody that does not specifically bind to TIM-3 (e.g., human TIM-3)). In certain embodiments, the instant disclosure provides an isolated antibody that specifically binds to TIM-3 (e.g., human TIM-3) and decreases TIM-3 (e.g., human TIM-3) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to TIM-3 (e.g., human TIM-3) activity without any antibody or with an unrelated antibody (e.g., an antibody that does not specifically bind to TIM-3 (e.g., human TIM-3)). Non-limiting examples of TIM-3 (e.g., human TIM-3) activity can include TIM-3 (e.g., human TIM-3) signaling, TIM-3 (e.g., human TIM-3) binding to TIM-3 (e.g., human TIM-3) ligand (e.g., phosphatidylserine), and inhibition of cytokine production (e.g., IFN-γ and/or TNF-α). In certain embodiments, the instant disclosure provides an isolated antibody that specifically binds to TIM-3 (e.g., human TIM-3) and deactivates, reduces, or inhibits a TIM-3 (e.g., human TIM-3) activity. In specific embodiments, a decrease in a TIM-3 (e.g., human TIM-3) activity is assessed as described in the Examples, infra.

In specific embodiments, the instant disclosure provides an isolated antibody that specifically binds to TIM-3 (e.g., human TIM-3) and reduces TIM-3 (e.g., human TIM-3) binding to its ligand (e.g., phosphatidylserine) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to TIM-3 (e.g., human TIM-3) binding to its ligand (e.g., phosphatidylserine) without any antibody or with an unrelated antibody (e.g., an antibody that does not specifically bind to TIM-3 (e.g., human TIM-3)). In specific embodiments, the instant disclosure provides an isolated antibody that specifically binds to TIM-3 (e.g., human TIM-3) and reduces TIM-3 (e.g., human TIM-3) binding to its ligand (e.g., phosphatidylserine) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to TIM-3 (e.g., human TIM-3) binding to its ligand (e.g., phosphatidylserine) without any antibody or with an unrelated antibody (e.g., an antibody that does not specifically bind to TIM-3 (e.g., human TIM-3)).

In specific embodiments, the instant disclosure provides an isolated antibody that specifically binds to TIM-3 (e.g., human TIM-3) and increases cytokine production (e.g., IFN-γ and/or TNF-α) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to TIM-3 (e.g., human TIM-3)). In specific embodiments, the instant disclosure provides an isolated antibody that specifically binds to TIM-3 (e.g., human TIM-3) and increases cytokine production (e.g., IFN-γ and/or TNF-α) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to TIM-3 (e.g., human TIM-3)).

In specific embodiments, the instant disclosure provides an isolated antibody that specifically binds to TIM-3 (e.g., human TIM-3) and either alone or in combination with an anti-PD-1 antibody (e.g., pembrolizumab or nivolumab) increases IFN-γ production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFN-γ production without any antibody or with an unrelated antibody (e.g., an antibody that does not specifically bind to TIM-3 (e.g., human TIM-3)).

In certain embodiments, human peripheral blood mononuclear cells (PBMCs) stimulated with *Staphylococcus* Enterotoxin A (SEA) in the presence of an antibody described herein, which specifically binds to TIM-3 (e.g., human TIM-3), have increased IFN-γ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to TIM-3 (e.g., human TIM-3)), as assessed by methods described herein (see the Examples, infra) or known to one of skill in the art.

In specific embodiments, the instant disclosure provides an isolated antibody that specifically binds to TIM-3 (e.g., human TIM-3) and either alone or in combination with an anti-PD-1 antibody (e.g., pembrolizumab or nivolumab) increases IFN-γ and/or TNFα production in tumor infiltrating lymphocytes (TILs) in response to anti-CD3 antibody and anti-CD28 antibody stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFN-γ and/or TNFα production without an antibody that specifically binds to TIM-3 (e.g., human TIM-3). In one embodiment, the TILs are from non-small cell lung cancer (NSCLC) tumor. In another embodiment, the TILs are from gallbladder adenocarcinoma tumor. In another embodiment, the TILs are from breast cancer tumor.

In certain embodiments, tumor infiltrating lymphocytes (TILs) stimulated with anti-CD3 and anti-CD28 antibodies in the presence of an antibody described herein, which specifically binds to TIM-3 (e.g., human TIM-3), have increased IFN-γ and/or TNFα production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to TILs only stimulated with anti-CD3 and anti-CD28 antibodies without an antibody that specifically binds to TIM-3 (e.g., human TIM-3), as assessed by methods described herein (see the Examples, infra) or known to one of skill in the art. In one embodiment, the TILs are from non-small cell lung cancer (NSCLC) tumor. In another embodiment, the TILs are from gallbladder adenocarcinoma tumor. In another embodiment, the TILs are from breast cancer tumor.

In certain embodiments, the instant disclosure provides an isolated antibody that specifically binds to TIM-3 (e.g., human TIM-3) and is internalized upon binding to cells expressing TIM-3 (e.g., human TIM-3). In specific embodiments, at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody described herein is internalized upon binding to cells expressing TIM-3 (e.g., human TIM-3), as assessed by methods described herein (see the Examples, infra) or known to one of skill in the art. In certain embodiments, a lower percentage of the cells expressing TIM-3 (e.g., human TIM-3) survive in the presence of the antibody described herein than in the presence of a reference anti-TIM-3 (e.g., human TIM-3) antibody in an assay comprising the following steps:

(a) plating the cells expressing TIM-3 (e.g., human TIM-3) at $2 \times 10^4$ cells per well in a tissue culture plate;
(b) adding the same concentrations of αHFc-NC-DM1 and the antibody described herein or the reference anti-TIM-3 (e.g., human TIM-3) antibody (e.g., 1.5 ng/ml, 4.6 ng/ml, 13.7 ng/ml, 41.2 ng/ml, 123.5 ng/ml, 370 ng/ml, 1111 ng/ml, or 3333 ng/ml) at a final volume of 100 µl/well;
(c) incubating at 37° C. and 5% $CO_2$ for 72 hours;
(d) measuring survival of the cells expressing TIM-3 (e.g., human TIM-3); and
(e) calculating percentage of cell survival relative to untreated cells expressing TIM-3 (e.g., human TIM-3).

In certain embodiments, the percentage of cell survival in the presence of the antibody described herein is at least about 5%, 10%, 15%, 20%, 25%, 30%, 35%, 40%, 45%, 50%, 55%, 60%, 65%, 70%, 75%, 80%, 85%, 90%, 95%, 98%, or 99% lower than the percentage of cell survival in the presence of the reference anti-TIM-3 (e.g., human TIM-3) antibody In certain embodiments, the percentage of cell survival in the presence of the antibody described herein is at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than the percentage of cell survival in the presence of the reference anti-TIM-3 (e.g., human TIM-3) antibody. In certain embodiments, the reference anti-TIM-3 (e.g., human TIM-3) antibody is pab1944w (IgG$_1$ N297A). In certain embodiments, the reference anti-TIM-3 (e.g., human TIM-3) antibody is Hum11 (IgG$_4$ S228P). In certain embodiments, the cells expressing TIM-3 (e.g., human TIM-3) are Kasumi-3 cells. In certain embodiments, the cells expressing TIM-3 (e.g., human TIM-3) are Kasumi-3 cells (ATCC® CRL-2725™). In certain embodiments, the cells expressing TIM-3 (e.g., human TIM-3) are Jurkat cells engineered to express TIM-3 (e.g., human TIM-3).

In certain embodiments, at most 50% of the cells expressing TIM-3 (e.g., human TIM-3) survive in the presence of the antibody described herein relative to untreated cells expressing TIM-3 (e.g., human TIM-3) in an assay comprising the following steps:
(a) plating the cells expressing TIM-3 (e.g., human TIM-3) at $2 \times 10^4$ cells per well in a tissue culture plate;
(b) adding the same concentrations of αHFc-NC-DM1 and the antibody described herein (e.g., 1.5 ng/ml, 4.6 ng/ml, 13.7 ng/ml, 41.2 ng/ml, 123.5 ng/ml, 370 ng/ml, 1111 ng/ml, or 3333 ng/ml) at a final volume of 100µl/well;
(c) incubating at 37° C. and 5% $CO_2$ for 72 hours;
(d) measuring survival of the cells expressing TIM-3 (e.g., human TIM-3); and
(e) calculating percentage of cell survival relative to untreated cells expressing TIM-3 (e.g., human TIM-3).

In certain embodiments, at most 10%, 15%, 20%, 25%, 30%, 35%, 40%, 45%, or 50% of the cells expressing TIM-3 (e.g., human TIM-3) survive in the presence of the antibody described herein relative to untreated cells expressing TIM-3 (e.g., human TIM-3). In certain embodiments, αHFc-NC-DM1 and the antibody described herein are added at a concentration of 1111 ng/ml and at most 10%, 15%, 20%, 25%, 30%, 35%, 40%, 45%, or 50% of the cells expressing TIM-3 (e.g., human TIM-3) survive in the presence of the antibody described herein relative to untreated cells expressing TIM-3 (e.g., human TIM-3). In certain embodiments, αHFc-NC-DM1 and the antibody described herein are added at a concentration of 1111 ng/ml and at most 50% of the cells expressing TIM-3 (e.g., human TIM-3) survive in the presence of the antibody described herein relative to untreated cells expressing TIM-3 (e.g., human TIM-3).

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH1 comprising the amino acid sequence of $X_1X_2X_3X_4X_5S$ (SEQ ID NO: 48), wherein $X_1$ is R, S, A, G, K, M, or T,
$X_2$ is Q, S, A, G, R, or T,
$X_3$ is N, Y, G, or Q,
$X_4$ is A or Q, and
$X_5$ is W, M, A, S, or T.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH1 comprising the amino acid sequence of $X_1X_2NAWS$ (SEQ ID NO: 49), wherein $X_1$ is R or A; and
$X_2$ is Q or R.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH1 comprising the amino acid sequence of $X_1X_2GQX_3S$ (SEQ ID NO: 50), wherein $X_1$ is K, M, or G;
$X_2$ is A or S; and
$X_3$ is S or T.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH1 comprising the amino acid sequence of $X_1X_2QQAS$ (SEQ ID NO: 51), wherein $X_1$ is S, R, T, or G; and $X_2$ is A, S, T, or G.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH2 comprising the amino acid sequence of WVSAISGSGGSTY (SEQ ID NO: 2).

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRH3 comprising the amino acid sequence of AKGGDYGGNYFD (SEQ ID NO: 3).

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRL1 comprising the amino acid sequence of $X_1ASQSVX_2SSYLA$ (SEQ ID NO: 52), wherein $X_1$ is R or G, and $X_2$ is absent or S.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRL2 comprising the amino acid sequence of $X_1ASX_2RAT$ (SEQ ID NO: 53), wherein $X_1$ is D or G, and $X_2$ is N, S, or T.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a CDRL3 comprising the amino acid sequence of $QQYGSSPX_1T$ (SEQ ID NO: 54), wherein $X_1$ is L or I.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody cross-competes for binding to TIM-3 (e.g., human TIM-3) with an antibody comprising the heavy and light chain variable region amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46, respectively.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody binds to the same or an overlapping epitope of TIM-3 (e.g., an epitope of human TIM-3) as an antibody described herein, e.g., an antibody comprising the heavy and light chain variable region amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 28 and 46; 29 and 46; 30 and 46; 31 and 46; 32 and 46; 33 and 46; 34 and 46; or 35 and 46, respectively.

In certain embodiments, the instant disclosure provides an isolated antibody that specifically binds to TIM-3 (e.g., human TIM-3), wherein at least about 5%, 10%, 15%, 20%, 25%, 30%, 35%, 40%, 45%, 50%, 55%, 60%, 65%, 70%, 75%, 80%, 85%, 90%, 95%, 98%, or 99% of the antibody is internalized upon binding to cells expressing TIM-3 (e.g., human TIM-3), as assessed by methods described herein (see the Examples, infra) or known to one of skill in the art, and wherein the antibody comprises a human IgG heavy chain constant region that is a variant of a wild type human IgG heavy chain constant region, wherein the variant human IgG heavy chain constant region binds to a human Fc gamma receptor with lower affinity than the wild type human IgG heavy chain constant region binds to the human Fc gamma receptor. In certain embodiments, the human Fc gamma receptor is selected from the group consisting of FcγRI, FcγRII, and FcγRIII. In certain embodiments, the variant human IgG heavy chain constant region is an $IgG_1$ constant region comprising a N297A mutation, numbered according to the EU numbering system.

5.3 Pharmaceutical Compositions

Provided herein are compositions comprising an anti-TIM-3 (e.g., human TIM-3) antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-TIM-3 (e.g., human TIM-3) antibody described herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting TIM-3 (e.g., human TIM-3) activity and treating a condition, such as cancer or an infectious disease. In one embodiment, the present invention relates to a pharmaceutical composition of the present invention comprising an anti-TIM-3 antibody of the present invention for use as a medicament. In another embodiment, the present invention relates to a pharmaceutical composition of the present invention for use in a method for the treatment of cancer or an infectious disease. In another embodiment, the present invention relates to use of a pharmaceutical composition of the invention for preparing a medicament for treating cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-TIM-3 (e.g., human TIM-3) antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microtine powder for insufflations, alone or in combination with an inert carrier such as lactose. In such a case, the particles of the formulation will, in one embodiment, have diameters of less than 50 microns, in one embodiment less than 10 microns.

An anti-TIM-3 (e.g., human TIM-3) antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-TIM-3 (e.g., human TIM-3) antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.4 Methods of Use and Uses

In another aspect, the instant disclosure provides a method of treating a subject using the anti-TIM-3 (e.g., human TIM-3) antibodies disclosed herein. Any disease or disorder in a subject that would benefit from inhibition of TIM-3 (e.g., human TIM-3) function can be treated using the anti-TIM-3 (e.g., human TIM-3) antibodies disclosed herein. The anti-TIM-3 (e.g., human TIM-3) antibodies disclosed herein are particularly useful for inhibiting immune system tolerance to tumors, and accordingly can be used as an immunotherapy for subjects with cancer. For example, in certain embodiments, the instant disclosure provides a method of increasing T cell activation in response to an antigen in a subject, the method comprising administering to the subject an effective amount of an anti-TIM-3 (e.g., human TIM-3) antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein. In certain embodiments, the instant disclosure provides an antibody or pharmaceutical composition as disclosed herein for use in a method for the treatment of cancer or an infectious disease. In certain embodiments, the instant disclosure provides an antibody or pharmaceutical composition as disclosed herein for use as a medicament. In another embodiment, the instant disclosure provides use of an antibody or pharmaceutical composition as disclosed herein for preparing a medicament for treating cancer or an infectious disease.

Cancers that can be treated with the anti-TIM-3 (e.g., human TIM-3) antibodies or pharmaceutical compositions disclosed herein include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is associated with elevated PD-1 activity (e.g., elevated PD-1 expression).

In one embodiment, the cancer is chosen from a lung cancer (e.g., lung adenocarcinoma or a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer (e.g., hepatocellular carcinoma), a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In one embodiment, the cancer is NSCLC. In one embodiment, the cancer is a renal cell carcinoma. In one embodiment, the cancer is an ovarian cancer. In a specific embodiment, the ovarian cancer is a platinum-refractory ovarian cancer.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CIVIL), chronic myeloid leukemia (CIVIL), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In one embodiment the cancer is a myeloma, for example, multiple myeloma.

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-TIM-3 (e.g., human TIM-3) antibody or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-TIM-3 (e.g., human TIM-3) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-TIM-3 (e.g., human TIM-3) antibody described herein or a composition thereof is the only active agent administered to a subject. In some embodiments, an anti-TIM-3 (e.g., human TIM-3) antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-TIM-3 (e.g., human TIM-3) antibodies or pharmaceutical compositions disclosed herein are caused by infectious agents including but not limited to bacteria, parasites, fungi, protozae, and viruses. In a specific embodiment, the infectious disease treated and/or prevented by anti-TIM-3 (e.g., human TIM-3) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, Mycobacteria *rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertussis, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania*, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergil-*

*lus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-CD137 antibody, an antagonist anti-TIGIT antibody, an antagonist anti-VISTA antibody, an agonist anti-GITR antibody, and an agonist anti-OX40 antibody.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-TIM-3 (e.g., human TIM-3) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in one embodiment, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-TIM-3 (e.g., human TIM-3) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an anti-TIM-3 (e.g., human TIM-3) antibody disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In certain embodiments, an anti-TIM-3 (e.g., human TIM-3) antibody disclosed herein is administered to a subject in combination with a vaccine as described in WO 2016/183486 (e.g., a vaccine comprising at least one synthetic peptide comprising a cancer-specific mutation present in a cancer from the subject), incorporated herein by reference in its entirety. In a specific embodiment, an anti-TIM-3 (e.g., human TIM-3) antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-of-parts comprising (a) an antibody and/or pharmaceutical composition of the present invention and (b) a vaccine. In one embodiment, the vaccine is a heat shock protein based tumor vaccine. In one embodiment, the vaccine is a heat shock protein based pathogen vaccine.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. PODMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-TIM-3 (e.g., human TIM-3) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436, 404, 6,447,780, 6,447,781 and 6,610,659.

In certain embodiments, an anti-TIM-3 antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), MONTANIDE' ISA (incomplete Seppic adjuvant), the RIBIadjuvant System® (RAS®), TiterMax®, muramyl peptides, Syntex Adjuvant Formulation (SAF)®, alum (aluminum hydroxide and/or aluminum phosphate), aluminum salt adjuvants, Gerbu Adjuvants® (GERBU Biochemicals GmbH), nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, stimulator of interferon genes (STING) agonists, immuno-stimulating complexes such as saponins, Quil A, QS-21, QS-7, ISCOMATRIX®, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON®.

In certain embodiments, an anti-TIM-3 antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-TIM-3 antibody disclosed herein is administered to a subject in combination with a cell expressing a chimeric antigen receptor (CAR). In certain embodiments, the cell is a T cell.

In certain embodiments, an anti-TIM-3 antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

The anti-TIM-3 (e.g., human TIM-3) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-TIM-3 (e.g., human TIM-3) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intrathecal, intratumoral, conjunctival, intra-arterial, and subcutaneous routes. In certain embodiments, the antibody or pharmaceutical composition is delivered intravenously. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

An anti-TIM-3 (e.g., human TIM-3) antibody described herein can also be used to assay TIM-3 (e.g., human TIM-3) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-TIM-3 (e.g., human TIM-3) antibody described herein can be labeled and used in combination with an anti-TIM-3 (e.g., human TIM-3) antibody to detect TIM-3 (e.g., human TIM-3) protein levels. Therefore, in one embodiment, the present invention relates to the use of an antibody of the present invention for in vitro detection of TIM-3 (e.g., human TIM-3) protein in a biological sample. In a further embodiment, the present invention relates to the use of an anti-TIM-3 antibody of the invention, for assaying and/or detecting TIM-3 (e.g., human TIM-3) protein levels in a biological sample in vitro, optionally wherein the anti-TIM-3 antibody is conjugated to a radionuclide or detectable label, and/or carries a label described herein, and/or wherein an immunohistological method is used.

Assaying for the expression level of TIM-3 (e.g., human TIM-3) protein is intended to include qualitatively or quantitatively measuring or estimating the level of TIM-3 (e.g., human TIM-3) protein in a first biological sample either directly (e.g., by determining or estimating absolute protein level) or relatively (e.g., by comparing to the disease associated protein level in a second biological sample). TIM-3 (e.g., human TIM-3) polypeptide expression level in the first biological sample can be measured or estimated and compared to a standard TIM-3 (e.g., human TIM-3) protein level, the standard being taken from a second biological sample obtained from an individual not having the disorder or being determined by averaging levels from a population of individuals not having the disorder. As will be appreciated in the art, once the "standard" TIM-3 (e.g., human TIM-3) polypeptide level is known, it can be used repeatedly as a standard for comparison. Therefore, in a further embodiment, the present invention relates to an in vitro method for assaying and/or detecting TIM-3 protein levels, for example human TIM-3 protein levels, in a biological sample, comprising qualitatively or quantitatively measuring or estimating the level of TIM-3 protein, for example of human TIM-3 protein, in a biological sample, by an immunohistological method.

As used herein, the term "biological sample" refers to any biological sample obtained from a subject, cell line, tissue, or other source of cells potentially expressing TIM-3 (e.g., human TIM-3). Methods for obtaining tissue biopsies and body fluids from animals (e.g., humans) are well known in the art. Biological samples include peripheral mononuclear blood cells.

An anti-TIM-3 (e.g., human TIM-3) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-TIM-3 antibody and/or pharmaceutical composition of the present invention for use as a diagnostic. In one embodiment, the present invention relates to an anti-TIM-3 antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-TIM-3 antibody of the invention, for predicting, diagnosing and/or monitoring of a subject having or suspected to have an immune system-dysfunction and/or with regard to an anticipated or desired immune system response, antigen response or vaccine response by assaying and/or detecting human TIM-3 protein levels in a biological sample of the subject in vitro.

In one embodiment, an anti-TIM-3 (e.g., human TIM-3) antibody can be used in immunohistochemistry of biopsy samples. In one embodiment, the method is an in vitro method. In another embodiment, an anti-TIM-3 (e.g., human TIM-3) antibody can be used to detect levels of TIM-3 (e.g., human TIM-3), or levels of cells which contain TIM-3 (e.g., human TIM-3) on their membrane surface, which levels can then be linked to certain disease symptoms. Anti-TIM-3 (e.g., human TIM-3) antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-TIM-3 (e.g., human TIM-3) antibodies described herein may carry or may be conjugated to a fluorescence label. Exemplary fluorescence labels include, for example, reactive and conjugated probes, e.g., Aminocoumarin, Fluorescein and Texas red, Alexa Fluor® dyes, Cyanine dyes and DyLight® Fluorescent dyes. An anti-TIM-3 (e.g., human TIM-3) antibody may carry or may be conjugated to a radioactive label or radionuclide, such as the isotopes $^3$H, $^{14}$C, $^{32}$P, $^{35}$S, $^{36}$Cl, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-TIM-3 (e.g., human TIM-3) antibody to TIM-3 (e.g., human TIM-3). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-TIM-3 (e.g., human TIM-3) antibody under conditions that allow for the formation of a complex between the antibody and TIM-3 (e.g., human TIM-3). Any complexes formed between the antibody and TIM-3 (e.g., human TIM-3) are detected and compared in the sample and the control. In light of the specific binding of the antibodies described herein for TIM-3 (e.g., human TIM-3), the antibodies can be used to specifically detect TIM-3 (e.g., human TIM-3) expression on the surface of cells. The antibodies described herein can also be used to purify TIM-3 (e.g., human TIM-3) via immunoaffinity purification. Also included herein is an assay system which may be prepared in the form of a test kit, kit or kit-of-parts for the quantitative analysis of the extent of the presence of, for instance, TIM-3 (e.g., human TIM-3) or TIM-3 (e.g., human TIM-3)/TIM-3

(e.g., human TIM-3) ligand complexes. The system, test kit, kit or kit-of-parts may comprise a labeled component, e.g., a labeled antibody, and one or more additional immunochemical reagents.

5.5 Polynucleotides, Vectors and Methods of Producing Anti-TIM-3 Antibodies

In another aspect, provided herein are polynucleotides comprising a nucleotide sequence encoding an antibody described herein or a fragment thereof (e.g., a light chain variable region and/or heavy chain variable region) that specifically binds to a TIM-3 (e.g., human TIM-3) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a TIM-3 (e.g., human TIM-3) polypeptide and comprises an amino acid sequence as described herein, as well as antibodies which compete with such antibodies for binding to a TIM-3 (e.g., human TIM-3) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1).

Also provided herein are polynucleotides encoding an anti-TIM-3 (e.g., human TIM-3) antibody that are optimized, e.g., by codon/RNA optimization, replacement with heterologous signal sequences, and elimination of mRNA instability elements. Methods to generate optimized nucleic acids encoding an anti-TIM-3 (e.g., human TIM-3) antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-TIM-3 (e.g., human TIM-3) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-TIM-3 (e.g., human TIM-3) antibody encoded by polynucleotides that have not been optimized.

In certain embodiments, an optimized polynucleotide sequence encoding an anti-TIM-3 (e.g., human TIM-3) antibody described herein or a fragment thereof (e.g., VL domain and/or VH domain) can hybridize to an antisense (e.g., complementary) polynucleotide of an unoptimized polynucleotide sequence encoding an anti-TIM-3 (e.g., human TIM-3) antibody described herein or a fragment thereof (e.g., VL domain and/or VH domain). In specific embodiments, an optimized nucleotide sequence encoding an anti-TIM-3 (e.g., human TIM-3) antibody described herein or a fragment hybridizes under high stringency conditions to antisense polynucleotide of an unoptimized polynucleotide sequence encoding an anti-TIM-3 (e.g., human TIM-3) antibody described herein or a fragment thereof. In a specific embodiment, an optimized nucleotide sequence encoding an anti-TIM-3 (e.g., human TIM-3) antibody described herein or a fragment thereof hybridizes under high stringency, intermediate or lower stringency hybridization conditions to an antisense polynucleotide of an unoptimized nucleotide sequence encoding an anti-TIM-3 (e.g., human TIM-3) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest.

Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-TIM-3 (e.g., human TIM-3) antibodies described herein can be readily isolated and sequenced using conventional procedures (e.g., by using oligonucleotide probes that are capable of binding specifically to genes encoding the heavy and light chains of the anti-TIM-3 (e.g., human TIM-3) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-TIM-3 (e.g., human TIM-3) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to TIM-3 (e.g., human TIM-3) and related polynucleotides and expression vectors. Provided herein are vectors (e.g., expression vectors) comprising polynucleotides comprising nucleotide sequences encoding anti-TIM-3 (e.g., human TIM-3) antibodies or a fragment for recombinant expression in host cells, preferably in mammalian cells. Also provided herein are host cells comprising such vectors for recombinantly expressing anti-TIM-3 (e.g., human TIM-3) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to TIM-3 (e.g., human TIM-3) involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036;

and U.S. Pat. No. 5,122,464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-TIM-3 (e.g., human TIM-3) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-TIM-3 (e.g., human TIM-3) antibody described herein, and a second vector comprising a polynucleotide encoding a heavy chain/heavy chain variable region of an anti-TIM-3 (e.g., human TIM-3) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to TIM-3 (e.g., human TIM-3) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-TIM-3 (e.g., human TIM-3) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The GS System™ with Potelligent® Technology (Lonza) is an example of such a system that can be used to produce antibodies with reduced fucose content.

For long-term, high-yield production of recombinant proteins, stable expression cells can be generated. For example, cell lines which stably express an anti-TIM-3 (e.g., human TIM-3) antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-TIM-3 (e.g., human TIM-3) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to TIM-3 (e.g., human TIM-3) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to TIM-3 (e.g., human TIM-3) comprising culturing a cell or host cell described herein. In one embodiment, the method is performed in vitro. In a certain aspect, provided herein is a method of making an antibody which specifically binds to TIM-3 (e.g., human TIM-3) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to TIM-3 (e.g., human TIM-3) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., TIM-3 (e.g., human TIM-3)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In some embodiments, mice (or other animals, such as rats, monkeys, donkeys, pigs, sheep, hamster, or dogs) can be immunized with an antigen (e.g., TIM-3 (e.g., human TIM-3)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against TIM-3 (e.g., human TIM-3). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein ASepharose®, hydroxylapatite chromatography, gel electrophoresis, dialysis, or affinity chromatography.

Antibodies described herein include antibody fragments which recognize specific TIM-3 (e.g., human TIM-3) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific (e.g., bispecific antibodies) have been described, see, for example, U.S. Pat. Nos. 7,951,917; 7,183,076; 8,227,577; 5,837,242; 5,989, 830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a TIM-3 (e.g., human TIM-3) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of TIM-3 (e.g., human TIM-3) as an anti-TIM-3 (e.g., human TIM-3) antibody described herein, is a human antibody. In particular embodiments, an antibody described herein, which competitively blocks (e.g., in a dose-dependent manner) any one of the antibodies described herein, from binding to TIM-3 (e.g., human TIM-3), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., TIM-3 (e.g., human TIM-3)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the Xenomouse® (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the TransChromo Mouse™ (Kirin) and the KM Mouse™ (Medarex/Kirin), all of which are herein incorporated by reference in their entireties.

Human antibodies which specifically bind to TIM-3 (e.g., human TIM-3) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., TIM-3 (e.g., human TIM-3)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.6 Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated TIM-3 (e.g., human TIM-3) antigen as a control. In another specific embodiment, the kits described herein further comprise a control antibody which does not react with a TIM-3 (e.g., human TIM-3) antigen. In another specific embodiment, kits described herein contain one or more elements for detecting the binding of an antibody to a TIM-3 (e.g., human TIM-3) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized TIM-3 (e.g., human TIM-3) antigen. The TIM-3 (e.g., human TIM-3) antigen provided in the kit can also be attached to a solid support. In a more specific embodiment, the detecting means of the above described kit includes a solid support to which a TIM-3 (e.g., human TIM-3) antigen is attached. Such a kit can also include a non-attached reporter-labeled anti-human antibody or anti-mouse/rat antibody. In this embodiment, binding of the antibody to the TIM-3 (e.g., human TIM-3) antigen can be detected by binding of the said reporter-labeled antibody. In one embodiment, the present invention relates to the use of a kit of the present invention for in vitro assaying and/or detecting TIM-3 antigen (e.g., human TIM-3) in a biological sample.

6. EXAMPLES

The examples in this Section (i.e., Section 6) are offered by way of illustration, and not by way of limitation.

6.1 Example 1: Generation and Characterization of Novel Antibodies Against Human TIM-3

This example describes the generation and characterization of antibodies that bind to human T cell immunoglobulin and mucin domain-3 (TIM-3). In particular, this example describes the generation of human antibodies that specifically bind to human TIM-3 and inhibit the function of human TIM-3.

In some of the studies described below, the activity of the anti-TIM-3 antibodies of this invention was compared with that of reference anti-TIM-3 antibody pab1944w or Hum11. The antibody pab1944w was generated based on the variable regions of the antibody 8213 HV0 LV0 provided in U.S. Pat. No. 8,552,156 (herein incorporated by reference in its entirety). The sequences of pab1944w are shown in Table 7. The antibody pab1944w was expressed as an $IgG_1$ antibody comprising a N297A mutation in the Fc region, numbered according to the EU numbering system. The antibody Hum11 was generated based on the variable regions of the antibody ABTIM3-hum11 provided in U.S. Patent Publication No. US 2015/0218274 (herein incorporated by reference in its entirety). The sequences of Hum11 are shown in Table 7. The antibody Hum11 was expressed as an $IgG_4$ antibody comprising a S228P mutation in the Fc region, numbered according to the EU numbering system.

TABLE 7

Sequences of reference anti-TIM-3 antibodies.

| SEQ ID NO: | Description | Amino acid sequence |
|---|---|---|
| 80 | pab1944w VH | QVQLVQSGAEVKKPGASVKVSCKASGYTFTSYWMHWV RQAPGQGLEWMGEINPSNGRTNYNEKFKTRVTITADTST STAYMELSSLRSEDTAVYYCARGYYLYFDYWGQGTLVT VSS |
| 81 | pab1944w VL | DIQMTQSPSSLSASVGDRVTITCHASQGIRINIGWYQQKPG KAPKLLIYHGTNLEDGVPSRFSGSGSGTDFTLTISSLQPED FATYYCVQYGQFPWTFGQGTKLEIK |
| 89 | pab1944w ($IgG_1$ N297A) full length heavy chain | QVQLVQSGAEVKKPGASVKVSCKASGYTFTSYWMHWV RQAPGQGLEWMGEINPSNGRTNYNEKFKTRVTITADTST STAYMELSSLRSEDTAVYYCARGYYLYFDYWGQGTLVT VSSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKRVEPKSCDKTHTCPPCPAPELL GGPSVFLFPPKPKDTLMISRTPEVTCVVVDVSHEDPEVKF NWYVDGVEVHNAKTKPREEQYASTYRVVSVLTVLHQD WLNGKEYKCKVSNKALPAPIEKTISKAKGQPREPQVYTLP PSREEMTKNQVSLTCLVKGFYPSDIAVEWESNGQPENNY KTTPPVLDSDGSFFLYSKLTVDKSRWQQGNVFSCSVMHE ALHNHYTQKSLSLSPG |
| 90 | pab1944w ($IgG_1$ N297A) full length light chain | DIQMTQSPSSLSASVGDRVTITCHASQGIRINIGWYQQKPG KAPKLLIYHGTNLEDGVPSRFSGSGSGTDFTLTISSLQPED FATYYCVQYGQFPWTFGQGTKLEIKRTVAAPSVFIFPPSD EQLKSGTASVVCLLNNFYPREAKVQWKVDNALQSGNSQ ESVTEQDSKDSTYSLSSTLTLSKADYEKHKVYACEVTHQ GLSSPVTKSFNRGEC |
| 82 | Hum11 VH | QVQLVQSGAEVKKPGSSVKVSCKASGYTFTSYNMHWVR QAPGQGLEWMGDIYPGNGDTSYNQKFKGRVTITADKSTS TVYMELSSLRSEDTAVYYCARVGGAFPMDYWGQGTTVT VSS |
| 83 | Hum11 VL | AIQLTQSPSSLSASVGDRVTITCRASESVEYYGTSLMQWY QQKPGKAPKLLIYAASNVESGVPSRFSGSGSGTDFTLTISS LQPEDFATYFCQQSRKDPSTFGGGTKVEIK |
| 91 | Hum11 ($IgG_4$ S228P) full length heavy chain | QVQLVQSGAEVKKPGSSVKVSCKASGYTFTSYNMHWVR QAPGQGLEWMGDIYPGNGDTSYNQKFKGRVTITADKSTS TVYMELSSLRSEDTAVYYCARVGGAFPMDYWGQGTTVT VSSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEFLGGP SVFLFPPKPKDTLMISRTPEVTCVVVDVSQEDPEVQFNWY VDGVEVHNAKTKPREEQFNSTYRVVSVLTVLHQDWLNG KEYKCKVSNKGLPSSIEKTISKAKGQPREPQVYTLPPSQEE MTKNQVSLTCLVKGFYPSDIAVEWESNGQPENNYKTTPP VLDSDGSFFLYSRLTVDKSRWQEGNVFSCSVMHEALHNH YTQKSLSLSLG |
| 92 | Hum11 ($IgG_4$ S228P) full length light chain | AIQLTQSPSSLSASVGDRVTITCRASESVEYYGTSLMQWY QQKPGKAPKLLIYAASNVESGVPSRFSGSGSGTDFTLTISS LQPEDFATYFCQQSRKDPSTFGGGTKVEIKRTVAAPSVFIF |

TABLE 7-continued

Sequences of reference anti-TIM-3 antibodies.

| SEQ ID NO: | Description | Amino acid sequence |
|---|---|---|
| | | PPSDEQLKSGTASVVCLLNNFYPREAKVQWKVDNALQSG NSQESVTEQDSKDSTYSLSSTLTLSKADYEKHKVYACEVT HQGLSSPVTKSFNRGEC |

6.1.1 Generation of Anti-TIM-3 Antibodies Using Retrocyte Display™ Technology

The generation of a Retrocyte Display™ library is described herein. For the generation of library inserts, total RNA was extracted via phenol/chloroform from FACS sorted CD19 positive human B lymphocytes. The total RNA was used for first-strand cDNA synthesis using RevertAid™ First Strand cDNA Synthesis Kit from Fermentas (Catalog number (Cat#) K1621 and K1622). Antibody variable regions were amplified from the cDNA by PCR and cloned into retroviral expression vectors (pCMA). These constructs were subsequently used to transduce murine preB cells to express antibodies on the surface using Retrocyte Display™ technology.

The Retrocyte Display™ library generated as described above was screened against recombinant human TIM-3 and recombinant cynomolgus TIM-3, leading to the identification of two antibodies, designated as pab2085 and pab2088. The sequence information of the variable regions of pab2085 and pab2088 is summarized in Table 4. The antibodies pab2085 and pab2088 were expressed as IgG$_1$ antibodies and analyzed in the assays described below.

6.1.2 Binding of Anti-TIM-3 Antibodies to TIM-3-Expressing Cells

The antibodies pab2085 and pab2088 were tested for binding to TIM-3-expressing cells using flow cytometry. Briefly, wild type murine 1624-5 cells or 1624-5 cells engineered to express human TIM-3 were incubated with Mouse BD Fc Block™ (Pharmingen, Cat#553142) to reduce non-specific binding. After washing, the cells were stained with an anti-TIM-3 antibody or an isotype control antibody and analyzed using FACSCalibur™ (BD Biosciences). Both pab2085 and pab2088 exhibited binding to 1624-5 cells expressing human TIM-3 but not wild type 1624-5 cells (FIG. 1).

6.1.3 Selectivity Assay for Anti-TIM-3 Antibodies

The selectivity of pab2085 and pab2088 for TIM-3 was assessed against family members TIM-1 and TIM-4 using suspension array technology. Luminex® microspheres were coupled with recombinant human TIM-3 Fc (R&D Systems, Cat#2365-™), recombinant human TIM-3 His (Sino Biological, Cat#10390-H08H), recombinant cynomolgus TIM-3 Fc (R&D Systems, Cat#7914-™), recombinant human TIM-1 His (R&D Systems, Cat#1750-™), or recombinant human TIM-4 His (R&D, Cat#2929-™), via amine coupling with the COOH bead surface. Purified pab2085, pab2088, and an IgG$_1$ isotype control antibody were diluted in assay buffer (Roche, Cat#11112589001) to 10 ng/ml, 100 ng/ml, and 1000 ng/ml. Each dilution (25 µl) was incubated in the dark (20° C., 650 rpm) with 1500 Luminex® microspheres in 5 µl assay buffer for 1 hour in 96 half-well filter plates (Millipore, Cat# MABVN1250). Standard curves were generated using duplicates of 25 µl of a human IgG$_1$ kappa standard (Sigma, Cat#15154) with 1:3 dilution series (0.08-540 ng/ml). Detection was carried out using 60 µl of goat anti-human IgG F(ab)$_2$ labeled with R-PE (2.5 µg/ml; Jackson ImmunoResearch, Cat#109-116-097) and another hour of incubation time (20° C., 650 rpm). Plates were analyzed using a Luminex® 200 system (Millipore). A total of 100 beads were counted per well in a 48 µl sample volume. PE MFI values were used to determine specific or non-specific binding to the recombinant proteins mentioned above.

Both pab2085 (FIG. 2A) and pab2088 (FIG. 2B) showed specific binding to human and cynomolgous TIM-3, and no significant binding to TIM-1 or TIM-4 was observed at the concentrations tested.

6.1.4 Optimization of Anti-TIM-3 Antibodies Using Retrocyte Display™ Technology

The antibodies pab2085 and pab2088 share the same heavy chain. To obtain additional anti-TIM-3 antibodies, a heavy chain Retrocyte Display™ sub-library was generated based on the heavy chain of pab2085 and pab2088 and combined with a more diverse light chain library. This new Retrocyte Display™ library was further screened against recombinant human TIM-3 and recombinant cynomolgus TIM-3, leading to the identification of light-chain optimized variants: pab2173, pab2174, pab2175, pab2176, pab2177, pab2178, pab2179, pab2180, pab2181, pab2182, pab2183, pab2184, pab2185, pab2186, pab2187, pab2188, pab2189, pab2190, pab2191, and pab2192. The sequence information of the variable regions of these light-chain optimized variants is listed in Table 4. The light-chain optimized variants were expressed as antibodies containing a wild type IgG$_1$ Fc region or an IgG$_1$ variant Fc region. This IgG$_1$ variant Fc region does not affect effector functions of the Fc region.

The light-chain optimized antibody pab2188 is an antibody containing a T109S substitution (i.e., substitution of threonine with serine at position 109 relative to the wild type sequence), numbered according to Kabat, in the light chain constant domain, which facilitates the cloning of the variable region in frame to the constant region. This mutation is a conservative modification that does not affect antibody binding or function. The wild type counterpart, designated as pab2188w, which contains a threonine at position 109 of the light chain, numbered according to Kabat, was also generated. The antibody pab2188w was expressed as an antibody containing an IgG$_1$ N297A Fc region.

6.1.5 Binding of Anti-TIM-3 Antibodies to TIM-3-Expressing Cells

The light-chain optimized variants were assessed for binding to cells expressing human or cynomolgus TIM-3 in a flow cytometry assay similar to the one described above. All the variants exhibited binding to murine 1624-5 cells engineered to express human TIM-3 (FIGS. 3A and 3B) or cynomolgus TIM-3 (FIGS. 3C and 3D), but not wild type murine 1624-5 cells (data not shown).

The binding of the light-chain optimized variants to primary human T cells was compared with that of the parental antibody pab2085. Briefly, peripheral blood mononuclear cells (PBMCs) isolated via ficoll gradient from healthy donor buffy coats (Research Blood Components, LLC) were enriched for untouched pan-T cells using magnetic-based separation (Miltenyi Biotec). The enriched population of T lymphocytes was then activated with plate-bound anti-CD3 antibody (SP34, 3 µg/ml) and soluble anti-CD28 antibody (CD28.1, 2 µg/ml) for 3 days in RPMI media, supplemented with 10% heat-inactivated FBS, at 37° C. and 5% $CO_2$. Following activation, cells were incubated with human Fc-receptor block for 15 minutes at room temperature to reduce non-specific binding (FcR block, Biolegend). Anti-TIM-3 or IgG isotype control antibodies (12-point dose titration, 10,000 ng/ml to 0.06 ng/ml) were added to individual samples and incubated for 30 minutes at 4° C. Samples were washed two times and an antibody cocktail, containing FITC-conjugated anti-kappa antibody as well as anti-CD3 (BV711, OKT3), anti-CD4 (BV605, OKT4) and anti-CD8a (PE, RPA-T8, all at 2.5 µg/ml, was diluted in buffer (PBS, 2 mM EDTA, 0.5% BSA, pH 7.2), added to each sample and incubated for 30 minutes at 4° C. Samples were washed two times and analyzed using the LSRFortessa™ flow cytometer (BD Biosciences). Flow cytometry plots were analyzed using a combination of FACSDiva™ and WEHI Weasel software.

As shown in FIG. 4, all the light-chain optimized variants tested in this study showed stronger binding to activated human CD8+ T cells than the parental antibody pab2085 did.

Next, the anti-TIM-3 antibody pab2188 was examined for its binding to primary cynomolgus cells. Cryopreserved PBMCs isolated from cynomolgus monkeys (Worldwide Primates, Inc.) were thawed, washed and then subjected to flow cytometric analysis. Prior to antibody incubation, the cells were treated with 10% cynomolgus monkey serum (Abcam) for 15 minutes at room temperature to reduce non-specific binding. Anti-TIM-3 or IgG isotype control antibodies (10-point dose titration, 20,000 ng/ml to 0.6 ng/ml) were added to individual samples and incubated for 30 minutes at 4° C. Samples were washed two times and an antibody cocktail, containing FITC-conjugated anti-kappa antibody as well as anti-CD11b (BV785, M1/70) at 2.5 µg/ml diluted in buffer (PBS, 2 mM EDTA, 0.5% BSA, pH 7.2), was added to each sample and incubated for 30 minutes at 4° C. Samples were washed two times and analyzed using the LSRFortessa™ flow cytometer (BD Biosciences). Flow cytometry plots were analyzed using a combination of FACSDiva™ and WEHI Weasel software.

As shown in FIG. 5, the anti-TIM-3 antibody pab2188 bound primary cynomolgus myeloid cells in a dose-dependent manner.

6.1.6 Ligand Blocking Activity of Anti-TIM-3 Antibodies

Anti-TIM-3 antibodies were tested for their ability to block the binding of recombinant human or cynomolgus TIM-3 to phosphatidylserine expressed by irradiated WR19L murine lymphoma cells. Anti-TIM-3 or IgG isotype control antibodies (9-point dose titration, 20,000 ng/ml to 70 ng/ml for human; or 6-point dose titration, 20,000 ng/ml to 625 ng/ml for cynomolgus monkey) were incubated with recombinant human TIM-3 Fc (R&D Systems, #2365-™) or recombinant cynomolgus TIM-3 Fc (R&D Systems, #7914-™) (10,000 ng/ml) prepared in 1× Annexin-V binding buffer (10 mM Hepes adjusted to pH 7.4, 140 mM NaCl and 2.5 mM $CaCl_2$)) for 30 minutes at room temperature. WR19L cells irradiated at 20 Gy and resuspended in 1× Annexin-V binding buffer were added to the anti-TIM-3: TIM-3-Fc cocktail at a final density of $1 \times 10^6$ cells/ml and incubated at room temperature for 45 minutes. Samples were washed once and an antibody cocktail, containing PE-conjugated anti-Fc antibody (1:100 dilution) as well as viability stain (Biolegend, NIR channel; 1:1000 dilution) diluted in 1× Annexin-V binding buffer, was added to each sample and incubated for 20 minutes at room temperature. Samples were then washed once in 1× Annexin-V binding buffer, resuspended in 150 µl buffer (PBS, 2 mM EDTA, 0.5% BSA, pH 7.2) and analyzed using the LSRFortessa™ flow cytometer (BD Biosciences). Flow cytometry plots were analyzed using FACSDiva™

The anti-TIM-3 antibodies pab2085 and pab2188 blocked the binding of recombinant human TIM-3 (FIG. 6A) and recombinant cynomolgus TIM-3 (FIG. 6B) to phosphatidylserine.

6.1.7 Effect of Anti-TIM-3 Antibodies on Human PBMCs Upon *Staphylococcus* Enterotoxin A (SEA) Stimulation The functional activity of the light-chain optimized variants on primary human PBMCs were assessed following *Staphylococcus* Enterotoxin A (SEA) stimulation. In brief, cryopreserved human PBMCs (Research Blood Components) were plated at $1 \times 10^5$ cells/well in RPMI1640 supplemented with Normocin™ Antimicrobial Reagent (Invivogen #ant-nr) and 10% heat-inactivated FBS (Gibco™, Invitrogen Corporation) in a 96-well NUNCLON™ delta surface plate (NUNC™). Cells were cultured in the presence of 5 µg/ml of the anti-PD-1 antibody pembrolizumab (lot 7002688300, Myoderm), anti-TIM-3 antibody (10 µg/ml), and the SEA superantigen (100 ng/ml, Toxin Technologies) for 6 days at 37° C. and 5% $CO_2$. Cell-free supernatant was collected and stored at −80° C. until analysis. IFNγ levels were determined using AlphaLISA® (Perkin Elmer).

When combined with the anti-PD-1 antibody pembrolizumab, the light-chain optimized variants enhanced IFNγ production in this primary human PBMC assay (FIG. 7).

The functional activity of pab2188w was analyzed in the SEA stimulation assay using a modified protocol. Cryopreserved human PBMCs (Research Blood Components) were plated at $1 \times 10^5$ cells/well in RPMI1640 supplemented with Normocin™ Antimicrobial Reagent (Invivogen #ant-nr) and 10% heat-inactivated FBS (Gibco™, Invitrogen Corporation) in a 96-well NUNCLON™ delta surface plate (NUNC™). Cells were cultured in the presence of 5 µg/ml of the anti-PD-1 antibody pembrolizumab (lot 7002688300, Myoderm), anti-TIM-3 antibody (10 µg/ml), and the SEA superantigen (100 ng/ml, Toxin Technologies) for 9 days at 37° C. and 5% $CO_2$. The cells were then washed once and re-stimulated with fresh SEA and antibody for 2 days. Cell-free supernatant was collected and stored at −80° C. until analysis. IFNγ levels were determined using AlphaLISA® (Perkin Elmer).

As shown in FIGS. 8A-8F, the anti-TIM-3 antibody pab2188w (IgG$_1$ N297A), either alone or in combination with the anti-PD-1 antibody pembrolizumab, enhanced IFNγ production in human PBMCs from multiple donors in this SEA stimulation assay.

6.2 Example 2: Optimization of Anti-TIM-3 Antibodies Using CDR Mutagenesis

To improve binding affinity, the anti-TIM-3 antibody pab2188w was modified using directed mutagenesis of CDR residues of the heavy and light chain variable regions. Briefly, six Fab phage display libraries were generated based on the parental antibody pab2188w, each containing a CDRH or a CDRL region modified using NNK degenerate codon randomization. The Fab phage libraries were subjected to affinity-driven selections against recombinant human and cynomolgus TIM-3 antigens. Nine clones, designated AM-1, AM-2, AM-3, AM-4, AM-5, AM-6, AM-7, AM-8, and AM-9, were selected based on binding and off-rate measurement. The sequence information of the variable regions of these nine clones is summarized in Table 4. All of these variants share the light chain of pab2188w but contain mutations in heavy chain CDR1. AM-1 to AM-9 were expressed as full length antibodies containing an $IgG_1$ N297A Fc region and analyzed in the experiments described below.

6.2.1 Binding of Anti-TIM-3 Antibodies to TIM-3-Expressing Cells

The binding of antibodies AM-1 to AM-9 to Jurkat cells ectopically expressing human TIM-3 was compared with that of the parental antibody pab2188w in a flow cytometry analysis. As shown in FIG. 9A, all the variants bound to TIM-3-expressing Jurkat cells and AM-2 and AM-6 showed stronger binding than the parental antibody pab2188w did. The binding of AM-2 and AM-6 was further analyzed by flow cytometry using Kasumi-3 (ATCC® CRL-2725™), a human acute myeloid leukemia cell line endogenously expressing TIM-3 (FIG. 9B), as well as human CD8+ T cells stimulated with Staphylococcal Enterotoxin A (SEA) (FIG. 9C) and cynomolgus CD8+ T cells stimulated with SEA (FIG. 9D). For binding to human CD8+ T cells, human PBMCs isolated via ficoll gradient from healthy donor buffy coats (Research Blood Components, LLC) were activated with SEA (100 ng/ml) for 8 days in RPMI media supplemented with 10% heat-inactivated FBS at 37° C. and 5% $CO_2$. Following activation, cells were incubated with human Fc-receptor block for 15 minutes at room temperature to reduce non-specific binding (FcR block, Biolegend). Anti-TIM-3 or IgG isotype control antibodies (12-point dose titration, 10,000 ng/ml to 0.06 ng/ml) were added to individual samples and incubated for 30 minutes at 4° C. Similarly, for binding to cynomolgus CD8+ T cells, isolated cynomolgus PBMCs were thawed from frozen stocks (Worldwide Primates Inc.) and were activated with SEA (100 ng/ml) for five days in RPMI media supplemented with 10% heat-inactivated FBS at 37° C. and 5% $CO_2$. Activated cynomolgus monkey PBMCs were incubated with a combination of human Fc-receptor block (FcR block, Biolegend) and cynomolgus monkey serum (Abcam) for 15 minutes at room temperature to reduce non-specific binding. Phycoerythrin-conjugated AM-2 antibody or isotype control antibody (Biolegend PE-conjugation, 6-point dose titration, 10,000 ng/ml to 41 ng/ml) and a cocktail of anti-CD4 antibody (BV605, OKT4) and anti-CD8a antibody (PE, SK1), each at 2.5 µg/ml, was diluted in buffer (PBS, 2 mM EDTA, 0.5% BSA, pH 7.2), added to each sample, and incubated for 30 minutes at 4° C. Samples were washed two times and an antibody cocktail, containing FITC-conjugated anti-kappa antibody as well as anti-CD3 (BV711, OKT3), anti-CD4 (BV605, OKT4), and anti-CD8a (PE, RPA-T8), all at 2.5 µg/ml, was diluted in buffer (PBS, 2 mM EDTA, 0.5% BSA, pH 7.2), added to each sample, and incubated for 30 minutes at 4° C. Samples were washed two times and analyzed using the LSRFortessa™ flow cytometer (BD Biosciences). Flow cytometry plots were analyzed using a combination of FACSDiva™ and WEHI Weasel software. Both AM-2 and AM-6 exhibited binding to Kasumi-3 cells (FIG. 9B) and activated human CD8+ T cells (FIG. 9C). AM-2 also exhibited binding to activated cynomolgus CD8+ T cells (FIG. 9D).

Next, in a similar assay, binding to primary human and cynomolgus CD14+ myeloid cells was analyzed by flow cytometry using phycoerythrin (PE)-conjugated pab2188w, AM-2, or an isotype control antibody. Briefly, cryopreserved PBMCs isolated from humans or cynomolgus monkeys (Worldwide Primates, Inc.) were thawed, washed, and then subjected to flow cytometric analysis. Prior to antibody incubation, the cells were treated with 10% cynomolgus monkey serum (Abcam, Cat# ab155109) for 15 minutes at room temperature to reduce non-specific binding. PE-conjugated anti-TIM-3 or IgG isotype control antibodies (12-point dose titrations, 10,000 ng/ml to 0.05 ng/ml for human PBMCs and 100,000 ng/ml to 0.5 ng/ml for cynomolgus monkey PBMCs) were added to individual samples in an antibody cocktail containing anti-CD14 antibody (APC, M5E2) and Zombie Green™ fixable viability marker and then incubated for 30 minutes at 4° C. Additional samples were set aside for single stain compensation controls (CD45-FITC, CD45-PE, and CD45-APC; clone MB4-6D6, Miltenyi). Samples were washed two times in buffer and analyzed using LSRFortessa™ flow cytometer (BD Biosciences). Flow cytometry plots were analyzed using a combination of FACSDiva™ and WEHI Weasel software. AM-2 showed stronger binding to human (FIG. 9E) and cynomolgus (FIG. 9F) CD14+ myeloid cells than the parental antibody pab2188w did.

6.2.2 Selectivity Assay for Anti-TIM-3 Antibodies

The selectivity of AM-2 and AM-6 for TIM-3 was assessed using suspension array technology. Luminex® microspheres were coupled with recombinant human TIM-3 His (Sino Biological, #10390-H08H), recombinant cynomolgus TIM-3 Fc (Sino Biological, #90312-C02H), recombinant mouse TIM-3 Fc (R&D Systems, #1529-™), recombinant human TIM-1 His (R&D Systems, #1750-™), recombinant human TIM-4 His (R&D, #2929-™), recombinant human OX40 His (Sino Biological, #10481-H08H), recombinant human GITR Fc (R&D Systems, #689-GR), recombinant human DR3 Fc (R&D Systems, #943-D3), and recombinant human CD137 Fc (in house produced material), via amine coupling with the COOH bead surface. Purified pab2188w ($IgG_1$ N297A), AM-2 ($IgG_1$ N297A), AM-6 ($IgG_1$ N297A), and an $IgG_1$ N297A isotype control antibody were diluted in assay buffer (Roche 11112589001) to a dose titration from 10000 ng/ml to 0.1 ng/ml. Each dilution (25 µl) was incubated in the dark (20° C., 650 rpm) with 1500 Luminex® microspheres in 5 µl assay buffer for 1 hour in 96 half-well filter plates (Millipore, MABVN1250). Detection was carried out using 60 µl of goat anti-human IgG F(ab)$_2$ labeled with R-PE (2.5 µg/ml; JIR 109-116-097) and another hour of incubation time (20° C., 650 rpm). Plates were analyzed using a Luminex® 200 system (Millipore). A total of 100 beads were counted per well in a 48 µl sample volume. PE MFI values were used to determine specific or non-specific binding to the recombinant proteins.

The anti-TIM-3 antibodies pab2188w (FIG. 10B), AM-2 (FIG. 10C), and AM-6 (FIG. 10D) showed specific binding to human and cynomolgous TIM-3, and no significant binding was detected to mouse TIM-3, human TIM-1, human TIM-4, human OX40, human GITR, human DR3, or human CD137 at tested concentrations.

6.2.3 Ligand Blocking Activity of Anti-TIM-3 Antibodies

The anti-TIM-3 antibodies AM-2 and AM-6 were further analyzed for their ability to block the binding of phosphatidylserine to human or cynomolgus TIM-3. Briefly, anti-TIM-3 or IgG isotype control antibodies (10-point dose titration, 40,000 ng/ml to 1000 ng/ml) were incubated with recombinant human TIM-3 Fc (R&D Systems, #2365-™) or recombinant cynomolgus TIM-3 Fc (R&D Systems, #7914-™) (10,000 ng/ml) prepared in 1× Annexin-V binding buffer (10 mM Hepes adjusted to pH 7.4, 140 mM NaCl and 2.5 mM $CaCl_2$) for 30 minutes at room temperature. WR19L cells irradiated at 20 Gy and resuspended in 1× Annexin-V binding buffer were added to the anti-TIM-3: TIM-3-Fc cocktail at a final density of 1×10⁶ cells/ml and incubated at room temperature for 45 minutes. Samples were washed once and an antibody cocktail, containing PE-conjugated anti-Fc antibody (1:100 dilution) as well as viability stain (Biolegend, NIR channel; 1:1000 dilution) diluted in 1× Annexin-V binding buffer, was added to each sample and incubated for 20 minutes at room temperature. Samples were then washed once in 1× Annexin-V binding buffer and analyzed using the LSRFortessa™ flow cytometer (BD Biosciences). Flow cytometry plots were analyzed using FACSDiva™

As shown in FIGS. 11A and 11B, the anti-TIM-3 antibodies pab2188w, AM-2, and AM-6 effectively blocked the binding of human or cynomolgus TIM-3 to phosphatidylserine-expressing cells.

6.2.4 Effect of Anti-TIM-3 Antibodies on Human PBMCs Upon *Staphylococcus* Enterotoxin A (SEA) Stimulation The functional activity of the variants of pab2188w was analyzed using primary human PBMCs stimulated by *Staphylococcus* Enterotoxin A (SEA). Briefly, cryopreserved human PBMCs (Research Blood Components) were plated at 1×10⁵ cells/well in RPMI1640 supplemented with Normocin™ Antimicrobial Reagent (Invivogen #ant-nr) and 10% heat-inactivated FBS (Gibco™, Invitrogen Corporation) in 96-well NUNCLON™ delta surface plates (NUNC™). Cells were cultured in the presence of 5 µg/ml of the anti-PD-1 antibody pembrolizumab (lot 7002688300, Myoderm), anti-TIM-3 antibody (10 µg/ml), and the SEA superantigen (100 ng/ml, Toxin Technologies) for 9 days at 37° C. and 5% CO₂. The cells were then washed once and re-stimulated with fresh SEA and antibody for 2 days. Cell-free supernatant was collected and stored at −80° C. until analysis. IFNγ levels were determined using AlphaLISA® (Perkin Elmer).

As shown in FIGS. 12A and 12B, many variants of pab2188w, either alone or in combination with the anti-PD-1 antibody pembrolizumab, enhanced IFNγ production in human PBMCs from two different donors.

6.2.5 Effect of Anti-TIM-3 Antibodies on Cytokine Production of Tumor Infiltrating Lymphocytes The anti-TIM-3 antibodies were further assessed for their ability to stimulate cytokine production of activated primary tumor infiltrating lymphocytes (TILs), alone or in combination with an anti-PD-1 antibody. Single-cell suspensions from fresh non-small cell lung cancer (NSCLC) (stage II), gallbladder adenocarcinoma (stage IV), or breast cancer (stage II) tumors (UMass Medical School, Worcester, Mass.) were isolated via mechanical microdissection. In some cases, depending on the level of fibrosis, enzymatic digestion was necessary (Liberase and DNAseI, Roche). Cells were rested at 5×10⁴ cells/well in RPMI1640 supplemented with Normocin™ Antimicrobial Reagent (Invivogen #ant-nr), recombinant human IL-2 (20 U/ml, R&D Systems), and 10% heat-inactivated FBS (Gibco™, Invitrogen Corporation) in 96-well NUNCLON™ delta surface plates (NUNC™) for 1 day. On the following day, the samples were centrifuged and fresh culture media containing the antibodies of interest (anti-TIM-3 antibodies at 20 µg/ml and the anti-PD-1 antibody pembrolizumab at 5 µg/ml) and anti-CD3/CD28 microbeads (1:1 bead:cell ratio) was added at a final volume of 100 µl and allowed to incubate for 3 days at 37° C. and 5% CO₂. Cell-free supernatant was collected and stored at −80° C. until analysis. IFNγ and TNFα levels were determined using AlphaLISA® (Perkin Elmer).

As shown in FIGS. 13A-13F, the anti-TIM-3 antibodies enhanced IFNγ and TNFα production by activated primary TILs from NSCLC, gallbladder adenocarcinoma, or breast cancer tumors.

6.2.6 Internalization of Anti-TIM-3 Antibodies Upon Binding

In this example, internalization of anti-TIM-3 antibodies into cells was analyzed. In a first set of experiments, anti-TIM-3 antibody internalization was assessed using αHFc-NC-DM1 (anti-human IgG Fc antibody conjugated to maytansinoid DM1 with a non-cleavable linker, Moradec LLC). This secondary antibody drug conjugate αHFc-NC-DM1 binds to a test antibody (e.g., an anti-TIM-3 antibody) and results in release of the cytotoxic payload DM1 into the cytoplasm of the cell upon internalization. In a second set of experiments, internalization was evaluated using anti-TIM-3 antibodies pab2188w (IgG₁ N297A) and Hum11 (IgG₄ S228P) directly conjugated to monomethyl auristatin E (MMAE). Each antibody exhibited similar drug-antibody ratios (DAR; Isotype control=3.5, pab2188w=4.0, Hum11=3.0), supporting an equivalent level of antibody-drug conjugate (ADC) delivery upon internalization. In a third set of experiments, internalization was assessed by the subcellular localization of a TIM-3 protein labeled with a cell-impermeable fluorescent dye.

Briefly, Kasumi-3 (ATCC® CRL-2725™), an acute myeloid leukemia cell line endogenously expressing TIM-3, and a Jurkat cell line engineered to overexpress TIM-3 were plated in white-bottom tissue culture plates at a density of 2×10⁴ per well. For the first set of experiments using the secondary antibody drug conjugate αHFc-NC-DM1, an 8-point dose titration (3,333 ng/ml to 1 ng/ml) of either anti-TIM-3 antibody or IgG isotype control antibody in concert with αHFc-NC-DM1 (1:1 with the primary antibody) was added to the cells at a final volume of 100 µl/well. The cells were incubated with the primary antibodies and the secondary antibody drug conjugate at 37° C. and 5% CO₂ for 72 hours.

The anti-TIM-3 antibodies pab2188w (IgG₁ N297A), AM-2 (IgG₁ N297A), and AM-6 (IgG₁ N297A) internalized TIM-3 expressed on Jurkat cells (FIG. 14A) and Kasumi-3 cells (FIG. 14B) in the αHFc-NC-DM1 experiments more effectively than the reference anti-TIM-3 antibodies Hum11 (IgG₄ S228P) and pab1944w (IgG₁ N297A) did, as evidenced by a greater reduction of cell survival across a broad range of antibody concentrations.

For the second set of experiments, antibodies pab2188w (IgG1 N297A) and Hum11 (ref, IgG4 S228P) were directly conjugated to similar concentrations of MMAE to account for potential differences in the propensity of the secondary drug conjugate (αHFc-NC-DM1) to bind the different Fc regions of the antibodies. A 9-point dose titration (6,666 ng/ml to 1 ng/ml) of either MMAE-conjugated anti-TIM-3 antibody or MMAE-conjugated IgG isotype control antibody was added to the cells at a final volume of 100 µl/well. The cells were incubated with the conjugated antibodies at 37° C. and 5% CO₂ for 72 hours. Following incubation, 90 µl of reconstituted Cell Titer-Gb® Luminescent Cell Viability Assay (Promega) was added to each well and the cells were incubated at room temperature for 5 minutes. The resulting luminescence was recorded using Envision® Plate Reader (Perkin Elmer).

As shown in FIG. 14C, antibody pab2188w (IgG1 N297A) induced a greater reduction of cell survival than did antibody Hum11 (ref, IgG4 S228P), indicating that the effect observed with the secondary antibody drug conjugate (e.g., as shown in FIG. 14A), was attributable to the internalization potential of each TIM-3 antibody.

In the third set of experiments, internalization of anti-TIM-3 antibodies was analyzed by confocal fluorescence microscopy of live cells. Jurkat cells expressing a HaloTag®-TIM-3 fusion protein were first incubated with 1 μM Violet Proliferation Dye 450 (BD Horizon™) for 30 minutes at 37° C. and 5% $CO_2$. After incubation, cells were washed in PBS and resuspended in cell culture media. To detect the extracellular domain of TIM-3, the Jurkat HaloTag®-TIM-3 cells were stained with a membrane-impermeable HaloTag® AlexaFluor® 488 ligand (Promega, 1 μM) for 15 minutes at 37° C. and 5% $CO_2$. Cells were then resuspended in fresh culture media and plated in a 384-well microscopy plate (15,000 cells/well) with either anti-TIM-3 antibody AM-2 ($IgG_1$ N297A) or an isotype control (each antibody at 10m/ml). Live images were collected using an ImageXpress® Micro Confocal High-Content microscope (Molecular Devices) under environmental control (37° C. and 5% $CO_2$) and images were acquired every 30 minutes over a course of 3.5 hours. Image analysis was performed using MetaXpress® analysis software (Molecular Devices). Jurkat cells were identified from the DAPI channel (Violet Proliferation Dye 450 (BD Horizon™)) and the amount of internalized TIM-3 signal was quantified per cell from the FITC channel (HaloTag® Alexa Fluor® 488).

As shown in FIG. 15, an increase in TIM-3 internalization over time was observed for cells incubated with anti-TIM-3 antibody AM-2 relative to cells incubated with isotype control antibody. In particular, after 3.5 hours, AM-2 antibody treatment resulted in twice the percentage of TIM-3-positive cells showing TIM-3 internalization compared to TIM-3-positive cells treated with the isotype control antibody (i.e., 15.1% internalization versus 7.2% internalization, respectively). Further, the internalization signal observed for AM-2 antibody-treated cells was significantly higher at 3.5 hours than that of cells treated with isotype control antibody (p=0.00027, one-tailed T test). There was no statistically significant difference at the 0-hour time point (p=0.91, one-tailed T-test).

6.3 Example 3: Epitope Mapping of Anti-TIM-3 Antibodies

In this example, the epitope of the anti-TIM-3 antibodies pab2188 ($IgG_1$ variant), pab2187 ($IgG_1$ variant), and AM-2 ($IgG_1$ N297A) was characterized.

6.3.1 Epitope Mapping of Anti-TIM-3 Antibodies Using Alanine Scanning

The binding characteristics of the anti-TIM-3 antibodies pab2188 ($IgG_1$ variant) and pab2187 ($IgG_1$ variant) were assessed by alanine scanning. Briefly, the QuikChange® HT Protein Engineering System from Agilent Technologies (Cat# G5901A) was used to generate human TIM-3 mutants with alanine substitutions in the extracellular domain. The human TIM-3 mutants were expressed on the surface of the murine 1624-5 pre-B cells using retroviral transduction. The transduction efficiency or the percentage of cells expressing human TIM-3 was kept below 5% to ensure that most cells did not express two or more different TIM-3 mutants.

Cells expressing correctly folded human TIM-3 mutants, as evidenced by binding to a polyclonal anti-TIM-3 antibody (R&D Systems, Cat# AF2365) in flow cytometry, were further selected for a sub-population that expressed human TIM-3 mutants that did not bind the monoclonal anti-TIM-3 antibody pab2188 ($IgG_1$ variant) or pab2187 ($IgG_1$ variant). Cells that exhibited specific antibody binding were separated from the non-binding cell population by preparative, high-speed FACS (FACSAria™ II, BD Biosciences). Antibody reactive or non-reactive cell pools were expanded again in tissue culture and cycles of antibody-directed cell sorting and tissue culture expansion were repeated until a clearly detectable anti-TIM-3 antibody (pab2188 ($IgG_1$ variant) or pab2187 ($IgG_1$ variant)) non-reactive cell population was obtained. This anti-TIM-3 antibody (pab2188 ($IgG_1$ variant) or pab2187 ($IgG_1$ variant)) non-reactive cell population was subjected to a final, single-cell or bulk sorting step. After several days of cell expansion, single-cell or bulk sorted cells were again tested for binding to the polyclonal anti-TIM-3 antibody and non-binding to the monoclonal antibody pab2188 ($IgG_1$ variant) or pab2187 ($IgG_1$ variant) using flow cytometry.

To connect phenotype with genotype, NGS sequencing was performed on bulk sorted cells expressing human TIM-3 mutants. Sequence analysis showed that the cells that were reactive to the polyclonal anti-TIM-3 antibody but not the monoclonal anti-TIM-3 antibody pab2188 ($IgG_1$ variant) or pab2187 ($IgG_1$ variant) expressed a human TIM-3 mutant in which position 40 was mutated from a Phe to an Ala, numbered according to SEQ ID NO: 79.

6.3.2 Epitope Mapping of Anti-TIM-3 Antibodies Using Hydrogen-Deuterium Exchange (HDX) Mass Spectrometry In a first study, the interaction of pab2188 ($IgG_1$ variant) with human TIM-3 was studied using hydrogen-deuterium exchange (HDX) mass spectrometry.

For deglycosylation treatment, 250 μg of recombinant human TIM-3/Fc chimera (R&D Systems, Cat#2365-™) was incubated with 4 μl of PNGase F at 37° C. for 3 hours. The human TIM-3/Fc chimera comprises the amino acid sequence of SEQ ID NO: 102 fused to human $IgG_1$.

For pepsin digestion, 6.9 μg of native or deglycosylated human TIM-3/Fc chimera in 115 μl control buffer (50 mM phosphate, 100 mM sodium chloride, pH 7.4) was denatured by adding 115 μl of 4 M guanidine hydrochloride, 0.85 M TCEP buffer (final pH 2.5), and incubating the mixture for 3 minutes at 10° C. Then, the mixture was subjected to on-column pepsin digestion using an in-house packed pepsin column and the resultant peptides were analyzed using a UPLC-MS system comprised of a Waters Acquity UPLC coupled to a Q Exactive™ Hybrid Quadrupole-Orbitrap™ Mass Spectrometer (Thermo Scientific). The peptides were separated on a 50 mm×1 mm C8 column with a 20.5-minute gradient from 2-32% solvent B (0.1% formic acid in acetonitrile). Peptide identification was conducted through searching MS/MS data against the human TIM-3 sequence with Mascot software. The mass tolerance for the precursor and product ions was 20 ppm and 0.05 Da, respectively.

10 μl native or deglycosylated human TIM-3/Fc chimera (6.9 μg), 10 μl native human TIM-3/Fc chimera and antibody mixture (6.9 μg: 12.9 μg), or 10 μl deglycosylated human TIM-3/Fc chimera and antibody mixture (6.9 μg: 12.9 μg) was incubated with 105 μl deuterium oxide labeling buffer (50 mM phosphate, 100 mM sodium chloride, pD 7.4) for 0 second, 60 seconds, 300 seconds, 1800 seconds, 7200 seconds, 14400 seconds, and 28800 seconds. Deuterium exchange was conducted either at 10° C. for native human TIM-3/Fc chimera and its complex with antibody or at 4° C. for deglycosylated human TIM-3/Fc chimera and its complex with antibody. Deuterium exchange was quenched by adding 115 μl of 4 M guanidine hydrochloride, 0.85 M TCEP buffer (final pH 2.5). Subsequently, the quenched sample was subjected to on-column pepsin digestion and LC-MS analysis as described above. The mass spectra were recorded in MS only mode. For calculation of deuterium incorporation, the mass spectra for a given peptide were combined across the extracted ion chromatogram peaks and the weighted average m/z was calculated. Mass increase from the mass of the native peptide (0 minute) to the weighted averaged mass corresponds to the level of deuterium incorporation.

The sequence coverage achieved for native and deglycosylated human TIM-3 was 71.6% and 98.4%, respectively. While most human TIM-3 peptides displayed identical or similar deuterium levels with and without the anti-human TIM-3 antibody, several peptide segments were found to have significantly decreased deuterium incorporation upon antibody binding. Both native and deglycosylated human TIM-3 showed significant reduction in deuterium uptake upon binding to anti-human TIM-3 antibody pab2188 (IgG$_1$ variant) at a region consisting of the amino acid sequence of SEQ ID NO: 94 (VCWGKGACPVFECGNVVL) and a region consisting of the amino acid sequence of SEQ ID NO: 95 (RIQIPGIMND). The strongest decrease in deuterium uptake was observed at a region consisting of the amino acid sequence of SEQ ID NO: 93 (PVFECGN).

Next, the interaction of AM-2 (IgG$_1$ N297A) with human TIM-3 was studied in a HDX mass spectrometry study similar to the one described above. Briefly, deglycosylated human TIM-3/Fc chimera was incubated in deuterium oxide either alone or in complex with the anti-human TIM-3 antibody AM-2 (IgG$_1$ N297A). The deuterium exchange was carried at 10° C. for 0 second, 60 seconds, 300 seconds, 1800 seconds, 7200 seconds, and 14400 seconds. The exchange reaction was quenched by low pH and the quenched samples were subjected to on-column pepsin/protease XIII or protease XVIII digestion and LC-MS analysis as described above. Raw MS data were processed using HDX WorkBench, software for the analysis of H/D exchange MS data (J. Am. Soc. Mass Spectrom. 2012, 23 (9), 1512-1521, herein incorporated by reference in its entirety). The deuterium levels were calculated using the average mass difference between the deuterated peptide and its native form (t$_0$).

A hundred percent sequence coverage was achieved for deglycosylated human TIM-3. The anti-TIM-3 antibody AM-2 (IgG$_1$ N297A) showed a similar binding pattern as the one exhibited by pab2188 (IgG$_1$ variant). Two regions, one consisting of the amino acid sequence of SEQ ID NO: 94 (VCWGKGACPVFECGNVVL) and the other consisting of the amino acid sequence of SEQ ID NO: 96 (RIQIPGIMNDEKFNLKL), experienced strong deuterium protection when deglycosylated human TIM-3 was bound to the anti-TIM-3 antibody AM-2 (IgG$_1$ N297A). The strongest decrease was observed at a region consisting of the amino acid sequence of SEQ ID NO: 93 (PVFECGN).

6.3.3 Epitope Mapping of Anti-TIM-3 Antibody Using Pepscan Analysis

The binding of anti-TIM-3 antibody pab2188 (IgG$_1$ variant) was measured against synthetic TIM-3-related peptide fragments prepared as a chip-bound peptide array. Analysis was performed by Pepscan Presto BV, Lelystad, the Netherlands. Briefly, to reconstruct epitopes of human TIM-3, a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was conducted using Pepscan's proprietary Chemically Linked Peptides on Scaffolds (CLIPS) technology. CLIPS technology permits structuring peptides into single loops, double loops, triple loops, sheet-like folds, helix-like folds and combinations thereof. The binding of antibody to each of the synthesized peptides was tested in a PEPSCAN-based ELISA. The peptide arrays were incubated with primary antibody solution overnight at 4° C. After washing, the peptide arrays were incubated with a goat anti-human HRP conjugate (Southern Biotech, Cat#2010-05) for one hour at 25° C. After washing, the peroxidase substrate 2,2'-azino-di-3-ethylbenzthiazoline sulfonate (ABTS) and 2 µl/ml of 3% H$_2$O$_2$ were added. After one hour, the color development was measured and quantified with a charge coupled device (CCD)—camera and an image processing system.

The Pepscan study showed that the anti-TIM-3 antibody pab2188 (IgG$_1$ variant) recognized stretches of human TIM-3 including a region consisting of the amino acid sequence of SEQ ID NO: 99 (GKGACPVFE) and a region consisting of the amino acid sequence of SEQ ID NO: 100 (DFTAAFPR).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed is:

1. An isolated antibody that specifically binds to human TIM-3, the antibody comprising a heavy chain variable region comprising complementarity determining regions CDRH1, CDRH2 and CDRH3 and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 14, 21, and 22; 4, 2, 3, 14, 21, and 22; 5, 2, 3, 14, 21, and 22; 6, 2, 3, 14, 21, and 22; 7, 2, 3, 14, 21, and 22; 8, 2, 3, 14, 21, and 22; 9, 2, 3, 14, 21, and 22; 10, 2, 3, 14, 21, and 22; 11, 2, 3, 14, 21, and 22; 12, 2, 3, 14, 21, and 22; or 1, 2, 3, 15, 18, and 22, respectively.

2. The isolated antibody of claim 1, wherein CDRH1, CDRH2, CDRH3, CDRL1, CDRL2, and CDRL3 comprise the amino acid sequences set forth in SEQ ID NOs: 5, 2, 3, 14, 21, and 22, respectively.

3. The isolated antibody of claim 1, wherein the antibody comprises a heavy chain variable region comprising the amino acid sequence of SEQ ID NO: 55.

4. The isolated antibody of claim 1, wherein the antibody comprises a heavy chain variable region comprising an amino acid sequence which is at least 75%, 80%, 85%, 90%, 95%, or 100% identical to an amino acid sequence selected from the group consisting of SEQ ID NOs: 24-27 and 29-35.

5. The isolated antibody of claim 1, wherein the heavy chain variable region comprises an amino acid sequence selected from the group consisting of SEQ ID NOs: 24-27 and 29-35.

6. The isolated antibody of claim 1, wherein the antibody comprises a light chain variable region comprising the amino acid sequence of SEQ ID NO: 56.

7. The isolated antibody of claim 1, wherein the antibody comprises a light chain variable region comprising an amino acid sequence which is at least 75%, 80%, 85%, 90%, 95%, or 100% identical to an amino acid sequence selected from the group consisting of SEQ ID NOs: 36-45 and 47.

8. The isolated antibody of claim 1, wherein the light chain variable region comprises an amino acid sequence selected from the group consisting of SEQ ID NOs: 36-45 and 47.

9. The isolated antibody of claim 1, wherein the antibody comprises a heavy chain comprising the amino acid sequence of SEQ ID NO: 58 or 65.

10. The isolated antibody of claim 1, wherein the heavy chain variable region and the light chain variable region, respectively, comprise the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 29 and 46; 30 and 46; 31 and 46; 32 and 46; 33 and 46; 34 and 46; or 35 and 46.

11. The isolated antibody of claim 10, wherein the amino acid sequences of the heavy chain variable region and the light chain variable region, respectively, consist of the amino acid sequences set forth in SEQ ID NOs: 24 and 36; 24 and 38; 26 and 42; 24 and 42; 24 and 46; 24 and 43; 26 and 43; 26 and 46; 26 and 41; 24 and 41; 25 and 39; 24 and 47; 25 and 40; 26 and 47; 25 and 37; 25 and 45; 25 and 44; 25 and 46; 25 and 42; 25 and 41; 25 and 43; 25 and 47; 27 and 46; 29 and 46; 30 and 46; 31 and 46; 32 and 46; 33 and 46; 34 and 46; or 35 and 46.

12. The isolated antibody of claim 1, comprising a heavy chain and a light chain, wherein the heavy chain and the light chain, respectively, comprise the amino acid sequences set forth in SEQ ID NOs: 58 and 69; or 65 and 69.

13. The isolated antibody of claim 12, wherein the amino acid sequences of the heavy chain and the light chain, respectively, consist of the amino acid sequences set forth in SEQ ID NOs: 58 and 69; or 65 and 69.

14. The isolated antibody of any claim 1, wherein the antibody is internalized upon binding to cells expressing human TIM-3.

15. The isolated antibody of claim 1, wherein the antibody comprises a heavy chain constant region selected from the group consisting of human $IgG_1$, $IgG_2$, $IgG_3$, $IgG_4$, $IgA_1$, and $IgA_2$.

16. The isolated antibody of claim 15, wherein the heavy chain constant region is an $IgG_1$ heavy chain constant region.

17. The isolated antibody of claim 16, wherein the amino acid sequence of the $IgG_1$ heavy chain constant region comprises a N297A mutation, numbered according to the EU numbering system.

18. The isolated antibody of claim 17, wherein the antibody comprises a heavy chain constant region comprising the amino acid sequence of SEQ ID NO: 72.

19. The isolated antibody of claim 16, wherein the amino acid sequence of the $IgG_1$ heavy chain constant region comprises a N297Q mutation, numbered according to the EU numbering system.

20. The isolated antibody of claim 16, wherein the $IgG_1$ heavy chain constant region is non-fucosylated.

21. The isolated antibody of claim 15, wherein the heavy chain constant region is an $IgG_4$ heavy chain constant region.

22. The isolated antibody of claim 21, wherein the amino acid sequence of the $IgG_4$ heavy chain constant region comprises a S228P mutation, numbered according to the EU numbering system.

23. The isolated antibody of claim 22, wherein the antibody comprises a heavy chain constant region comprising the amino acid sequence of SEQ ID NO: 74.

24. The isolated antibody of claim 1, wherein the antibody comprises a human kappa or human lamda light chain constant region.

25. The isolated antibody of claim 24, wherein the light chain constant region is a human kappa light chain constant region.

26. The isolated antibody of claim 25, wherein the antibody comprises a light chain constant region comprising the amino acid sequence of SEQ ID NO: 76.

27. The isolated antibody of claim 1, wherein the antibody is a human antibody.

28. The isolated antibody of claim 1, wherein the antibody is antagonistic to human TIM-3.

29. The isolated antibody of claim 1, wherein the antibody deactivates, reduces, or inhibits an activity of human TIM-3.

30. The isolated antibody of claim 1, wherein the antibody inhibits binding of human TIM-3 to phosphatidylserine.

31. The isolated antibody of claim 1 conjugated to a cytotoxic agent, cytostatic agent, toxin, radionuclide, or detectable label.

32. A pharmaceutical composition comprising the antibody of claim 1 and a pharmaceutically acceptable carrier or excipient.

* * * * *

SEQUENCE LISTING

```
<160> NUMBER OF SEQ ID NOS: 102

<210> SEQ ID NO 1
<211> LENGTH: 6
<212> TYPE: PRT
<213> ORGANISM: Artificial Sequence
<220> FEATURE:
<223> OTHER INFORMATION: BADD456-2919 CDRH1

<400> SEQUENCE: 1
```

Ser Ser Tyr Ala Met Ser
1               5

<210> SEQ ID NO 2
<211> LENGTH: 13
<212> TYPE: PRT
<213> ORGANISM: Artificial Sequence
<220> FEATURE:
<223> OTHER INFORMATION: BADD456-2919 CDRH2

<400> SEQUENCE: 2

Trp Val Ser Ala Ile Ser Gly Ser Gly Gly Ser Thr Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: BADD456-2919 CDRH3

<400> SEQUENCE: 3

Ala Lys Gly Gly Asp Tyr Gly Gly Asn Tyr Phe Asp
1               5                   10

<210> SEQ ID NO 4
<211> LENGTH: 6
<212> TYPE: PRT
<213> ORGANISM: Artificial Sequence
<220> FEATURE:
<223> OTHER INFORMATION: AM-1 CDRH1

<400> SEQUENCE: 4

Lys Ala Gly Gln Ser Ser
1               5

<210> SEQ ID NO 5
<211> LENGTH: 6
<212> TYPE: PRT
<213> ORGANISM: Artificial Sequence
<220> FEATURE:
<223> OTHER INFORMATION: AM-2 CDRH1

<400> SEQUENCE: 5

Arg Gln Asn Ala Trp Ser
1               5

<210> SEQ ID NO 6
<211> LENGTH: 6
<212> TYPE: PRT
<213> ORGANISM: Artificial Sequence
<220> FEATURE:
<223> OTHER INFORMATION: AM-3 CDRH1

<400> SEQUENCE: 6

Met Ser Gly Gln Thr Ser
1               5

<210> SEQ ID NO 7
<211> LENGTH: 6
<212> TYPE: PRT
<213> ORGANISM: Artificial Sequence
<220> FEATURE:
<223> OTHER INFORMATION: AM-4 CDRH1

<400> SEQUENCE: 7

Gly Ala Gly Gln Ser Ser

```
<210> SEQ ID NO 8
<211> LENGTH: 6
<212> TYPE: PRT
<213> ORGANISM: Artificial Sequence
<220> FEATURE:
<223> OTHER INFORMATION: AM-5 CDRH1

<400> SEQUENCE: 8

Ser Ala Gln Gln Ala Ser
1               5

<210> SEQ ID NO 9
<211> LENGTH: 6
<212> TYPE: PRT
<213> ORGANISM: Artificial Sequence
<220> FEATURE:
<223> OTHER INFORMATION: AM-6 CDRH1

<400> SEQUENCE: 9

Ala Arg Asn Ala Trp Ser
1               5

<210> SEQ ID NO 10
<211> LENGTH: 6
<212> TYPE: PRT
<213> ORGANISM: Artificial Sequence
<220> FEATURE:
<223> OTHER INFORMATION: AM-7 CDRH1

<400> SEQUENCE: 10

Arg Ser Gln Gln Ala Ser
1               5

<210> SEQ ID NO 11
<211> LENGTH: 6
<212> TYPE: PRT
<213> ORGANISM: Artificial Sequence
<220> FEATURE:
<223> OTHER INFORMATION: AM-8 CDRH1

<400> SEQUENCE: 11

Thr Thr Gln Gln Ala Ser
1               5

<210> SEQ ID NO 12
<211> LENGTH: 6
<212> TYPE: PRT
<213> ORGANISM: Artificial Sequence
<220> FEATURE:
<223> OTHER INFORMATION: AM-9 CDRH1

<400> SEQUENCE: 12

Gly Gly Gln Gln Ala Ser
1               5

<210> SEQ ID NO 13
<211> LENGTH: 12
<212> TYPE: PRT
<213> ORGANISM: Artificial Sequence
<220> FEATURE:
<223> OTHER INFORMATION: BADD197-1181 CDRL1

<400> SEQUENCE: 13

Arg Ala Ser Gln Ser Val Ser Ser Ser Tyr Leu Ala
1               5                   10
```

```
<210> SEQ ID NO 14
<211> LENGTH: 11
<212> TYPE: PRT
<213> ORGANISM: Artificial Sequence
<220> FEATURE:
<223> OTHER INFORMATION: BADD412-2513 CDRL1

<400> SEQUENCE: 14

Arg Ala Ser Gln Ser Val Ser Ser Tyr Leu Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: BADD456-2928 CDRL1

<400> SEQUENCE: 15

Arg Ala Ser Gln Gly Ile Ser Asn Tyr Leu Ala
1               5                   10

<210> SEQ ID NO 16
<211> LENGTH: 12
<212> TYPE: PRT
<213> ORGANISM: Artificial Sequence
<220> FEATURE:
<223> OTHER INFORMATION: BADD466-3169 CDRL1

<400> SEQUENCE: 16

Gly Ala Ser Gln Ser Val Ser Ser Ser Tyr Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: BADD197-1181 CDRL2

<400> SEQUENCE: 17

Gly Ala Ser Ser Arg Ala Thr
1               5

<210> SEQ ID NO 18
<211> LENGTH: 7
<212> TYPE: PRT
<213> ORGANISM: Artificial Sequence
<220> FEATURE:
<223> OTHER INFORMATION: BADD456-2928 CDRL2

<400> SEQUENCE: 18

Ala Ala Ser Thr Leu Gln Ser
1               5

<210> SEQ ID NO 19
<211> LENGTH: 7
<212> TYPE: PRT
<213> ORGANISM: Artificial Sequence
<220> FEATURE:
<223> OTHER INFORMATION: BADD466-3165 CDRL2

<400> SEQUENCE: 19

Gly Ala Ser Thr Arg Ala Thr
1               5
```

<210> SEQ ID NO 20
<211> LENGTH: 7
<212> TYPE: PRT
<213> ORGANISM: Artificial Sequence
<220> FEATURE:
<223> OTHER INFORMATION: BADD466-3166 CDRL2

<400> SEQUENCE: 20

Asp Ala Ser Ser Arg Ala Thr
1               5

<210> SEQ ID NO 21
<211> LENGTH: 7
<212> TYPE: PRT
<213> ORGANISM: Artificial Sequence
<220> FEATURE:
<223> OTHER INFORMATION: BADD466-3167 CDRL2

<400> SEQUENCE: 21

Asp Ala Ser Asn Arg Ala Thr
1               5

<210> SEQ ID NO 22
<211> LENGTH: 9
<212> TYPE: PRT
<213> ORGANISM: Artificial Sequence
<220> FEATURE:
<223> OTHER INFORMATION: BADD197-1181 CDRL3

<400> SEQUENCE: 22

Gln Gln Tyr Gly Ser Ser Pro Leu Thr
1               5

<210> SEQ ID NO 23
<211> LENGTH: 9
<212> TYPE: PRT
<213> ORGANISM: Artificial Sequence
<220> FEATURE:
<223> OTHER INFORMATION: BADD392-2234 CDRL3

<400> SEQUENCE: 23

Gln Gln Tyr Gly Ser Ser Pro Ile Thr
1               5

<210> SEQ ID NO 24
<211> LENGTH: 120
<212> TYPE: PRT
<213> ORGANISM: Artificial Sequence
<220> FEATURE:
<223> OTHER INFORMATION: BADD456-2919 VH

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: BADD466-3162 VH

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: BADD466-3163 VH

<400> SEQUENCE: 26

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 27
<211> LENGTH: 120
<212> TYPE: PRT

<213> ORGANISM: Artificial Sequence
<220> FEATURE:
<223> OTHER INFORMATION: AM-1-VH

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Ala Gly
            20                  25                  30

Gln Ser Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120
```

<210> SEQ ID NO 28
<211> LENGTH: 120
<212> TYPE: PRT
<213> ORGANISM: Artificial Sequence
<220> FEATURE:
<223> OTHER INFORMATION: AM-2-VH

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gln Asn
            20                  25                  30

Ala Trp Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: AM-3-VH

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Met Ser Gly
            20                  25                  30
```

```
Gln Thr Ser Trp Val Arg Arg Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
            115                 120

<210> SEQ ID NO 30
<211> LENGTH: 120
<212> TYPE: PRT
<213> ORGANISM: Artificial Sequence
<220> FEATURE:
<223> OTHER INFORMATION: AM-4-VH

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ala Gly
            20                  25                  30

Gln Ser Ser Trp Val Arg Arg Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
            115                 120

<210> SEQ ID NO 31
<211> LENGTH: 120
<212> TYPE: PRT
<213> ORGANISM: Artificial Sequence
<220> FEATURE:
<223> OTHER INFORMATION: AM-5-VH

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Gln
            20                  25                  30

Gln Ala Ser Trp Val Arg Arg Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95
Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 32
<211> LENGTH: 120
<212> TYPE: PRT
<213> ORGANISM: Artificial Sequence
<220> FEATURE:
<223> OTHER INFORMATION: AM-6-VH

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Arg Asn
            20                  25                  30

Ala Trp Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: AM-7-VH

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Gln
            20                  25                  30

Gln Ala Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 34
<211> LENGTH: 120
```

```
<212> TYPE: PRT
<213> ORGANISM: Artificial Sequence
<220> FEATURE:
<223> OTHER INFORMATION: AM-8-VH

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Thr Gln
            20                  25                  30

Gln Ala Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: AM-9-VH

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Gly Gln
            20                  25                  30

Gln Ala Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: BADD197-1181 VL

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                    20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: BADD412-2513 VL

<400> SEQUENCE: 37

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: BADD456-2928 VL

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105
```

<210> SEQ ID NO 39
<211> LENGTH: 107
<212> TYPE: PRT
<213> ORGANISM: Artificial Sequence
<220> FEATURE:
<223> OTHER INFORMATION: BADD466-3164 VL

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Lys Ile Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: BADD466-3165 VL

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: BADD466-3166 VL

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                35                  40                  45
Tyr Asp Ala Ser Ser Arg Ala Thr Gly Ile Pro Asp Arg Phe Ser Gly
         50                  55                  60
Ser Gly Ser Gly Thr Asp Phe Thr Leu Thr Ile Ser Arg Leu Glu Pro
 65                  70                  75                  80
Glu Asp Phe Ala Val Tyr Tyr Cys Gln Gln Tyr Gly Ser Ser Pro Leu
                 85                  90                  95
Thr Phe Gly Gly Gly Thr Lys Val Glu Ile Lys
                100                 105

<210> SEQ ID NO 42
<211> LENGTH: 107
<212> TYPE: PRT
<213> ORGANISM: Artificial Sequence
<220> FEATURE:
<223> OTHER INFORMATION: BADD466-3167 VL

<400> SEQUENCE: 42

Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Val Ser Ser Tyr
                 20                  25                  30
Leu Ala Trp Tyr Gln Gln Lys Pro Gly Gln Ala Pro Arg Leu Leu Ile
             35                  40                  45
Tyr Asp Ala Ser Asn Arg Ala Thr Gly Ile Pro Ala Arg Phe Ser Gly
         50                  55                  60
Ser Gly Ser Gly Thr Asp Phe Thr Leu Thr Ile Ser Arg Leu Glu Pro
 65                  70                  75                  80
Glu Asp Phe Ala Val Tyr Tyr Cys Gln Gln Tyr Gly Ser Ser Pro Leu
                 85                  90                  95
Thr Phe Gly Gly Gly Thr Lys Val Glu Ile Lys
                100                 105

<210> SEQ ID NO 43
<211> LENGTH: 107
<212> TYPE: PRT
<213> ORGANISM: Artificial Sequence
<220> FEATURE:
<223> OTHER INFORMATION: BADD466-3168 VL

<400> SEQUENCE: 43

Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Tyr
                 20                  25                  30
Leu Ala Trp Tyr Gln Gln Lys Pro Gly Gln Ala Pro Arg Leu Leu Ile
             35                  40                  45
Tyr Asp Ala Ser Asn Arg Ala Thr Gly Ile Pro Ala Arg Phe Ser Gly
         50                  55                  60
Ser Gly Ser Gly Thr Asp Phe Thr Leu Thr Ile Ser Arg Leu Glu Pro
 65                  70                  75                  80
Glu Asp Phe Ala Val Tyr Tyr Cys Gln Gln Tyr Gly Ser Ser Pro Leu
                 85                  90                  95
Thr Phe Gly Gly Gly Thr Lys Val Glu Ile Lys
                100                 105

<210> SEQ ID NO 44
<211> LENGTH: 108
```

```
<212> TYPE: PRT
<213> ORGANISM: Artificial Sequence
<220> FEATURE:
<223> OTHER INFORMATION: BADD466-3169 VL

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: BADD466-3170 VL

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: BADD466-3171 VL

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Ser Phe Ser Gly
```

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: BADD466-3172 VL

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Ala Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Ile
                85                  90                  95

Thr Phe Gly Gly Gly Thr Lys Val Glu Ile Lys
            100                 105

<210> SEQ ID NO 48
<211> LENGTH: 6
<212> TYPE: PRT
<213> ORGANISM: Artificial Sequence
<220> FEATURE:
<223> OTHER INFORMATION: CDRH1 consensus sequence 1
<220> FEATURE:
<221> NAME/KEY: VARIANT
<222> LOCATION: (1)..(1)
<223> OTHER INFORMATION: Arg, Ser, Ala, Gly, Lys, Met, or Thr
<220> FEATURE:
<221> NAME/KEY: VARIANT
<222> LOCATION: (2)..(2)
<223> OTHER INFORMATION: Gln, Ser, Ala, Gly, Arg, or Thr
<220> FEATURE:
<221> NAME/KEY: VARIANT
<222> LOCATION: (3)..(3)
<223> OTHER INFORMATION: Asn, Tyr, Gly, or Gln
<220> FEATURE:
<221> NAME/KEY: VARIANT
<222> LOCATION: (4)..(4)
<223> OTHER INFORMATION: Ala or Gln
<220> FEATURE:
<221> NAME/KEY: VARIANT
<222> LOCATION: (5)..(5)
<223> OTHER INFORMATION: Trp, Met, Ala, Ser, or Thr

<400> SEQUENCE: 48

Xaa Xaa Xaa Xaa Xaa Ser
1               5

<210> SEQ ID NO 49
<211> LENGTH: 6
<212> TYPE: PRT

```
<213> ORGANISM: Artificial Sequence
<220> FEATURE:
<223> OTHER INFORMATION: CDRH1 consensus sequence 2
<220> FEATURE:
<221> NAME/KEY: VARIANT
<222> LOCATION: (1)..(1)
<223> OTHER INFORMATION: Arg or Ala
<220> FEATURE:
<221> NAME/KEY: VARIANT
<222> LOCATION: (2)..(2)
<223> OTHER INFORMATION: Gln or Arg

<400> SEQUENCE: 49

Xaa Xaa Asn Ala Trp Ser
1               5

<210> SEQ ID NO 50
<211> LENGTH: 6
<212> TYPE: PRT
<213> ORGANISM: Artificial Sequence
<220> FEATURE:
<223> OTHER INFORMATION: CDRH1 consensus sequence 3
<220> FEATURE:
<221> NAME/KEY: VARIANT
<222> LOCATION: (1)..(1)
<223> OTHER INFORMATION: Lys, Met, or Gly
<220> FEATURE:
<221> NAME/KEY: VARIANT
<222> LOCATION: (2)..(2)
<223> OTHER INFORMATION: Ala or Ser
<220> FEATURE:
<221> NAME/KEY: VARIANT
<222> LOCATION: (5)..(5)
<223> OTHER INFORMATION: Ser or Thr

<400> SEQUENCE: 50

Xaa Xaa Gly Gln Xaa Ser
1               5

<210> SEQ ID NO 51
<211> LENGTH: 6
<212> TYPE: PRT
<213> ORGANISM: Artificial Sequence
<220> FEATURE:
<223> OTHER INFORMATION: CDRH1 consensus sequence 4
<220> FEATURE:
<221> NAME/KEY: VARIANT
<222> LOCATION: (1)..(1)
<223> OTHER INFORMATION: Ser, Arg, Thr, or Gly
<220> FEATURE:
<221> NAME/KEY: VARIANT
<222> LOCATION: (2)..(2)
<223> OTHER INFORMATION: Ala, Ser, Thr, or Gly

<400> SEQUENCE: 51

Xaa Xaa Gln Gln Ala Ser
1               5

<210> SEQ ID NO 52
<211> LENGTH: 12
<212> TYPE: PRT
<213> ORGANISM: Artificial Sequence
<220> FEATURE:
<223> OTHER INFORMATION: XASQSVXSSYLA
<220> FEATURE:
<221> NAME/KEY: VARIANT
<222> LOCATION: (1)..(1)
<223> OTHER INFORMATION: Arg or Gly
<220> FEATURE:
<221> NAME/KEY: VARIANT
<222> LOCATION: (7)..(7)
<223> OTHER INFORMATION: absent or Ser
```

```
<400> SEQUENCE: 52

Xaa Ala Ser Gln Ser Val Xaa Ser Ser Tyr Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: CDRL2 consensus sequence
<220> FEATURE:
<221> NAME/KEY: VARIANT
<222> LOCATION: (1)..(1)
<223> OTHER INFORMATION: Asp or Gly
<220> FEATURE:
<221> NAME/KEY: VARIANT
<222> LOCATION: (4)..(4)
<223> OTHER INFORMATION: Asn, Ser, or Thr

<400> SEQUENCE: 53

Xaa Ala Ser Xaa Arg Ala Thr
1               5

<210> SEQ ID NO 54
<211> LENGTH: 9
<212> TYPE: PRT
<213> ORGANISM: Artificial Sequence
<220> FEATURE:
<223> OTHER INFORMATION: CDRL3 consensus sequence
<220> FEATURE:
<221> NAME/KEY: VARIANT
<222> LOCATION: (8)..(8)
<223> OTHER INFORMATION: Leu or Ile

<400> SEQUENCE: 54

Gln Gln Tyr Gly Ser Ser Pro Xaa Thr
1               5

<210> SEQ ID NO 55
<211> LENGTH: 120
<212> TYPE: PRT
<213> ORGANISM: Artificial Sequence
<220> FEATURE:
<223> OTHER INFORMATION: VH consensus sequence
<220> FEATURE:
<221> NAME/KEY: VARIANT
<222> LOCATION: (15)..(15)
<223> OTHER INFORMATION: Gly or Arg
<220> FEATURE:
<221> NAME/KEY: VARIANT
<222> LOCATION: (30)..(30)
<223> OTHER INFORMATION: Arg, Ser, Ala, Gly, Lys, Met, or Thr
<220> FEATURE:
<221> NAME/KEY: VARIANT
<222> LOCATION: (31)..(31)
<223> OTHER INFORMATION: Gln, Ser, Ala, Gly, Arg, or Thr
<220> FEATURE:
<221> NAME/KEY: VARIANT
<222> LOCATION: (32)..(32)
<223> OTHER INFORMATION: Asn, Tyr, Gly, or Gln
<220> FEATURE:
<221> NAME/KEY: VARIANT
<222> LOCATION: (33)..(33)
<223> OTHER INFORMATION: Ala or Gln
<220> FEATURE:
<221> NAME/KEY: VARIANT
<222> LOCATION: (34)..(34)
<223> OTHER INFORMATION: Trp, Met, Ala, Ser, or Thr
<220> FEATURE:
<221> NAME/KEY: VARIANT
<222> LOCATION: (39)..(39)
<223> OTHER INFORMATION: Arg or Gln
```

<400> SEQUENCE: 55

| Glu | Val | Gln | Leu | Val | Glu | Ser | Gly | Gly | Gly | Leu | Val | Gln | Pro | Xaa | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Xaa | Xaa | Xaa |
|---|---|---|---|---|---|---|---|---|---|---|---|---|---|---|---|
| | | | 20 | | | | | 25 | | | | | 30 | | |

| Xaa | Xaa | Ser | Trp | Val | Arg | Xaa | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Gly | Gly | Asp | Tyr | Gly | Gly | Asn | Tyr | Phe | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | 120 | |

<210> SEQ ID NO 56
<211> LENGTH: 108
<212> TYPE: PRT
<213> ORGANISM: Artificial Sequence
<220> FEATURE:
<223> OTHER INFORMATION: VL consensus sequence
<220> FEATURE:
<221> NAME/KEY: VARIANT
<222> LOCATION: (9)..(9)
<223> OTHER INFORMATION: Ala or Gly
<220> FEATURE:
<221> NAME/KEY: VARIANT
<222> LOCATION: (24)..(24)
<223> OTHER INFORMATION: Arg or Gly
<220> FEATURE:
<221> NAME/KEY: VARIANT
<222> LOCATION: (30)..(30)
<223> OTHER INFORMATION: absent or Ser
<220> FEATURE:
<221> NAME/KEY: VARIANT
<222> LOCATION: (43)..(43)
<223> OTHER INFORMATION: Gln or Leu
<220> FEATURE:
<221> NAME/KEY: VARIANT
<222> LOCATION: (51)..(51)
<223> OTHER INFORMATION: Asp or Gly
<220> FEATURE:
<221> NAME/KEY: VARIANT
<222> LOCATION: (54)..(54)
<223> OTHER INFORMATION: Asn, Ser, or Thr
<220> FEATURE:
<221> NAME/KEY: VARIANT
<222> LOCATION: (61)..(61)
<223> OTHER INFORMATION: Ala or Asp
<220> FEATURE:
<221> NAME/KEY: VARIANT
<222> LOCATION: (62)..(62)
<223> OTHER INFORMATION: Ser or Arg
<220> FEATURE:
<221> NAME/KEY: VARIANT
<222> LOCATION: (78)..(78)
<223> OTHER INFORMATION: Arg or Ser
<220> FEATURE:
<221> NAME/KEY: VARIANT
<222> LOCATION: (97)..(97)
<223> OTHER INFORMATION: Leu or Ile
<220> FEATURE:
<221> NAME/KEY: VARIANT
<222> LOCATION: (106)..(106)
<223> OTHER INFORMATION: Glu or Lys

<400> SEQUENCE: 56

```
Glu Ile Val Leu Thr Gln Ser Pro Xaa Thr Leu Ser Leu Ser Pro Gly
1               5                   10                  15

Glu Arg Ala Thr Leu Ser Cys Xaa Ala Ser Gln Ser Val Xaa Ser Ser
            20                  25                  30

Tyr Leu Ala Trp Tyr Gln Gln Lys Pro Gly Xaa Ala Pro Arg Leu Leu
        35                  40                  45

Ile Tyr Xaa Ala Ser Xaa Arg Ala Thr Gly Ile Pro Xaa Xaa Phe Ser
    50                  55                  60

Gly Ser Gly Ser Gly Thr Asp Phe Thr Leu Thr Ile Ser Xaa Leu Glu
65              70                  75                  80

Pro Glu Asp Phe Ala Val Tyr Tyr Cys Gln Gln Tyr Gly Ser Ser Pro
                85                  90                  95

Xaa Thr Phe Gly Gly Gly Thr Lys Val Xaa Ile Lys
            100                 105
```

<210> SEQ ID NO 57
<211> LENGTH: 449
<212> TYPE: PRT
<213> ORGANISM: Artificial Sequence
<220> FEATURE:
<223> OTHER INFORMATION: pab2188 full length IgG1 heavy chain

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 58
<211> LENGTH: 449
<212> TYPE: PRT
<213> ORGANISM: Artificial Sequence
<220> FEATURE:
<223> OTHER INFORMATION: pab2188 full length IgG1 N297A heavy chain

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 59
<211> LENGTH: 446
<212> TYPE: PRT
<213> ORGANISM: Artificial Sequence
<220> FEATURE:
<223> OTHER INFORMATION: pab2188 full length IgG4 S228P heavy chain

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95

Ala Lys Gly Gly Asp Tyr Gly Gly Asn Tyr Phe Asp Tyr Trp Gly Gln
                100                 105                 110

Gly Thr Leu Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 60
<211> LENGTH: 449
<212> TYPE: PRT
<213> ORGANISM: Artificial Sequence
<220> FEATURE:
<223> OTHER INFORMATION: AM-1 full length IgG1 N297A heavy chain
```

-continued

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Ala Gly
            20                  25                  30

Gln Ser Ser Trp Val Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 61
<211> LENGTH: 449
<212> TYPE: PRT
<213> ORGANISM: Artificial Sequence
<220> FEATURE:
<223> OTHER INFORMATION: AM-2 full length IgG1 N297A heavy chain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Gln Asn
            20                  25                  30

Ala Trp Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 62
<211> LENGTH: 449
<212> TYPE: PRT
<213> ORGANISM: Artificial Sequence
<220> FEATURE:
<223> OTHER INFORMATION: AM-3 full length IgG1 N297A heavy chain

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Met Ser Gly
            20                  25                  30

Gln Thr Ser Trp Val Arg Arg Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
```

```
                225                 230                 235                 240
Pro Ser Val Phe Leu Phe Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 63
<211> LENGTH: 449
<212> TYPE: PRT
<213> ORGANISM: Artificial Sequence
<220> FEATURE:
<223> OTHER INFORMATION: AM-4 full length IgG1 N297A heavy chain

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ala Gly
            20                  25                  30

Gln Ser Ser Trp Val Arg Arg Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 64
<211> LENGTH: 449
<212> TYPE: PRT
<213> ORGANISM: Artificial Sequence
<220> FEATURE:
<223> OTHER INFORMATION: AM-5 full length IgG1 N297A heavy chain

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Gln
            20                  25                  30

Gln Ala Ser Trp Val Arg Arg Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50              55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Gly Asp Tyr Gly Asn Tyr Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 65
```

<211> LENGTH: 449
<212> TYPE: PRT
<213> ORGANISM: Artificial Sequence
<220> FEATURE:
<223> OTHER INFORMATION: AM-6 full length IgG1 N297A heavy chain

<400> SEQUENCE: 65

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Arg Asn
            20                  25                  30

Ala Trp Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 66
<211> LENGTH: 449
<212> TYPE: PRT
<213> ORGANISM: Artificial Sequence
<220> FEATURE:
<223> OTHER INFORMATION: AM-7 full length IgG1 N297A heavy chain

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Gln
            20                  25                  30

Gln Ala Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 67
<211> LENGTH: 449
<212> TYPE: PRT
<213> ORGANISM: Artificial Sequence
<220> FEATURE:
<223> OTHER INFORMATION: AM-8 full length IgG1 N297A heavy chain

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Thr Gln
            20                  25                  30

Gln Ala Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
                195                 200                 205
Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Ala Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 68
<211> LENGTH: 449
<212> TYPE: PRT
<213> ORGANISM: Artificial Sequence
<220> FEATURE:
<223> OTHER INFORMATION: AM-9 full length IgG1 N297A heavy chain

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Gly Gln
                20                  25                  30

Gln Ala Ser Trp Val Arg Arg Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Tyr Gly Gly Asn Tyr Phe Asp Tyr Trp Gly Gln
                100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 69
<211> LENGTH: 214
<212> TYPE: PRT
<213> ORGANISM: Artificial Sequence
<220> FEATURE:
<223> OTHER INFORMATION: BADD466-3171 full length light chain sequence

<400> SEQUENCE: 69

Glu Ile Val Leu Thr Gln Ser Pro Ala Thr Leu Ser Leu Ser Pro Gly
1               5                   10                  15

-continued

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Ser Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 329
<212> TYPE: PRT
<213> ORGANISM: Artificial Sequence
<220> FEATURE:
<223> OTHER INFORMATION: Human IgG1 G1m3 allotype (without C-terminal
      lysine)

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 71
<211> LENGTH: 330
<212> TYPE: PRT
<213> ORGANISM: Artificial Sequence
<220> FEATURE:
<223> OTHER INFORMATION: Human IgG1 G1m3 allotype

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 329
<212> TYPE: PRT
<213> ORGANISM: Artificial Sequence
<220> FEATURE:
<223> OTHER INFORMATION: IgG1 N297A (without C-terminal lysine)

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 73
<211> LENGTH: 330
<212> TYPE: PRT
<213> ORGANISM: Artificial Sequence
<220> FEATURE:
<223> OTHER INFORMATION: IgG1 N297A

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 74
<211> LENGTH: 326
<212> TYPE: PRT
<213> ORGANISM: Artificial Sequence
<220> FEATURE:
<223> OTHER INFORMATION: IgG4 S228P (without C-terminal lysine)

<400> SEQUENCE: 74

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285
```

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 75
<211> LENGTH: 327
<212> TYPE: PRT
<213> ORGANISM: Artificial Sequence
<220> FEATURE:
<223> OTHER INFORMATION: IgG4 S228P

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 76
<211> LENGTH: 107
<212> TYPE: PRT
<213> ORGANISM: Artificial Sequence
<220> FEATURE:
<223> OTHER INFORMATION: Human kappa light chain constant region IGKC*01
      Km3 allotype

<400> SEQUENCE: 76

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Human kappa light chain constant region IGKC*01
      Km3 allotype (with T109S mutation)

<400> SEQUENCE: 77

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 78
<211> LENGTH: 301
<212> TYPE: PRT
<213> ORGANISM: Homo sapiens

<400> SEQUENCE: 78

Met Phe Ser His Leu Pro Phe Asp Cys Val Leu Leu Leu Leu Leu
1               5                   10                  15

```
Leu Leu Thr Arg Ser Ser Glu Val Glu Tyr Arg Ala Glu Val Gly Gln
        20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 79
<211> LENGTH: 280
<212> TYPE: PRT
<213> ORGANISM: Homo sapiens

<400> SEQUENCE: 79

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95
```

```
Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
            195                 200                 205

Ser Lys Glu Lys Ile Gln Asn Leu Ser Leu Ile Ser Leu Ala Asn Leu
210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
            260                 265                 270

Leu Gly Cys Arg Phe Ala Met Pro
            275                 280

<210> SEQ ID NO 80
<211> LENGTH: 117
<212> TYPE: PRT
<213> ORGANISM: Artificial Sequence
<220> FEATURE:
<223> OTHER INFORMATION: pab1944w VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asn Pro Ser Asn Gly Arg Thr Asn Tyr Asn Glu Lys Phe
    50                  55                  60

Lys Thr Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Tyr Phe Asp Tyr Trp Gly Gln Gly Thr Leu
            100                 105                 110

Val Thr Val Ser Ser
        115

<210> SEQ ID NO 81
<211> LENGTH: 107
<212> TYPE: PRT
<213> ORGANISM: Artificial Sequence
<220> FEATURE:
<223> OTHER INFORMATION: pab1944w VL
```

-continued

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Arg Ile Asn
            20                  25                  30

Ile Gly Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Gly Gln Phe Pro Trp
                85                  90                  95

Thr Phe Gly Gln Gly Thr Lys Leu Glu Ile Lys
            100                 105

<210> SEQ ID NO 82
<211> LENGTH: 118
<212> TYPE: PRT
<213> ORGANISM: Artificial Sequence
<220> FEATURE:
<223> OTHER INFORMATION: Hum11 VH

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 83
<211> LENGTH: 111
<212> TYPE: PRT
<213> ORGANISM: Artificial Sequence
<220> FEATURE:
<223> OTHER INFORMATION: Hum11 VL

<400> SEQUENCE: 83

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
            85                  90                  95

Lys Asp Pro Ser Thr Phe Gly Gly Gly Thr Lys Val Glu Ile Lys
        100                 105                 110

<210> SEQ ID NO 84
<211> LENGTH: 98
<212> TYPE: PRT
<213> ORGANISM: Homo sapiens

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 85
<211> LENGTH: 95
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
            85                  90                  95

<210> SEQ ID NO 86
<211> LENGTH: 95
<212> TYPE: PRT
<213> ORGANISM: Homo sapiens

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                85                  90                  95

<210> SEQ ID NO 87
<211> LENGTH: 96
<212> TYPE: PRT
<213> ORGANISM: Homo sapiens

<400> SEQUENCE: 87

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

<210> SEQ ID NO 88
<211> LENGTH: 96
<212> TYPE: PRT
<213> ORGANISM: Homo sapiens

<400> SEQUENCE: 88

Glu Ile Val Leu Thr Gln Ser Pro Ala Thr Leu Ser Leu Ser Pro Gly
 1               5                  10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

<210> SEQ ID NO 89
<211> LENGTH: 446
<212> TYPE: PRT
<213> ORGANISM: Artificial Sequence
<220> FEATURE:
<223> OTHER INFORMATION: pab1944w (IgG1 N297A) full length heavy chain

<400> SEQUENCE: 89

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met

```
            35                  40                  45
Gly Glu Ile Asn Pro Ser Asn Gly Arg Thr Asn Tyr Asn Glu Lys Phe
 50                  55                  60

Lys Thr Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Tyr Leu Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 90
```

```
<211> LENGTH: 214
<212> TYPE: PRT
<213> ORGANISM: Artificial Sequence
<220> FEATURE:
<223> OTHER INFORMATION: pab1944w (IgG1 N297A) full length light chain

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Arg Ile Asn
            20                  25                  30

Ile Gly Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Gly Gln Phe Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 444
<212> TYPE: PRT
<213> ORGANISM: Artificial Sequence
<220> FEATURE:
<223> OTHER INFORMATION: Hum11 (IgG4 S228P) full length heavy chain

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
```

```
                100             105             110
Thr Val Thr Val Ser Ser Ala Ser Thr Lys Gly Pro Ser Val Phe Pro
            115                 120             125

Leu Ala Pro Cys Ser Arg Ser Thr Ser Glu Ser Thr Ala Ala Leu Gly
        130                 135             140

Cys Leu Val Lys Asp Tyr Phe Pro Glu Pro Val Thr Val Ser Trp Asn
145                 150             155                 160

Ser Gly Ala Leu Thr Ser Gly Val His Thr Phe Pro Ala Val Leu Gln
                165                 170             175

Ser Ser Gly Leu Tyr Ser Leu Ser Ser Val Val Thr Val Pro Ser Ser
            180                 185             190

Ser Leu Gly Thr Lys Thr Tyr Thr Cys Asn Val Asp His Lys Pro Ser
        195                 200             205

Asn Thr Lys Val Asp Lys Arg Val Glu Ser Lys Tyr Gly Pro Pro Cys
    210                 215             220

Pro Pro Cys Pro Ala Pro Glu Phe Leu Gly Gly Pro Ser Val Phe Leu
225                 230             235             240

Phe Pro Pro Lys Pro Lys Asp Thr Leu Met Ile Ser Arg Thr Pro Glu
                245             250                 255

Val Thr Cys Val Val Val Asp Val Ser Gln Glu Asp Pro Glu Val Gln
            260                 265             270

Phe Asn Trp Tyr Val Asp Gly Val Glu Val His Asn Ala Lys Thr Lys
        275                 280             285

Pro Arg Glu Glu Gln Phe Asn Ser Thr Tyr Arg Val Val Ser Val Leu
    290                 295             300

Thr Val Leu His Gln Asp Trp Leu Asn Gly Lys Glu Tyr Lys Cys Lys
305                 310             315                 320

Val Ser Asn Lys Gly Leu Pro Ser Ser Ile Glu Lys Thr Ile Ser Lys
                325             330                 335

Ala Lys Gly Gln Pro Arg Glu Pro Gln Val Tyr Thr Leu Pro Pro Ser
            340                 345             350

Gln Glu Glu Met Thr Lys Asn Gln Val Ser Leu Thr Cys Leu Val Lys
        355                 360             365

Gly Phe Tyr Pro Ser Asp Ile Ala Val Glu Trp Glu Ser Asn Gly Gln
    370                 375             380

Pro Glu Asn Asn Tyr Lys Thr Thr Pro Pro Val Leu Asp Ser Asp Gly
385                 390             395                 400

Ser Phe Phe Leu Tyr Ser Arg Leu Thr Val Asp Lys Ser Arg Trp Gln
                405             410                 415

Glu Gly Asn Val Phe Ser Cys Ser Val Met His Glu Ala Leu His Asn
            420                 425             430

His Tyr Thr Gln Lys Ser Leu Ser Leu Ser Leu Gly
        435                 440

<210> SEQ ID NO 92
<211> LENGTH: 218
<212> TYPE: PRT
<213> ORGANISM: Artificial Sequence
<220> FEATURE:
<223> OTHER INFORMATION: Hum11 (IgG4 S228P) full length light chain

<400> SEQUENCE: 92

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
```

```
            20                  25                  30
Gly Thr Ser Leu Met Gln Trp Tyr Gln Gln Lys Pro Gly Lys Ala Pro
         35                  40                  45

Lys Leu Leu Ile Tyr Ala Ala Ser Asn Val Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Arg
                 85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 93
<211> LENGTH: 7
<212> TYPE: PRT
<213> ORGANISM: Homo sapiens

<400> SEQUENCE: 93

Pro Val Phe Glu Cys Gly Asn
1               5

<210> SEQ ID NO 94
<211> LENGTH: 18
<212> TYPE: PRT
<213> ORGANISM: Homo sapiens

<400> SEQUENCE: 94

Val Cys Trp Gly Lys Gly Ala Cys Pro Val Phe Glu Cys Gly Asn Val
1               5                   10                  15

Val Leu

<210> SEQ ID NO 95
<211> LENGTH: 10
<212> TYPE: PRT
<213> ORGANISM: Homo sapiens

<400> SEQUENCE: 95

Arg Ile Gln Ile Pro Gly Ile Met Asn Asp
1               5                   10

<210> SEQ ID NO 96
<211> LENGTH: 17
<212> TYPE: PRT
<213> ORGANISM: Homo sapiens
```

-continued

<400> SEQUENCE: 96

Arg Ile Gln Ile Pro Gly Ile Met Asn Asp Glu Lys Phe Asn Leu Lys
1               5                   10                  15

Leu

<210> SEQ ID NO 97
<211> LENGTH: 7
<212> TYPE: PRT
<213> ORGANISM: Homo sapiens

<400> SEQUENCE: 97

Glu Lys Phe Asn Leu Lys Leu
1               5

<210> SEQ ID NO 98
<211> LENGTH: 9
<212> TYPE: PRT
<213> ORGANISM: Homo sapiens

<400> SEQUENCE: 98

Pro Ala Ala Pro Gly Asn Leu Val Pro
1               5

<210> SEQ ID NO 99
<211> LENGTH: 9
<212> TYPE: PRT
<213> ORGANISM: Homo sapiens

<400> SEQUENCE: 99

Gly Lys Gly Ala Cys Pro Val Phe Glu
1               5

<210> SEQ ID NO 100
<211> LENGTH: 8
<212> TYPE: PRT
<213> ORGANISM: Homo sapiens

<400> SEQUENCE: 100

Asp Phe Thr Ala Ala Phe Pro Arg
1               5

<210> SEQ ID NO 101
<211> LENGTH: 280
<212> TYPE: PRT
<213> ORGANISM: Artificial Sequence
<220> FEATURE:
<223> OTHER INFORMATION: Human TIM-3 F40A

<400> SEQUENCE: 101

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Ala Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

```
Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
    210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
            260                 265                 270

Leu Gly Cys Arg Phe Ala Met Pro
        275                 280

<210> SEQ ID NO 102
<211> LENGTH: 179
<212> TYPE: PRT
<213> ORGANISM: Homo sapiens

<400> SEQUENCE: 102

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg
```